United States Patent

Muchowski et al.

[11] 4,410,534
[45] Oct. 18, 1983

[54] 3-SUBSTITUTED-5,6,7,8-TETRAHYDROPYR-ROLO[1,2-a]-PYRIDINE-AND 6,7,8,9-TETRAHYDRO-5H-PYRROLO[1,2,-a]-AZEPINE CARBOXYLIC ACID DERIVATIVES USEFUL AS BLOOD PLATELET AGGREGATION INHIBITORS

[75] Inventors: Joseph M. Muchowski, Sunnyvale; Arthur F. Kluge, Los Altos, both of Calif.

[73] Assignee: Syntex (U.S.A.) Inc., Palo Alto, Calif.

[21] Appl. No.: 243,322

[22] Filed: Mar. 13, 1981

Related U.S. Application Data

[63] Continuation-in-part of Ser. No. 107,219, Dec. 26, 1979.

[51] Int. Cl.³ ................. A61K 31/44; C07D 221/02
[52] U.S. Cl. ................................. 424/263; 546/112
[58] Field of Search ..................... 546/112; 424/263

[56] References Cited

U.S. PATENT DOCUMENTS 4,087,539  5/1978  Muchowski et al. .......... 260/326.22
4,089,969  5/1978  Muchowski et al. .......... 260/326.22

*Primary Examiner*—Henry R. Jiles
*Assistant Examiner*—Robert C. Whittenbaugh
*Attorney, Agent, or Firm*—Tom M. Moran; Alan M. Krubiner

[57] ABSTRACT

Novel 3-substituted-5,6,7,8-tetrahydropyrrolo[1,2-a]pyridine-8-carboxylic acid and 3-substituted-6,7,8,9-tetrahydro[1,2-a]azepine-9-carboxylic acid compounds represented by the formula

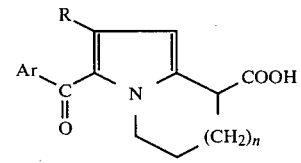

and the pharmaceutically acceptable, non-toxic esters and salts thereof, wherein R is hydrogen or a lower alkyl group containing from 1 to 4 carbon atoms, n is the integer selected from the integers 1 or 2 and Ar is a 6- or 5-member ring. These compounds are useful as anti-inflammatory, analgesic and antipyretic agents, platelet aggregation inhibitors, and as smooth muscle relaxants.

4 Claims, No Drawings

3-SUBSTITUTED-5,6,7,8-TETRAHYDROPYRROLO[1,2-a]-PYRIDINE-AND 6,7,8,9-TETRAHYDRO-5H-PYRROLO[1,2-A]-AZEPINE CARBOXYLIC ACID DERIVATIVES USEFUL AS BLOOD PLATELET AGGREGATION INHIBITORS

This is a continuation-in-part of application Ser. No. 107,219, filed Dec. 26, 1979.

BACKGROUND OF THE INVENTION

1. Field of the Invention

The present invention relates to (i) certain novel pyrrole-carboxylic acid compounds; (ii) the use of these compounds as anti-inflammatory, analgetic, fibrinolytic or antipyretic agents or as smooth muscle relaxants, or platelet aggregation inhibitors; (iii) pharmaceutical compositions containing these compounds; (iv) processes for the production of these compounds and (v) novel intermediates used for making these compounds.

2. Prior Art

U.S. Pat. No. 4,087,539 (issued May 2, 1978), U.S. Pat. No. 4,089,969 (issued May 16, 1978) and U.S. Pat. No. 4,097,579 (issued June 27, 1978), all to Muchowski and Kluge, disclose a linear 5-membered (pyrrole) ring rather than applicants' 6-member (pyridine) ring or 7-membered (azepine) ring.

SUMMARY AND FURTHER DISCUSSION

The novel pyrrole-carboxylic acids of this invention are represented by the formula

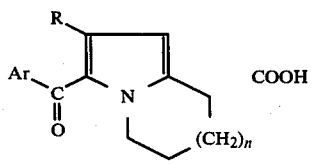

and the pharmaceutically acceptable, non-toxic esters having from 1 to 12 carbon atoms and salts thereof, wherein Ar is a radical selected from the group of those having the formula

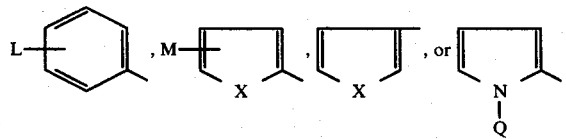

in which

X is sulfur or oxygen,

L is hydrogen, alkyl containing 1 to 4 carbon atoms, alkoxy containing 1 to 4 carbon atoms, Br, Cl, F, $CF_3$, CN, $SR_3$,

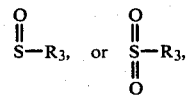

wherein $R_3$ is alkyl containing 1 to 4 carbon atoms
M is hydrogen, methyl, Cl or Br, Q is hydrogen or alkyl containing 1 to 4 carbon atoms;

n is an integer selected from the integers 1 or 2; and

R is hydrogen, alkyl containing from 1 to 4 carbon atoms, Cl or Br;

In the compounds having the grouping

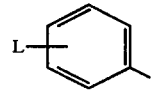

L can be in the ortho-, meta- or para-position.

In the compounds having the grouping

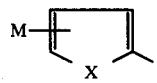

M can be at the 3-, 4- or 5- position of the ring.

The compounds of the present invention as described above and more fully below exhibit anti-inflammatory, analgesic and anti-pyretic activities and thus are useful in the treatment of inflammation, pain and/or pyrexia in mammals, as described hereinafter in detail. They are also smooth muscle relaxants and platelet aggregation inhibitors.

The term "pharmaceutically acceptable, non-toxic esters and salts" as used herein refers to "alkyl esters" derived from hydrocarbons of branched or straight chain having from one to twelve carbon atoms and salts derived from inorganic and organic bases, respectively.

Typical pharmaceutically acceptable, non-toxic alkyl ester groups are, for example, methyl, ethyl, propyl, isopropyl, butyl, t-butyl, isoamyl, pentyl, isopentyl, hexyl, octyl, nonyl, isodecyl, 6-methyldecyl and dodecyl esters.

Pharmaceutically acceptable, non-toxic salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

Typical alkyl groups containing one to four carbon atoms are methyl, ethyl, propyl, isopropyl, butyl and the like. Typical alkoxy groups containing one to four carbon atoms methoxy, ethoxy, propoxy, isopropoxy, butoxy and the like.

PROCESS OF PREPARATION

The novel compounds of the present invention can be prepared by a process illustrated by Reaction Sequence 1 as follows:

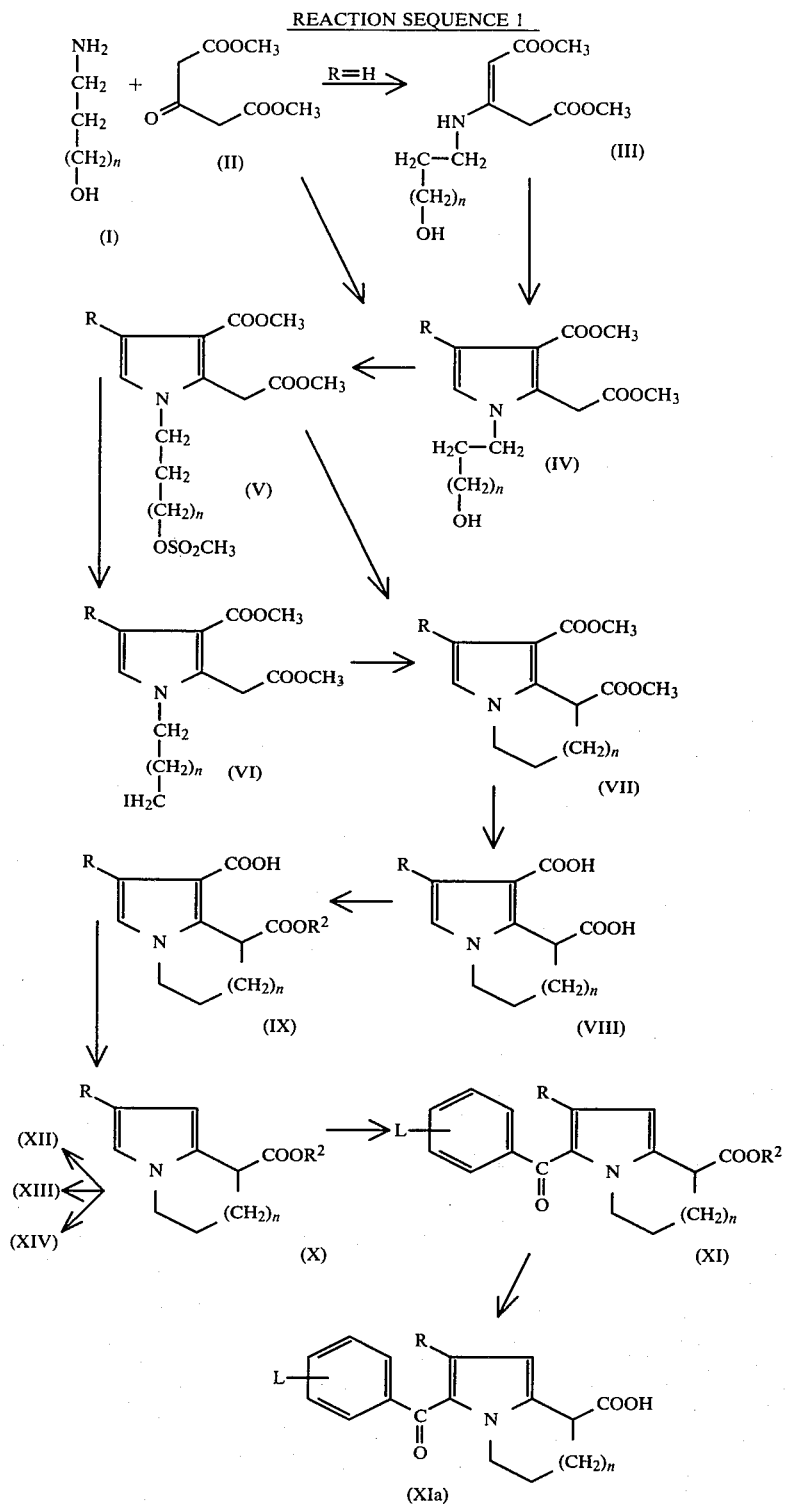

wherein X, L, M, Q, n and R have the above-indicated meaning and $R^2$ is a lower alkyl group of 1 to 4 carbon atoms, e.g., methyl, ethyl, isopropyl and n-butyl.

In practicing the process outlined above, for the preparation of a compound of Formula (IV) wherein R is hydrogen, equimolecular amounts of propanolamine (Formula (I) where n=1) or butanolamine (Formula (I) where n=2) and dimethyl 1,3-acetonedicarboxylate (II) are reacted at a temperature of from about 0° C. to about room temperature, to readily form a solution of the vinylamine (n=1 or 2) of Formula (III), which is then treated, preferably in situ, in a suitable inert organic solvent, under anhydrous conditions, with 2-bromoacetaldehyde or 2-chloroacetaldehyde, at from about 40° to about 100° C. for a period of time of from about 30 minutes to about 16 hours. Suitable solvents for this reaction are the aprotic solvents such as acetonitrile, tetrahydrofuran, dimethoxyethane, chloroform, dichloromethane and the like. In the preferred embodiments, the reaction is conducted in acetonitrile solution, at reflux temperature for about 1 hour. The 2-bromo-(chloro)-acetaldehyde reagents are known compounds, or can be obtained by pyrolysis of the corresponding diethyl acetals in the presence of oxalic acid dihydrate.

To prepare the compounds of Formula (IV) wherein R is a lower alkyl group, preferably straight chain, having 1 to 4 carbon atoms, an aqueous mixture of propanolamine or butanolamine (I) and dimethyl 1,3-acetonedicarboxylate (II) is treated with a compound of the formula

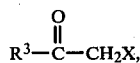

wherein X is bromo or chloro and $R^3$ is a lower alkyl group, preferably straight chain, of from 1 to 4 carbon atoms, and most preferably 1-bromoacetone, 1-bromo-2-butanone, 1-bromo-2-pentanone, and 1-bromo-2-hexanone, at from about 40° to about 100° C. for a period of time from about 30 minutes to about 16 hours. In the preferred embodiment the reaction is conducted at a temperature of from about −10° C. to about room temperature for from about 1 hour to about 6 hours. The

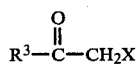

reagents are known compounds.

Esterification of compound (IV) with methanesulfonyl chloride in the presence of a tertiary amine, i.e., triethylamine, pyridine and the like, optionally in the presence of a cosolvent such as dichloromethane, at a temperature of from about −10° C. to about room temperature, for about 10 minutes to about 2 hours produces the corresponding mesylate of Formula (V), which is converted into the corresponding N-(3-iodopropyl)pyrrole or N-(4-iodobutyl)pyrrole of Formula (VI) by reaction with sodium iodide in acetonitrile solution, at reflux temperature for from about one to about ten hours.

Upon reaction of the iodopropyl or iodobutyl compounds of Formula (VI) with sodium hydride in a suitable inert organic solvent such as dimethylformamide there are obtained dimethyl-5,6,7,8-tetrahydropyrrolo[1,2-a]pyridine-1,8-dicarboxylate or dimethyl-6,7,8,9-tetrahydro-5H-pyrrolo[1,2-a]azepine-1,9-dicarboxylate, respectively, and the 2-alkyl substituted derivatives thereof (VII). This cyclization is conducted under an inert atmosphere, i.e., under argon or nitrogen atmosphere, at temperatures of the order of from about 15° to about 40° C., for a period of time of from about 15 minutes to about 4 hours. Best results are obtained conducting the reaction at room temperature, for about 30 minutes when R is hydrogen.

Alternatively, the compounds of Formula (VII) can be prepared by direct cyclization of the mesylate (V), with sodium hydride in dimethylformamide solution, at from about −10° C. to about room temperature, for from about 30 minutes to about 2 hours.

Basic hydrolysis of a compound of Formula (VII) with an alkali metal hydroxide or alkali metal carbonate, e.g., sodium hydroxide, potassium hydroxide, sodium carbonate, potassium carbonate and the like in an aqueous lower aliphatic alcohol, e.g., methanol or ethanol, at a temperature of between room temperature and reflux, for from about 4 to about 24 hours, affords the corresponding free diacids of Formula (VIII), i.e., 5,6,7,8-tetrahydropyrrolo[1,2-a]pyridine-1,8-dicarboxylic acid and 6,7,8,9-tetrahydro-5H-pyrrolo[1,2-a]azepine-1,9-dicarboxylic acid and the 2-alkyl derivatives thereof. The hydrolysis is preferably carried out using aqueous methanolic potassium hydroxide, at reflux temperature for about 10 hours.

The carboxylic acid group at the C-8 or C-9 position in the compounds (VIII) is then selectively esterified by treatment with a lower aliphatic alcohol, e.g., methanol, ethanol, isopropanol, n-butanol and the like in the presence of hydrogen chloride, to produce the corresponding alkyl 5,6,7,8-tetrahydropyrrolo[1,2-a]-pyridine-8-carboxylate-1-carboxylic acid and alkyl 6,7,8,9-tetrahydro-5H-pyrrolo[1,2-a]azepine-9-carboxylate-1-carboxylic acid of Formula (IX). The reaction is conducted at a temperature of from about 0° to about 50° C., for about 1 to about 4 hours.

Decarboxylation of the monoesterified compounds (IX) to the corresponding compounds of Formula (X), the key intermediates in the process for obtaining the compounds of the present invention, is achieved by heating a compound of Formula (IX) at an elevated temperature, of the order of from about 230° to about 280° C., for a period of time sufficient to complete the reaction. The course of the reaction can be followed by the rate of carbon dioxide evolution and thin-layer chromatographic analysis, decarboxylation being generally completed within from about 45 to about 90 minutes. The reaction product, namely, alkyl 5,6,7,8-tetrahydropyrrolo[1,2-a]pyridine-8-carboxylate and alkyl 6,7,8,9-tetrahydro-5H-pyrrolo[1,2-a]azepine-9-carboxylate and the 2-alkyl derivatives thereof (X) can be purified by chromatographic techniques. Alternatively, and particularly for the decarboxylation of small batches of compound (IX), the reaction product (X) can be distilled directly from the reaction vessel.

Condensation of a compound (X) with an amide of the formula

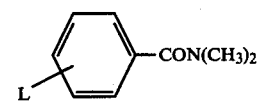

wherein L has the above-indicated meaning, affords the corresponding alkyl 3-aroyl-5,6,7,8-tetrahydropyrrolo[1,2-a]pyridine-8-carboxylate and alkyl 3-aroyl-6,7,8,9-tetrahydro-5H-pyrrolo[1,2-a]azepine-9-carboxylate (XI). This reaction is conducted in an inert organic aprotic solvent and in the presence of phosphorous oxychloride, at reflux temperature for from about 1 to about 175 hours, under an inert atmosphere, followed by further reflux in the presence of sodium acetate, for from about 2 to about 10 hours. Alternatively, instead of phosphorous oxychloride other acid chlorides such as phosgene or oxalyl chloride may be used.

In the preferred embodiments, this condensation is carried out by adding a solution of compound (X) in a suitable solvent to a previously refluxed mixture of 1.1 to 5 molar equivalents of both the desired amide and phosphorous oxychloride in the same solvent, refluxing the reaction mixture thus obtained for from about 6 to about 72 hours under an argon atmosphere and thereafter adding thereto from about 3 to about 10 molar equivalents of sodium acetate, followed by an additional reflux period for from about 4 to about 6 hours.

Adequate solvents for this reaction are the halogenated hydrocarbons such as dichloromethane, 1,2-dichloroethane, chloroform, carbon tetrachloride and the like, dimethoxyethane and tetrahydrofuran. The preferred solvent is 1,2-dichloroethane.

Representative of the N,N-dimethyl arylamides which can be used are:
N,N-dimethylbenzamide;
N,N-dimethyl-o-toluamide;
N,N-dimethyl-m-toluamide;
N,N-dimethyl-p-toluamide;
N,N-dimethyl-p-ethylbenzamide;
N,N-dimethyl-o-propylbenzamide;
N,N-dimethyl-m-butylbenzamide;
N,N-dimethyl-o-methoxybenzamide;
N,N-dimethyl-m-methoxybenzamide;
N,N-dimethyl-p-ethoxybenzamide;
N,N-dimethyl-p-isopropoxybenzamide;
N,N-dimethyl-p-butoxybenzamide;
N,N-dimethyl-o-chlorobenzamide;
N,N-dimethyl-m-chlorobenzamide;
N,N-dimethyl-p-chlorobenzamide;
N,N-dimethyl-o-fluorobenzamide;
N,N-dimethyl-p-fluorobenzamide;
N,N-dimethyl-m-bromobenzamide;
N,N-dimethyl-p-bromobenzamide;
N,N-dimethyl-p-methylthiobenzamide;
N,N-dimethyl-m-ethylthiobenzamide;
N,N-dimethyl-p-propylthiobenzamide;
N,N-dimethyl-o-methylsulfinylbenzamide;
N,N-dimethyl-m-ethylsulfinylbenzamide;
N,N-dimethyl-p-butylsulfinylbenzamide;
N,N-dimethyl-o-ethylsulfonylbenzamide;
N,N-dimethyl-m-methylsulfonylbenzamide; and
N,N-dimethyl-p-isopropylsulfonylbenzamide.

These amides are known, commercially available compounds or can be prepared in a conventional manner from the corresponding acids, i.e., by conversion into the acid chlorides followed by treatment with dimethylamine.

Upon alkaline hydrolysis of the alkyl ester group in a compound of Formula (XI) there is obtained the corresponding free acid of Formula (XIa). This hydrolysis is effected in a conventional manner, with an alkali metal hydroxide or alkali metal carbonate, e.g., sodium hydroxide, potassium hydroxide, sodium carbonate, potassium carbonate and the like, in an aqueous lower aliphatic alcohol, e.g., methanol, ethanol and the like, at a temperature of from about room temperature to reflux, for from about 15 minutes to about 2 hours, under an inert atmosphere. In the preferred embodiments, this hydrolysis is effected with aqueous methanolic potassium carbonate, at reflux temperature for about 30 minutes.

The compounds of Formula (XIa) can be resolved, according to methods known in the art, to obtain the corresponding individual isomers thereof. See, for example, U.S. Pat. No. 4,087,539 issued May 2, 1978 and U.S. Pat. No. 4,089,969 issued May 16, 1978.

Compounds of this invention which are represented by Formulas (XIIa), (XIIIa) and (XIVa) are prepared according to Reaction Sequence 2, as follows.

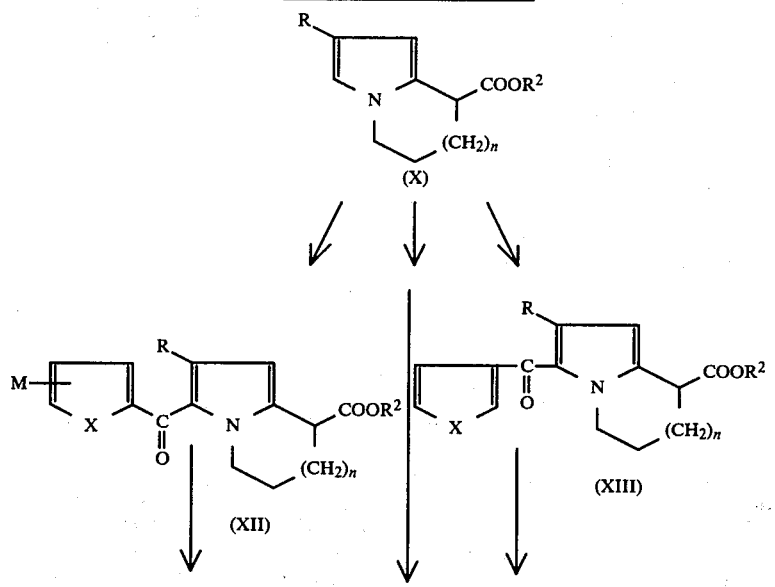

REACTION SEQUENCE 2 -continued

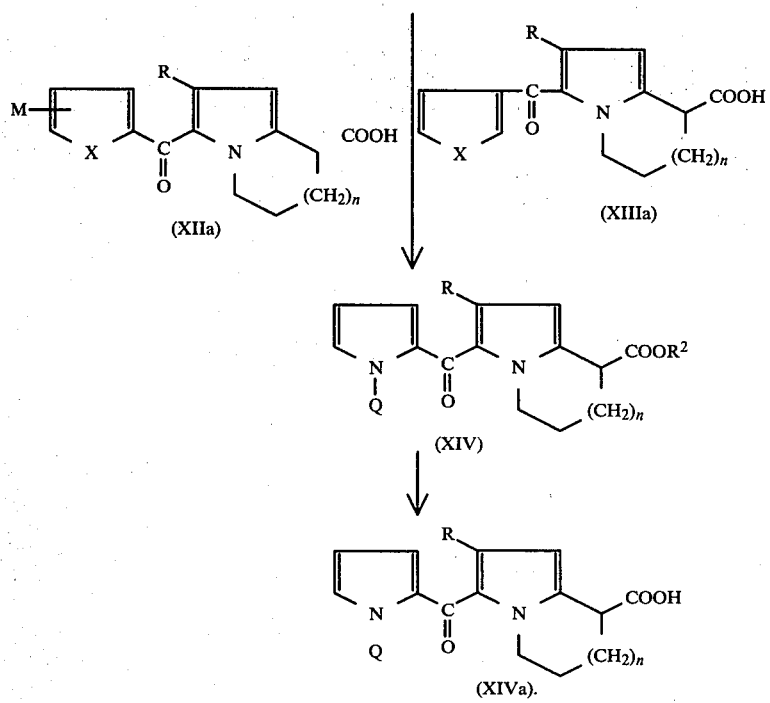

Condensation of a compound of Formula (X) with an amide of the formulas

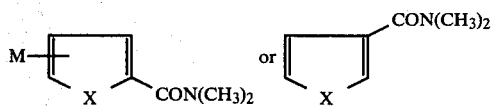

wherein X and M have the above indicated meaning, affords the corresponding alkyl 3-substituted-5,6,7,8-tetrahydropyrrolo-[1,2-a]pyridine-8-carboxylates and alkyl 3-substituted-6,7,8,9-tetrahydro-5H-pyrrolo[1,2-a]azepine-9-carboxylates of Formulas (XII) or (XIII), respectively.

This reaction is conducted in an inert organic aprotic solvent and in the presence of phosphorous oxychloride, at reflux temperature for from about 1 to about 72 hours, under an inert atmosphere, followed by further reflux in the presence of sodium acetate, for from about 2 to about 10 hours. Alternatively, instead of phosphorous oxychloride other acid chlorides such as phosgene or oxalyl chloride may be used.

In the preferred embodiments, this condensation is carried out by adding a solution of compound (X) in a suitable solvent to a previously refluxed mixture of 1.1 to 2 molar equivalents of both the desired amide and phosphorous oxychloride in the same solvent, refluxing the reaction mixture thus obtained for from about 2 to about 30 hours under an argon atmosphere and thereafter adding thereto from about 3 to about 10 molar equivalents of sodium acetate, followed by an additional reflux period for from about 4 to about 6 hours.

Adequate solvents for this reaction are the halogenated hydrocarbons such as dichloromethane, 1,2-dichloroethane, chloroform, carbon tetrachloride and the like, dimethoxyethane and tetrahydrofuran. The preferred solvent is 1,2-dichloroethane.

Representative of the N,N-dimethyl amides which can be used are:
N,N-dimethylthiophene-2-carboxamide,
N,N-dimethylfuran-2-carboxamide,
N,N-dimethyl-3-methylthiophene-2-carboxamide,
N,N-dimethyl-4-methylthiophene-2-carboxamide,
N,N-dimethyl-5-methylthiophene-2-carboxamide,
N,N-dimethyl-4-chlorothiophene-2-carboxamide,
N,N-dimethyl-5-chlorothiophene-2-carboxamide,
N,N-dimethyl-3-bromothiophene-2-carboxamide,
N,N-dimethyl-5-bromothiophene-2-carboxamide,
N,N-dimethyl-3-methylfuran-2-carboxamide,
N,N-dimethyl-4-methylfuran-2-carboxamide,
N,N-dimethyl-4-chlorofuran-2-carboxamide,
N,N-dimethyl-5-chlorofuran-2-carboxamide,
N,N-dimethyl-4-bromofuran-2-carboxamide,
N,N-dimethyl-5-bromofuran-2-carboxamide,
N,N-dimethylthiophene-3-carboxamide and
N,N-dimethylfuran-3-carboxamide.

These amides can be prepared in a conventional manner from the corresponding thiophene- or furan-2-(3)-carboxylic acids i.e., by conversion into the acid chlorides followed by treatment with dimethylamine.

Upon alkaline hydrolysis of the alkyl ester group in a compound of Formula (XII) and (XIII) there are obtained the corresponding free acids of Formulas (XIIa) or (XIIIa), respectively. The hydrolysis is effected in a conventional manner, with an alkali metal hydroxide or alkali metal carbonate, e.g., sodium hydroxide, potassium hydroxide, sodium carbonate, potassium carbonate and the like, in an aqueous lower aliphatic alcohol, e.g., methanol, ethanol and the like, at a temperature of from about room temperature to reflux, for from about 30 minutes to about 4 hours, under an inert atmosphere. In the preferred embodiments, this hydrolysis is effected with aqueous methanolic potassium hydroxide, at reflux temperature for about 2 hours.

The compounds of Formulas (XIIa) and (XIIIa) can be resolved, according to methods known in the art, to obtain the corresponding individual isomers thereof. See, for example, U.S. Pat. No. 4,087,539 issued May 2, 1978 and U.S. Pat. No. 4,089,969 issued May 16, 1978.

Condensation of a compound (X) with an amide of the formula

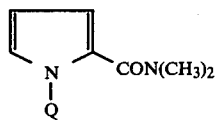

wherein Q has the above-indicated meaning, affords the corresponding alkyl 3-(2-pyrroyl)-5,6,7,8-tetrahydropyrrolo-[1,2-a]pyridine-8-carboxylates and alkyl 3-(2-pyrroyl)-6,7,8,9-tetrahydro-5H-pyrrolo[1,2-a]azepine-9-carboxylates of Formula (XIV). The reaction is conducted in an inert organic aprotic solvent and in the presence of phosphorous oxychloride, at reflux temperature for from about 15 to about 70 hours, under an inert atmosphere, followed by further reflux in the presence of sodium acetate, for from about 20 minutes to about 1 hour. Alternatively, instead of phosphorous oxychloride other acid chlorides such as phosgene or oxalyl chloride may be used.

In the preferred embodiments, this condensation is carried out by adding a solution of compound (X) in a suitable solvent to a previously refluxed mixture of 1.1 to 2 molar equivalents of both the desired amide and phosphorous oxychloride in the same solvent, refluxing the reaction mixture thus obtained for from about 17 to about 50 hours under an argon atmosphere and thereafter adding thereto from about 3 to about 10 molar equivalents of sodium acetate, followed by an additional reflux period for about 30 minutes.

Adequate solvents for this reaction are the halogenated hydrocarbons such as dichloromethane, 1,2-dichloroethane, chloroform, carbon tetrachloride and the like, dimethoxyethane and tetrahydrofuran. The preferred solvent is 1,2-dichloroethane.

Suitable amides are:
N,N-dimethylpyrrole-2-carboxamide,
N,N-dimethyl-1-methylpyrrole-2-carboxamide,
N,N-dimethyl-1-ethylpyrrole-2-carboxamide,
N,N-dimethyl-1-propylpyrrole-2-carboxamide and
N,N-dimethyl-1-butylpyrrole-2-carboxamide.

These amides can be prepared in a conventional manner from the corresponding pyrrole-2-carboxylic acids, i.e., by conversion into the acid chlorides followed by treatment with dimethylamine. The N-alkylpyrrole-2-carboxylic acids are known, or can be prepared from the corresponding N-alkylpyrroles, by the methods described by A. Treibs et al, in Liebigs Ann. Chem. 721, p. 105 (1969).

Upon alkaline hydrolysis of the alkyl ester group in a compound of Formula (XIV) there is obtained the corresponding free acid of Formula (XIVa). This hydrolysis is effected in a conventional manner, with an alkali metal hydroxide or alkali metal carbonate, e.g., sodium hydroxide, potassium hydroxide, sodium carbonate, potassium carbonate and the like, in an aqueous lower aliphatic alcohol, e.g., methanol, ethanol and the like, at a temperature of from about room temperature to reflux, for from about 15 minutes to about 2 hours, under an inert atmosphere. In the preferred embodiments, this hydrolysis is effected with aqueous methanolic potassium carbonate, at reflux temperature for about 30 minutes.

An alternative method of preparing the compound of this invention wherein R is hydrogen is set forth in Reaction Sequence 3. In this sequence an 8 or 9 nitrile is converted to the corresponding acid to give the desired compounds as follows:

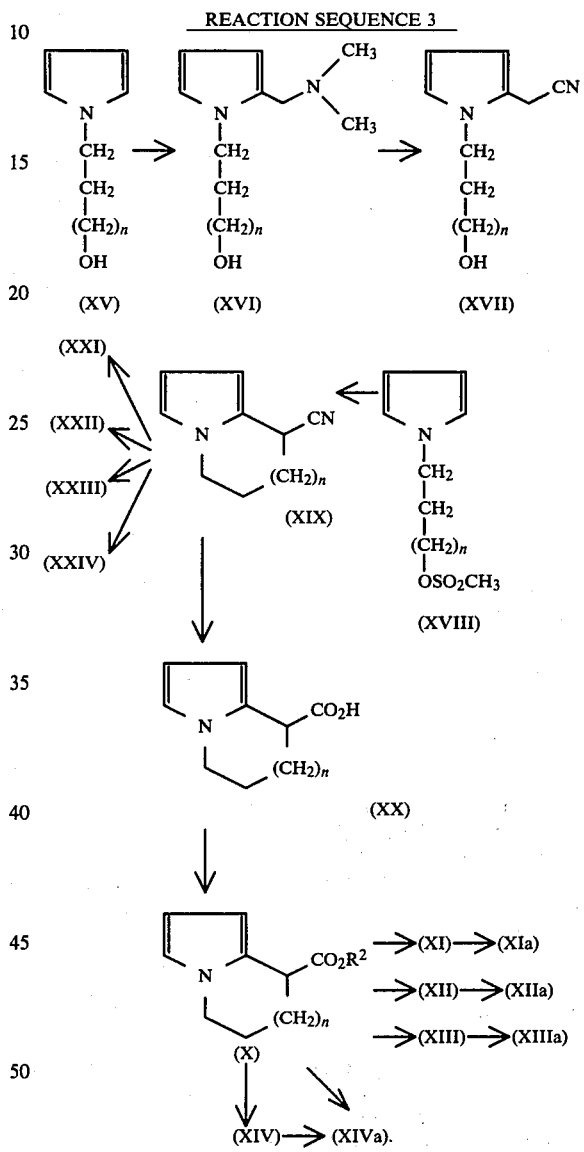

The compound represented by formula (XV) is prepared by reacting 4-aminobutanol or 3-aminopropanol with glacial acetic acid at a temperature of between 5° and 50° C. to give the corresponding acetate. This compound is then reacted with dimethoxytetrahydrofuran at a temperature sufficient for distillation to take place (about 100°-110° C. for the 4-aminobutanol acetate and about 115°-118° C. for the 3-amino-1-propanol acetate) for a period of time sufficient to give the desired pyrrole represented by formula (XV) and the corresponding acetate. After extracting the product from the reaction mixture. The product is hydrolyzed using a basic alcohol mixture such as sodium hydroxide and methanol at room temperature to give the desired product represented by formula (XV). This in turn is reacted at slightly elevated temperatures, e.g., 20°-60° C., with a solution of dimethylamine hydrochloride in aqueous formaldehyde to give 1-(4-hydroxybutyl)-2-dimethylaminomethylpyrrole (Formula (XVI) where n=2) or 1-(3-hydroxypropyl)-2-dimethylaminomethylpyrrole (Formula (XVI) where n is 1). After extraction with a suitable organic solvent such as dichloromethane and subsequent purification by evaporation and distillation, the compound represented by Formula (XVI) is then dissolved in acetone and maintained in an inert atmosphere using nitrogen or argon and a slight molar of dimethylsulfate is added to the cooled reaction mixture at such a rate that the temperature does not exceed 5° C. When addition of the dimethylsulfate is completed, the solution is stirred at room temperature and a solution of sodium cyanide in water is added. The resulting reaction mixture is heated to a temperature which is sufficient to effect distillation generally about 90°-100° C. and the distillate is collected. The reaction mixture is heated at a gentle reflux for a suitable period of time, generally less than 2 hours, preferably about ½ hour and water is added to the mixture. After extracting, drying and purification by column chromatography, a nitrile represented by formula (XVII) is obtained, namely, 1-(4-hydroxy)butylpyrrol-2-acetonitrile (Formula (XVII) where n is 2) or 1-(3-hydroxypropyl)pyrrol-2-acetonitrile (Formula (XVII) where n is 1).

The compound of formula (XVII) is then converted to the corresponding 1-(4-methanesulfonyloxy)butylpyrrol-2-acetonitrile or 1-(3-methanesulfonyloxy)propylpyrrol-2-acetonitrile by following procedures which are well known in the art and discussed hereinbefore in the discussion of the preparation of the compound represented by Formula (V) in Reaction Sequence 1. The methane sulfonate represented by Formula (XVIII) is converted to the corresponding 8-cyano-5,6,7,8-tetrahydropyrrolo-(1,2-a)pyridine (Formula (XIX) where n equals 1) or 9-cyano-5,6,7,8-tetrahydro-9H-pyrrolo[1,2-a]azepine (Formula (XIX) where n is 2) according to procedures set forth hereinbefore in the discussion of Reaction Sequence 1 in conversion of the compound of Formula (V) to the compound of Formula (VII). In this reaction sequence the key intermediate is the nitrile represented by Formula (XIX). This nitrile can be converted into the acid represented by Formula (XX) by reacting with aqueous sodium or potassium hydroxide in ethylene glycol at elevated temperatures of up to 120° C. for a time sufficient for the reaction to take place, generally less than about 5 hours. Extracting the reaction mixture with a suitable organic solvent and bringing the aqueous phase to an acid pH using concentrated hydrochloric acid and extracting from water results in the acid represented by Formula (XI). This in turn can be converted to products of the invention as previously discussed in the discussion of Reaction Sequence 1.

The intermediate nitrile of Formula (XIX) can be converted into the nitrile of Formula XXI through XXIV according to Reaction Sequence 4 using reaction conditions discussed hereinbefore in the conversion of the compound of Formulas (X) to (XI) through (XIV). These in turn can be converted to the compounds of the invention by converting the nitrile moiety to an acid as discussed hereinbefore.

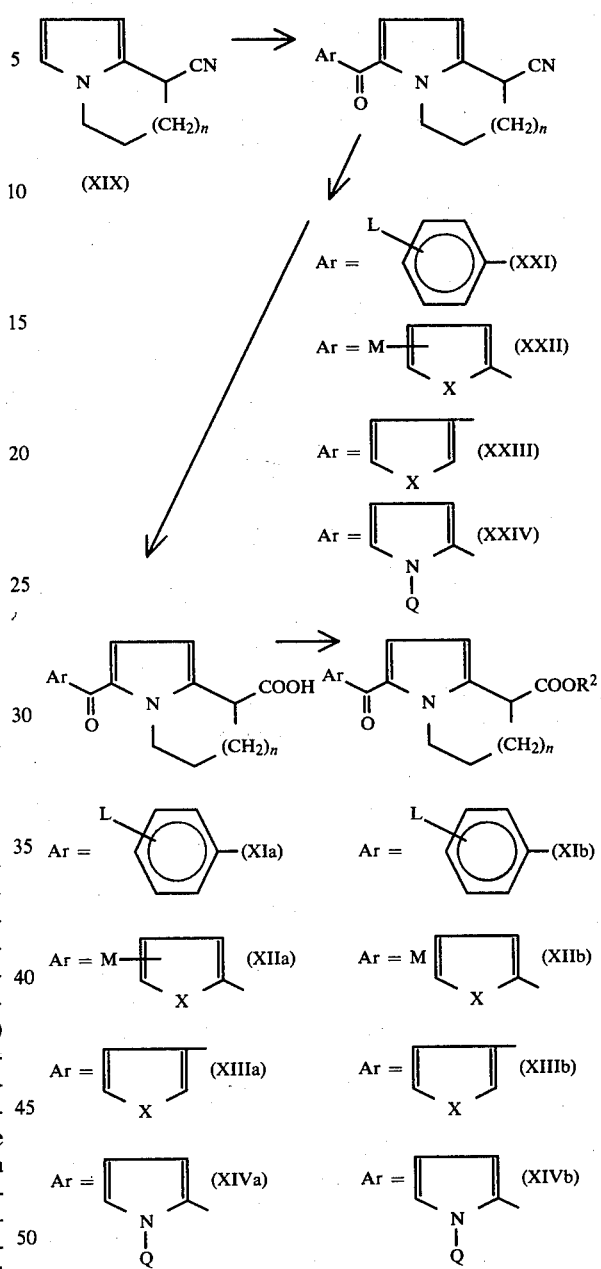

The compounds of Formula (XIVa) can be resolved, according to methods known in the art, to obtain the corresponding individual isomers thereof. See, for example, U.S. Pat. No. 4,087,539 issued May 2, 1978 and U.S. Pat. No. 4,089,969 issued May 16, 1978.

The free acids of Formulas (XIa), (XIIa), (XIIIa) and (XIVa) can be converted into other alkyl esters having from 1 to 12 carbon atoms by conventional methods, e.g., by treatment with (a) the alcohol corresponding to the desired ester in the presence of a strong mineral acid, (b) an etheral diazoalkane or (c) the desired alkyl iodide in the presence of lithium carbonate. These conversions take place at temperatures of about 0°-50° C., preferably at ambient temperature.

The salt derivatives of the compounds of Formulas (XIa), (XIIa), (XIIIa) and (XIVa) are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° to about 100° C., preferably at room temperature. Typical inert, water-miscible organic solvents include methanol, ethanol, isopropanol, butanol, acetone, dioxane or tetrahydrofuran. The molar ratio of compounds of Formulas (XIa), (XIIa), (XIIIa) and (XIVa) to base used are chosen to provide the ratio desired for any particular salt. For preparing, for example, the calcium salts or magnesium salts of the compounds of Formulas (XIa), (XIIa), (XIIIa) and (XIVa) the free acid starting material can be treated with at least one-half molar equivalent of pharmaceutically acceptable base to yield a neutral salt. When the aluminum salts of the compounds of Formulas (XIa), (XIIa), (XIIIa) and (XIVa) are prepared at least one-third molar equivalent of the pharmaceutically acceptable base are employed if a neutral salt product is desired.

In the preferred procedure, the calcium salts and magnesium salts of the compounds of Formulas (XIa), (XIIa), (XIIIa) and (XIVa) can be prepared by treating the corresponding sodium or potassium salts thereof with at least one-half molar equivalent of calcium chloride or magnesium chloride, respectively, in an aqueous solution, alone or in combination with an inert water-miscible organic solvent, at a temperature of from about 20° to about 100° C. Preferably, the aluminum salts of the compounds hereof, can be prepared by treating the corresponding free acids with at least one-third molar equivalent of an aluminum alkoxide, such as aluminum triethoxide, aluminum tripropoxide and the like, in a hydrocarbon solvent, such as benzene, xylene, cyclohexane and the like, at a temperature of from about 20° C. to about 115° C. Similar procedures can be used to prepare salts of inorganic bases which are not sufficiently soluble for easy reaction.

An alternative, and preferred, method for preparing the alkylsulfinylbenzoyl- and alkylsulfonylbenzoyl compounds of this invention is shown in Reaction Sequence 5.

REACTION SEQUENCE 5

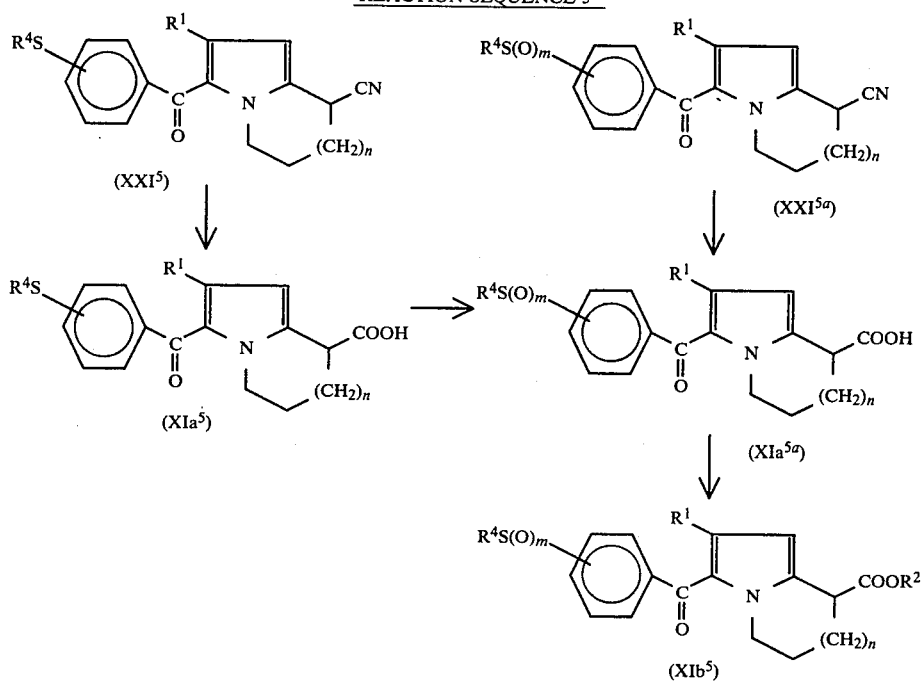

In this reaction sequence, the 3-alkylthiobenzoyl-8-cyano-5,6,7,8-tetrahydro-5H-pyrrolo[1,2-a]pyridine or the corresponding azepine is converted to the corresponding alkylsulfinylbenzoyl compound or the alkylsulfonylbenzoyl compound by a suitable oxidation method. The oxidation of the alkylthio moiety may take place before or after the conversion of the cyano compound to the carboxylic acid. The conversion of the cyano compound to the carboxylic acid is performed in essentially the same manner as discussed hereinbefore. The alkylthio moiety, can be oxidized using any suitable method known in the art. For example, the alkylthiobenzoyl compound can be converted to the corresponding alkylsulfinylbenzoyl compound by treatment with an appropriate oxidizing agent at low temperatures of at about −10° to about 20°, preferably about 0° C. Suitable oxidizing agents include sodium periodate, m-chloroperbenzoic acid, ceric ammonium nitrate, hydrogen peroxide containing selenium dioxide, and the like. Generally, molar quantity of the oxidizing agent which is equal to the molar quantity of the alkylthiobenzoyl compound is employed. Usually the reaction is completed within 24 hours.

To convert the alkylthiobenzoyl compound to the corresponding alkylsulfonylbenzoyl compound oxidizing agents are employed such as meta-chloroperbenzoic acid, perphthalic acid, peracetic acid, and the like. This reaction takes place at a temperature of about −10 to about +10, preferably about −5° to about 0° C. In general, a molar quantity of the oxidizing agent which is equal to at least twice the molar quantity of the alkylthiobenzoyl compound is used. Preferably an alkylthiobenzoyl compound is converted to a alkylsulfonylbenzoyl compound before the cyano group is converted to the carboxyl groups, whereas in preparing the alkylsulfinyl compounds, it is preferred that the cyano moiety is first hydrolyzed to the carboxylic acid.

It is to be understood that isolation of the compounds described herein can be effected, if desired, by any suitable separation or purification procedure, such as, for example, extraction, filtration, evaporation, distillation, crystallization, thin-layer chromatography or column chromatography, high pressure liquid chromatography (HPLC) or a combination of these procedures. Illustrations of suitable separation and isolation procedures for other compounds are available in the art. For example, see U.S. Pat. Nos. 4,087,539; 4,089,969; and 4,097,579. However, other equivalent separation or isolation procedures could, of course, also be used.

UTILITY AND ADMINISTRATION

The compounds of Formulas (XIa), (XIIa), (XIIIa) and (XIVa) and the pharmaceutically acceptable non-toxic esters and salts thereof, are useful as anti-inflammatory agents, analgetic agents, antipyretic platelet aggregation inhibitors, fibrinolytic agents, and as smooth muscle relaxants. These compounds can be used both prophylactically and therapeutically.

The compositions containing these compounds are thus useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Compositions containing these compounds are, thus, also useful in the treatment of disorders and conditions in which it is desirable to control or inhibit blood clotting. Such disorders include, for example, thrombosis or thrombophlebitis; such conditions include, for example, post surgical maintenance.

Administration of the active compounds of Formulas (XIa), (XIIa), (XIIIa) and (XIVa) and the pharmaceutically acceptable, non-toxic esters and salts thereof, in an appropriate pharmaceutical composition can be via any of the accepted modes of administration of agents for the treatment of inflammation, pain or pyrexia, or the prophylaxis thereof, or for the regulation of blood clotting. Thus, administration can be for example, orally or parenterally, preferably orally, in the form of solid, semi-solid or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of Formulas (XIa), (XIIa), (XIIIa) and (XIVa) and the pharmaceutically acceptable, non-toxic esters and salts thereof, and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 25 mg. to 500 mg. of the active compound of Formulas (XIa), (XIIa), (XIIIa) and (XIVa) and the pharmaceutically acceptable, non-toxic esters and salts thereof is used, for use as an anti-inflammatory, or 50 mg to 2000 mg for the platelet inhibition function. Most conditions involving inflammation respond to treatment comprising a dosage level of the order of 0.5 mg. to 10 mg. per kilogram of body weight per day. Most conditions requiring treatment with a platelet aggregation inhibitor respond to a dosage level of 1 mg/kg to 100 mg/kg per day.

For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Generally, such compositions will contain about 1% to about 99% by weight of the pharmaceutically active compound of this invention and 99% to 1% by weight of suitable pharmaceutical excipients. Preferably, the composition will be 5% to 90% by weight of a pharmaceutically active compound, with the rest being suitable pharmaceutical excipients.

The active compounds of Formulas (XIa), (XIIa), (XIIIa) and (XIVa) and the pharmaceutically acceptable, non-toxic esters and salts thereof, may be formulated into a suppository using, for example, polyalkylene glycols, for example, polypropylene glycol, as the carrier. Liquid pharmaceutically administerable compositions can, for example, be prepared by dissolving, dispersing, etc. an active compound, as described above, and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pa., 14th. Edition, 1970. The composition to be administered will, in any event, contain a quantity of the active compound(s) in a pharmaceutically effective amount for relief of the particular condition being treated in accordance with the teachings of this invention.

The compounds of Formulas (XIa), (XIIa), (XIIIa) and (XIVa) and the non-toxic, pharmaceutically acceptable, esters and salts thereof, described above, are also uterine smooth muscle relaxants and thus are useful as agents for maintaining the pregnancy of pregnant mammals, for the benefit of the mother and/or fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formulas (XIa), (XIIa), (XIIIa) and (XIVa) and the pharmaceutically acceptable, non-toxic esters and salts thereof, are used as agents for delaying the onset of, or for postponing, parturition. As used in this application, the phrase "to delay the onset of parturition" is intended to cover that delay in partuirtion caused by the administration of the compounds of Formulas (XIa), (XIIa), (XIIIa) and (XIVa) and the pharmaceutically acceptable, non-toxic esters and salts thereof, at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formulas (XIa), (XIIa), (XIIIa) and (XIVa) and the pharmaceutically acceptable, non-toxic esters and salts thereof after uterine muscle contractions have begun. The condition of the patient, including the time within the gestation period when the contractions have begun, the severity of the contractions and how long the contractions have taken place will affect the results achieved with the administration of the compounds hereof. For example, the effect can be to reduce the intensity and/or the duration of the contractions (the actual act of parturition being "prolonged"), or to stop the contractions altogether. In either case, the effect will be to prolong the gestation period although, depending upon the conditions of the patient as described above, the effect may either by slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formulas (XIa), (XIIa), (XIIIa) and (XIVa) and the pharmaceutically acceptable, non-toxic esters and salts thereof, as a uterine smooth muscle relaxant as set forth herein should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formulas (XIa), (XIIa), (XIIIa) and (XIVa) and the pharmaceutically acceptable, non-toxic esters and salts thereof, or a pharmaceutical composition containing same, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, gelatin, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pennsylvania, 14th Edition, 1970. The composition or formulation to be administered will, in any event, contain a quantity of the active compound(s) in an amount effective to delay the onset of parturition or to postpone parturition if uterine contractions have already begun. Generally a daily dose of from 0.5 mg. to about 25 mg. of the active compound per kilogram of body weight will be administered, with administration being a single daily dose or up to three or four smaller dosages regularly given throughout the day. The amount of active compound administered will, of course, depend on its relative activity.

The following Preparations and Examples illustrate the invention but are not intended to limit its scope. The abbreviation t.l.c. refers to thin-layer chromatography and all mixtures ratios used with regard to liquids refer

PREPARATION 1

A mixture of 23 g. of 4-chlorothiophene-2-carboxylic acid (J. Iriarte et al., J. Heterocyclic Chem. 13, 393) and 80 ml. of thionyl chloride is heated to reflux, under anhydrous conditions for 4 hours. The excess thionyl chloride is eliminated and the residue distilled under reduced pressure (60° C./2 mm), to afford 18 g. of 4-chlorothiophene-2-carboxylic acid chloride.

A solution of 10.5 g. of 4-chlorothiophene-2-carboxylic acid chloride in 500 ml. of anhydrous benzene is cooled in an ice water bath and dimethylamine is slowly bubbled through the solution for 30 minutes. The ice water bath is removed, maintaining the stream of dimethylamine for 15 additional minutes. The reaction mixture is then diluted with 100 ml. of 10% sodium chloride solution and stirred for 5 minutes at room temperature, the organic phase is separated, washed with 10% hydrochloric acid, saturated sodium bicarbonate solution and saturated sodium chloride solution, dried over sodium sulfate and evaporated to dryness under reduced pressure, to produce N,N-dimethyl-4-chlorothiophene-2-carboxamide.

In a similar manner the thiophene and furan-2-carboxylic acids listed below under I are converted into the N,N-dimethyl amides listed under II:

| I | II |
|---|---|
| thiophene-2-carboxylic acid | N,N—dimethylthiophene-2-carboxamide |
| 3-methylthiophene-2-carboxylic acid | N,N—dimethyl-3-methylthiophene-2-carboxamide |
| 4-methylthiophene-2-carboxylic acid | N,N—dimethyl-4-methylthiophene-2-carboxamide |
| 5-methylthiophene-2-carboxylic acid | N,N—dimethyl-5-methylthiophene-2-carboxamide |
| 3-chlorothiophene-2-carboxylic acid | N,N—dimethyl-3-chlorothiophene-2-carboxamide |
| 5-chlorothiophene-2-carboxylic acid | N,N—dimethyl-5-chlorothiophene-2-carboxamide |
| 3-bromothiophene-2-carboxylic acid | N,N—dimethyl-3-bromothiophene-2-carboxamide |
| 4-bromothiophene-2-carboxylic acid | N,N—dimethyl-4-bromothiophene-2-carboxamide |
| 5-bromothiphene-2-carboxylic acid | N,N—dimethyl-5-bromothiophene-2-carboxamide |
| furan-2-carboxylic acid | N,N—dimethylfuran-2-carboxamide |
| 3-methylfuran-2-carboxylic acid | N,N—dimethyl-3-methylfuran-2-carboxamide |
| 4-methylfuran-2-carboxylic acid | N,N—dimethyl-4-methylfuran-2-carboxamide |
| 5-methylfuran-2-carboxylic acid | N,N—dimethyl-5-methylfuran-2-carboxamide |
| 3-chlorofuran-2-carboxylic acid | N,N—dimethyl-3-chlorofuran-2-carboxamide |
| 4-chlorofuran-2-carboxylic acid | N,N—dimethyl-4-chlorofuran-2-carboxamide |
| 5-chlorofuran-2-carboxylic acid | N,N—dimethyl-5-chlorofuran-2-carboxamide |
| 4-bromofuran-2-carboxylic acid | N,N—dimethyl-4-bromofuran-2-carboxamide |
| 5-bromofuran-2-carboxylic acid | N,N—dimethyl-5-bromofuran-2-carboxamide |
| thiophene-3-carboxylic acid | N,N—dimethylthiophene-3-carboxamide |
| furan-3-carboxylic acid | N,N—dimethylfuran-3-carboxamide. |

PREPARATION 2

A. A solution of 10 g. of N-methylpyrrole-2-carboxylic acid in 20 ml. of anhydrous benzene is treated with 11.5 ml. of thionyl chloride, and the reaction mixture is refluxed under anhydrous conditions for 16 hours. The benzene and excess thionyl chloride are distilled off and the residue is distilled under reduced pressure, to afford 7.88 g. of N-methylpyrrole-2-carbonyl chloride, b.p. 79°–84° C./5 mm.

B. Under an atmosphere of argon there are mixed 7.88 g. of N-methylpyrrole-2-carbonyl chloride and 400 ml. of anhydrous benzene. The solution is cooled to 5° C. in an ice-water bath and anhydrous dimethylamine is slowly bubbled through the solution. The temperature of the reaction mixture is allowed to rise to room temperature and dimethylamine is bubbled for an additional 5 minute period. The reaction mixture is then diluted with water, the organic phase is separated and washed with 50 ml. of 10% aqueous hydrochloric acid, 50 ml. of saturated sodium bicarbonate solution and twice with 50 ml. of saturated sodium chloride solution. The organic extract is dried with anhydrous sodium sulfate, decolorized with charcoal and evaporated to dryness under reduced pressure, thus obtaining 8 g. of N,N-dimethyl-1-methylpyrrole-2-carboxamide, as an oil, which has the following physical constants:

U.V. $\lambda_{max}^{MeOH}$ 221, 226 nm ($\epsilon$ 6900,9300); I.R. $_{max}^{CHCl_3}$ 1610 cm$^{-1}$; N.M.R. TMS$^{CDCl_3}$ 3.08 (s, 6H), 3.70 (s, 3H), 5.87–6.05(m, 1H), 6.17–6.35(m, 1H), 6.47–6.65 ppm(m, 1-H).

By repeating the above procedures, using N-ethylpyrrole-2-carboxylic acid, N-propylpyrrole-2-carboxylic acid and N-butylpyrrole-2-carboxylic acid as starting materials there are respectively obtained:
N,N-dimethyl-1-ethylpyrrole-2-carboxamide,
N,N-dimethyl-1-propylpyrrole-2-carboxamide and
N,N-dimethyl-1-butyl-pyrrole-2-carboxamide.

N-propylpyrrole-2-carboxylic acid and N-butylpyrrole-2-carboxylic acid are prepared by reaction of N-propylpyrrole and N-butylpyrrole with trichloroacetyl chloride, to give the corresponding 2-trichloroacetyl pyrroles, followed by base treatment, as described by A. Treibs et al., in Liebigs Ann. Chem. 721, p. 105 (1969).

Likewise, by the method of part B of this Preparation, pyrrole-2-carbonyl chloride, obtained as described by R. J. Boatman et al., in J. Org. Chem. 41, p. 3050 (1976), is converted into N,N-dimethylpyrrole-2-carbox-amide, m.p. 100.5°–102° C.

EXAMPLE 1

A 250 ml. 3-necked round bottomed flask containing a magnetic stirring bar and fitted with a calcium chloride filled drying tube is connected directly (via one of the outer necks) by means of a receiver adapter and short (3") water condenser to an acetal pyrolysis apparatus. This latter apparatus consists of a 100 ml. round bottomed flask [previously charged with 48 g. of oxalic acid dihydrate and 19.7 ml of bromoacetaldehye dimethyl acetal, prepared from vinyl acetate, as described by P. Z. Bedoukian, J. Am. Chem. Soc. 66, 651 (1944)], topped with a 6" Vigreux column, bearing a thermometer, connected to the above mentioned condenser.

The 3-necked flask is charged with 2.5 g. of propanolamine (I) containing activated molecular sieves (Type 3A) cooled in an ice bath at 0°–10° C. and treated dropwise, with stirring, with 5.27 g. of dimethyl 1,3-acetone-dicarboxylate (II) and stirred for 2 hours to form methyl 3-carbomethoxymethyl-3-(3′-hydroxypropyl)amino acrylate (III). When the reaction is completed, 70 ml. of dry acetonitrile are added. The pyrolysis part of the apparatus is placed in an oil bath and the temperature thereof is raised to 150°–160° C. The bromoacetaldehyde solution which forms is distilled (b.p. 80–83 mm) directly into the magnetically stirred solution of the amino acrylate (III) and stirred for 16 hours. When the distillation temperature drops below 80° C., the pyrolysis apparatus is disconnected and replaced by a reflux condenser fitted with a drying tube containing calcium chloride. The soltuion is heated at reflux temperature for 1 hour, the solvent is removed under reduced pressure and then 200 ml. of methanol and 20 g. silica gel are added to the residue. This mixture is evaporated to dryness in vacuum and placed on top of a column of 200 g. of silica gel packed in hexane. The column is then eluted with 3 liters of hexane, 4 liters of hexane:ethyl acetate (80:20), 6 liters of hexane-ether (50:50) and 1 liter hexane:ether (20:80). Fractions 1–41 contain less polar impurities and dimethyl 1,3-acetonedicarboxylate; fractions 42–109 from 7 reactions were collected and the solvent removed to give 76 grams of crude product. Crystallization from a dichloromethane-hexane mixture gave 20.3 grams of methyl N-(3-hydroxypropyl)-3-carbo-methoxypyrrole-2-acetate (IV, R=H, n=1), m.p. 52° C.

In like manner, by substituting butanolamine for propanolamine and following the procedures of this example there is obtained methyl N-(4-hydroxybutyl)-3-carbo-methoxypyrrole-2-acetate (IV, R=H, N=2).

EXAMPLE 2

To a stirred solution of 25.0 g. of methyl N-(3-hydroxypropyl)-3-carbomethoxypyrrole-2-acetate in 400 ml. of dry dichloromethane cooled to 0° C., are added 10 ml. of triethylamine and thereafter, in a dropwise fashion, 7.0 ml. of methanesulfonyl chloride, maintaining the temperature of the reaction mixture at about 0° C. The course of the reaction is followed by t.l.c. analysis using chloroform:acetone (90:10). When the reaction appears to be complete (about 15 minutes after the addition of the methanesulfonyl chloride is terminated) 10 ml of water is slowly added. The organic phase is separated, washed with water (3×30 ml.), dried over magnesium sulfate and evaporated under reduced pressure. The residue is cooled in a methanol-dry ice bath and the minimum amount of methanol is added to give a crystalline residue. Crystallization of the residue from dichloromethane-ether affords 21.5–22.5 g. of methyl N-(3-methanesulfonyloxypropyl)-3-carbomethoxypyrrol-2-acetate (V, R=H, n=1), m.p. 53°–54° C.

In like manner, by substituting methyl N-(4-hydroxybutyl)-3-carbomethoxypyrrole-2-acetate for methyl N-(3-hydroxypropyl)-3-carbomethoxypyrrole-2-acetate there is obtained methyl N-(4-methanesulfonyloxybutyl)-3-carbomethoxypyrrole-2-acetate (V, R=H, n=2).

EXAMPLE 3

A solution of 24.48 g. of methyl N-(3-mesyloxypropyl)-3-carbomethoxypyrrole-2-acetate and 25.0 g. of sodium iodide in 500 ml. of acetonitrile is refluxed for 25 hours. The extract is washed with water, dried over sodium sulfate and evaporated to dryness under reduced pressure. The residue is purified by column chromatography on silica gel, the column being eluted with 1 l. hexane, 1 l. hexane-ethyl acetate (90:10), 1 l. hexaneEtAc (80:20), 1 . hexane-EtAc (70:30) and 1 l. hexaneEtAc (60:40). The desired material is in the 60:40 fraction. After removing the solvent and recrystallizing from dichloromethane/hexane, methyl N-(3-iodopropyl)-3-carbomethoxypyrrole-2-acetate (VI, R=H, n=1), m.p. 64°–65° C., is obtained.

In like manner, by substituting methyl N-(4-mesyloxybutyl)-3-carbomethoxypyrrole-2-acetate for methyl N-(3-mesyloxypropyl)-3-carbomethoxypyrrole-2-acetate there is obtained methyl-(4-iodobutyl)-3-carbomethoxypyrrole-2-acetate (VI, R=H, n=2).

EXAMPLE 4

A solution of 17 g. of methyl N-(3-iodopropyl)-3-carbomethoxypyrrole-2-acetate is added portionwise over an hour to a stirred suspension of 52.7 g. (99%) NaH in 300 ml. dry dimethylformamide at 0° C. and maintained in nitrogen. The temperature is allowed to reach 20° and stirring is continued for 1 hour. The reaction mixture is diluted with saturated NaCl and extracted with benzene 4 times. The combined extracts are washed with water, dried over sodium sulfate and evaporated to dryness in vacuo. Recrystallization of the residue using benzene-hexane affords dimethyl 5,6,7,8-tetrahydropyrrolo[1,2-a]-pyridine-1,8-dicarboxylate (VII, R=H, n=1) m.p. 108° C.

A solution of 8.6 g. of dimethyl 5,6,7,8-tetrahydropyrrolo[1,2-a]pyridine-1,8-dicarboxylate in 100 ml. of methanol is treated with a solution of 9.0 g. of potassium hydroxide in 100 ml. of water, and the reaction mixture is refluxed for 24 hours. The cooled solution is evaporated to dryness at a temperature of 30° C. and the residue is dissolved in the minimum amount of saturated sodium chloride solution. The resultant solution is acidified with concentrated hydrochloric acid and the precipitated solid is collected by filtration, washed with water and dried in vacuo. The mother liquor is extracted with ethyl acetate 3 times and the combined extracts are dried over magnesium sulfate and evaporated to dryness under reduced pressure and recrystallization of the combined residues from methanol yields 5,6,7,8-tetrahydropyrrolo[1,2-a]pyridine-1,8-dicarboxylic acid (VIII, R=H, n=1), m.p. 236°–237° C.

In like manner, by substituting methyl N-(4-iodobutyl)-3-carbomethoxypyrrole-2-acetate for methyl N-(3-iodopropyl)-3-carbomethoxypyrrole-2-acetate and following the procedures of this example there are obtained seriatim dimethyl 6,7,8,9-tetrahydro-5H-pyrrolo[1,2-a]azepine-1,9-dicarboxylate (VII, R=H, n=2) and 6,7,8,9-tetrahydro-5H-pyrrolo[1,2-a]azepine-1,9-dicarboxylic acid (VIII, R=H, n=2).

EXAMPLE 5

A solution of 7.2 g. of 5,6,7,8-tetrahydropyrrolo[1,2-a]pyridine-1,8-dicarboxylic acid in 300 ml. of isopropanol, cooled in an ice bath is saturated with gaseous hydrogen chloride, maintaining the temperature of the reaction mixture 0° C. The ice bath is then removed and the reaction mixture is kept at ambient temperature for 5 days, at which time nitrogen is passed through the reaction mixture to remove the HCl. The solvent is removed under reduced pressure, and sodium carbonate is added and the mixture is treated with benzene. The aqueous phase is made acidic with hydrochloric acid and the product is extracted with ethyl acetate. The extract is dried over sodium sulfate and evaporated in vacuo to give a residue n=1, which upon crystallization from acetone/hexane acetate yields isopropyl 5,6,7,8-tetrahydropyrrolo[1,2-a]pyridine-8-carboxylate-1-carboxylic acid (IX, R=H, R$^2$=iC$_3$H$_7$, n=1), m.p. 165° C.

In like manner, substituting 6,7,8,9-tetrahydro-5H-pyrrolo[1,2-a]azepine-1,9-dicarboxylic acid for 5,6,7,8-tetrahydropyrrolo[1,2-a]-pyridine-1,8-dicarboxylic acid there is obtained isopropyl 6,7,8,9-tetrahydro-5H-pyrrolo[1,2-a]azepine-9-carboxylate-1-carboxylic acid (IX, R=H, R$^2$=iC$_3$H$_7$, n=2).

In a similar manner but substituting methanol, ethanol, n-propanol and n-butanol for isopropanol in the above procedure there are respectively obtained:

methyl 5,6,7,8-tetrahydropyrrolo[1,2-a]pyridine-8-carboxylate-1-carboxylic acid, ethyl 5,6,7,8-tetrahydropyrrolo[1,2-a]pyridine-8-carboxylate-1-carboxylic acid, n-propyl 5,6,7,8-tetrahydropyrrolo[1,2-a]pyridine-8-carboxylate-1-carboxylic acid, n-butyl 5,6,7,8-tetrahydropyrrolo[1,2-a]pyridine-8-carboxylate-1-carboxylic acid, and methyl 6,7,8,9-tetrahydro-5H-pyrrolo[1,2-a]azepine-9-carboxylate-1-carboxylic acid, ethyl 6,7,8,9-tetrahydro-5H-pyrrolo[1,2-a]azepine-9-carboxylate-1-carboxylic acid, n-propyl 6,7,8,9-tetrahydro-5H-pyrrolo[1,2-a]azepine-9-carboxylate-1-carboxylic acid, and n-butyl 6,7,8,9-tetrahydro-5H-pyrrolo[1,2-a]azepine-9-carboxylate-1-carboxylic acid.

EXAMPLE 6

500 Mg. of isopropyl 5,6,7,8-tetrahydropyrrolo[1,2-a]pyridine-8-carboxylate-1-carboxylic acid is heated to 230°–245° C. in a dry 10 ml. round bottomed flask, distilling directly the reaction product from the reaction vessel. In this manner there is obtained isopropyl 5,6,7,8-tetrahydropyrrolo[1,2-a]pyridine-8-carboxylate (X, R=H, R$^2$=iC$_3$H$_7$, n=1), a light yellow oil, having the following physical constants:

```
uv 222 nm (ε 5500):
ir (CHCl₃)
   1730 cm⁻¹;
nmr CDCl₃
   1.26 (d, 6H, J ≈ 6 Hz)
   2.05 (brm, 4H)
   3.86 (brm, 3H)
   4.96 (m, 1H J ≈ 6 Hz)
   5.97 (m, 2H)
   6.42 (m, 1H)
   ms 207 (M⁺).
```

In like manner, substituting isopropyl 6,7,8,9-tetrahydro-5H-pyrrolo[1,2-a]azepine-9-carboxylate-1-carboxylic acid for isopropyl 5,6,7,8-tetrahydropyrrolo[1,2-a]pyridine-8-carboxylate-1-carboxylic acid there is obtained isopropyl 6,7,8,9-tetrahydro-5H-pyrrolo[1,2-a]azepine-9-carboxylate (X, R=H, R$^2$=iC$_3$H, n=2). Similarly, the methyl, ethyl, propyl and butyl esters of 5,6,7,8-tetrahydropyrrolo[1,2-a]pyridine-8-carboxylate and 6,7,8,9-tetrahydro-5H-pyrrolo[1,2-a]azepine-9-carboxylate are prepared by starting with the corresponding 1-carboxylic acids of Example 5.

EXAMPLE 7

A solution of 758 mg. of N,N-dimethyl-4-fluorobenzamide and 0.44 ml. of phosphorous oxychloride in 50 ml. of 1,2-dichloroethane is refluxed for one hour. To this solution is added a solution of 500 mg. of isopropyl 5,6,7,8-tetrahydropyrrolo[1,2-a]pyridine-8-carboxylate in 10 ml. 1,2-dichloroethane. The reaction mixture is refluxed for 3 hours. A solution of 3.3 g. sodium acetate trihydrate in 9 ml water is added and refluxed for a further 10 hours. The organic phase is separated, washed with saturated sodium chloride solution, dried over sodium sulfate and evaporated to dryness. The residue is purified by preparative t.l.c. using hexane:ethyl acetate (90:10). Crystallization from dichloromethane-hexane yields isopropyl 3-p-fluorobenzoyl-5,6,7,8-tetrahydropyrrolo[1,2-a]pyridine-8-carboxylate (XI, R=H, L=p-F, R$^2$=iC$_3$H$_7$, n=1), m.p. 92° C.

In like manner, substituting isopropyl 6,7,8,9-tetrahydro-5H-pyrrolo[1,2-a]azepine-9-carboxylate for isopropyl 5,6,7,8-tetrahydropyrrolo[1,2-a]pyridine-8-carboxylate there is obtained isopropyl 3-p-fluorobenzoyl-6,7,8,9-tetrahydro-5H-pyrrolo[1,2-a]azepine-9-carboxylate (XI, R=H, L=i-CH$_3$, R$^2$=1C$_3$H$_7$, n=2).

EXAMPLE 8

A solution of 180 mg. of isopropyl 3-p-fluorobenzoyl-5,6,7,8-tetrahydropyrrolo[1,2-a]pyridine-8-carboxylate in 5 ml. of methanol is treated with a solution of 200 mg. of potassium carbonate in 1.5 ml. of water. The reaction mixture is refluxed under a nitrogen atmosphere for 24 hours, cooled, and evaporated to dryness. The residue is taken up in water and the resultant mixture extracted with ethyl acetate to remove the neutral impurities. The aqueous phase is made acidic with concentrated hydrochloric acid and the product is extracted with ethyl acetate. The extract is washed with sodium chloride, dried over sodium sulfate and evaporated to dryness under reduced pressure. Crystallization of the residue from acetone hexane affords 3-p-fluorobenzoyl-5,6,7,8-tetrahydropyrrolo[1,2-a]pyridine-8-carboxylic acid (XIa, R=H, L=p-F, n=1), m.p. 164° C.

In like manner, substituting isopropyl-3-p-fluorobenzoyl-6,7,8,9-tetrahydro-5H-pyrrolo[1,2-a]azepine-9-carboxylate for isopropyl 3-p-fuorobenzoyl-5,6,7,8-tetrahydropyrrolo[1,2-a]pyridine-8-carboxylate there is obtained 3-p-fluorobenzoyl-6,7,8,9-tetrahydro-5H-pyrrolo[1,2-a]azepine-9-carboxylic acid (XIa, R=H, L=p-F, n=2).

EXAMPLE 9

A solution of isopropyl 3-p-fluorobenzoyl-5,6,7,8-tetrahydropyrrolo[1,2-a]pyridine-8-carboxylate in methanol is treated under an atmosphere of nitrogen with a solution of sodium hydroxide in water, maintaining the reaction mixture at room temperature for 1.5 hours. The methanol is then removed under reduced pressure and the basic solution which remains is diluted with water and extracted with ether to remove any unsaponifiable product. The aqueous solution is acidified with 10% hydrochloric acid and extracted three times with ethyl acetate. The combined extracts are dried and evaporated to dryness under reduced pressure, and the residue crystallized from ethyl acetate-hexane, to give 3-p-fluorobenzoyl-5,6,7,8-tetrahydropyrrolo[1,2-a]pyridine-8-carboxylic acid, identical to the product obtained in Example 8.

In like manner, substituting isopropyl 3-p-fluorobenzoyl-6,7,8,9-tetrahydro-5H-pyrrolo[1,2-a]azepine-9-carboxylate for isopropyl 5-p-fluorobenzoyl-5,6,7,8-tetrahydropyrrolo[1,2-a]pyridine-8-carboxylic acid there is obtained 5-p-fluorobenzoyl-6,7,8,9-tetrahydro-5H-pyrrolo[1,2-a]azepine-9-carboxylic acid.

EXAMPLE 10

By following the methods of Example 6 the remaining compounds obtained in Example 5 are coverted respectively into:
methyl 5,6,7,8-tetrahydropyrrolo[1,2-a]pyridine-8-carboxylate,
ethyl 5,6,7,8-tetrahydropyrrolo[1,2-a]pyridine-8-carboxylate,
propyl 5,6,7,8-tetrahydropyrrolo[1,2-a]pyridine-8-carboxylate,
butyl 5,6,7,8-tetrahydropyrrolo[1,2-a]pyridine-8-carboxylate, and
methyl 6,7,8,9-tetrahydro-5H-pyrrolo[1,2-a]azepine-9-carboxylate,
ethyl 6,7,8,9-tetrahydro-5H-pyrrolo[1,2-a]azepine-9-carboxylate,
propyl 6,7,8,9-tetrahydro-5H-pyrrolo[1,2-a]azepine-9-carboxylate, and
butyl 6,7,8,9-tetrahydro-5H-pyrrolo[1,2-a]azepine-9-carboxylate.

Upon condensation of these compounds with N,N-dimethyl-p-fluorobenzamide, in accordance with the method of Example 8 there are respectively obtained:
methyl 3-p-fluorobenzoyl-5,6,7,8-tetrahydropyrrolo[1,2-a]pyridine-8-carboxylate,
ethyl 3-p-fluorobenzoyl-5,6,7,8-tetrahydropyrrolo[1,2-a]pyridine-8-carboxylate,
propyl 3-p-fluorobenzoyl-5,6,7,8-tetrahydropyrrolo[1,2-a]pyridine-8-carboxylate, and
butyl 3-p-fluorobenzoyl-5,6,7,8-tetrahydropyrrolo[1,2-a]pyridine-8-carboxylate; and
methyl 3-p-fluorobenzoyl-6,7,8,9-tetrahydro-5H-pyrrolo[1,2-a]azepine-9-carboxylate,
ethyl 3-p-fluorobenzoyl-6,7,8,9-tetrahydro-5H-pyrrolo[1,2-a]azepine-9-carboxylate,
propyl 3-p-fluorobenzoyl-6,7,8,9-tetrahydro-5H-pyrrolo[1,2-a]azepine-9-carboxylate, and
butyl 3-p-fluorobenzoyl-6,7,8,9-tetrahydro-5H-pyrrolo[1,2-a]azepine-9-carboxylate.

EXAMPLE 11

Following the procedure of Example 7 using 1.1 to 5 molar equivalents of
N,N-dimethyl-benzamide,
N,N-dimethyl-m-butylbenzamide,
N,N-dimethyl-p-methoxybenzamide,
N,N-dimethyl-p-chloro-benzamide and
N,N-dimethyl-p-toluamide,
in place of N,N-dimethyl-p-fluorobenzamide, and monitoring the course of the reaction by t.l.c., there are obtained respectively:
isopropyl 3-benzoyl-5,6,7,8-tetrahydropyrrolo[1,2-a]pyridine-8-carboxylate,
isopropyl 3-m-butylbenzoyl-5,6,7,8-tetrahydropyrrolo[1,2-a]pyridine-8-carboxylate,
isopropyl 3-p-methoxybenzoyl-5,6,7,8-tetrahydropyrrolo[1,2-a]pyridine-8-carboxylate,
isopropyl 3-p-chlorobenzoyl-5,6,7,8-tetrahydropyrrolo[1,2-a]pyridine-8-carboxylate, and
isopropyl 3-p-toluyl-5,6,7,8-tetrahydropyrrolo[1,2-a]pyridine-8-carboxylate,
isopropyl 3-benzoyl-6,7,8,9-tetrahydropyrrolo[1,2-a]azepine-9-carboxylate,
isopropyl 3-m-butylbenzoyl-6,7,8,9-tetrahydropyrrolo[1,2-a]azepine-9-carboxylate,
isopropyl 3-p-methoxybenzoyl-6,7,8,9-tetrahydropyrrolo[1,2-a]azepine-9-carboxylate,
isopropyl 3-p-chlorobenzoyl-6,7,8,9-tetrahydropyrrolo[1,2-a]azepine-9-carboxylate, and
isopropyl 3-p-toluyl-6,7,8,9-tetrahydropyrrolo[1,2-a]azepine-9-carboxylate;

Hydrolysis of the above esters employing the procedures of Examples 8 or 9 yields:
3benzoyl-5,6,7,8-tetrahydropyrrolo[1,2-a]pyridine-8-carboxylic acid,
3-m-butylbenzoyl-5,6,7,8-tetrahydropyrrolo[1,2-a]pyridine-8-carboxylic acid,
3-p-methoxybenzoyl-5,6,7,8-tetrahydropyrrolo[1,2-a]pyridine-8-carboxylic acid,
3-p-chlorobenzoyl-5,6,7,8-tetrahydropyrrolo[1,2-a]pyridine-8-carboxylic acid,
3-p-toluyl-5,6,7,8-tetrahydropyrrolo[1,2-a]pyridine-8-carboxylic acid, and
3-benzoyl-6,7,8,9-tetrahydropyrrolo[1,2-a]azepine-9-carboxylic acid,
3-m-butylbenzoyl-6,7,8,9-tetrahydropyrrolo[1,2-a]azepine-9-carboxylic acid,
3-p-methoxybenzoyl-6,7,8,9-tetrahydropyrrolo[1,2-a]azepine-9-carboxylic acid,
3-p-chlorobenzoyl-6,7,8,9-tetrahydropyrrolo[1,2-a]azepine-9-carboxylic acid, and
3-p-toluyl-6,7,8,9-tetrahydropyrrolo[1,2-a]azepine-9-carboxylic acid.

EXAMPLE 12

A 250 ml. 2-necked round bottomed flask containing a magnetic stirring bar and fitted with a calcium chloride filled drying tube, is charged with propanolamine (I), cooled in an ice bath at 0°–10° C. and treated dropwise, with stirring, with dimethyl 1,3-acetone-dicarboxylate (II). Methyl 3-carbomethoxymethyl-3-(3′-hydroxypropyl)amino acrylate (III) forms immediately. When the addition is completed, the ice bath is removed and dry acetonitrile is added. The reaction mixture is then treated dropwise with bromoacetaldehyde in acetonitrile and thereafter heated at reflux temperature for 2 hours. The solvent is then removed under reduced pressure and 200 ml. of methanol and 20 g. of silica gel are added to the residue. This mixture is evaporated to dryness in vacuum and placed on top of a column of of silica gel packed in hexane, eluting the column with hexane:ethyl acetate mixtures. The fractions eluted with hexane:ethyl acetate afford methyl N-(3-hydroxypropyl)-3-carbomethoxypyrrole-2-acetate (IV, R=H, n=1) identical to the product obtained in Example 1.

In like manner, by substituting butanolamine for propanolamine and following the procedures of this example there is obtained methyl N-(4-hydroxybutyl)-3-carbomethoxypyrrole-2-acetate (IV, R=H, n=2).

EXAMPLE 13

To a solution of propanolamine in water there is added dimethyl 1,3-acetonedicarboxylate. The resultant mixture is rapidly cooled to −10° C. and treated dropwise, over a 15 minute period, with stirring, with 1-bromoacetone, whilst maintaining the reaction mixture at a temperature not higher than 40° C. When the addition is completed the dark reaction mixture is stirred for an additional hour at room temperature, and then poured into a mixture of hydrochloric acid-ice, saturated with solid sodium chloride and extracted with ethyl acetate (3×100 ml.). The combined organic extract is washed with cold water to neutrality, dried with anhydrous sodium sulfate and evaporated to dryness under reduced pressure. Chromatography of the residue on silica gel, using hexane:ethyl acetate as eluant, affords methyl N-(3-hydroxypropyl)-3-carbomethoxy-4-methylpyrrole-2-acetate (IV, R=CH$_3$, n=1).

In like manner, substituting butanolamine for propanolamine and following the procedure of this example there is obtained methyl N-(4-hydroxybutyl)-3-carbomethoxy-4-methylpyrrole-2-acetate (IV, R=CH$_3$, n=2).

In a similar manner but using a stoichiometric equivalent of 1-bromo-2-butanone, 1-bromo-2-pentanone and 1-bromo-2-hexanone in place of 1-bromoacetone there are respectively obtained:
methyl N-(3-hydroxypropyl)-3-carbomethoxy-4-ethylpyrrole-2-acetate,
methyl N-(3-hydroxypropyl)-3-carbomethoxy-4-propylpyrrole-2-acetate, and
methyl N-(3-hydroxypropyl)-3-carbomethoxy-4-butylpyrrole-2-acetate; and
methyl N-(4-hydroxybutyl)-3-carbomethoxy-4-ethylpyrrole-2-acetate,
methyl N-(4-hydroxybutyl)-3-carbomethoxy-4-propylpyrrole-2-acetate, and
methyl N-(4-hydroxybutyl)-3-carbomethoxy-4-butylpyrrole-2-acetate.

EXAMPLE 14

By following the methods of Examples 2, 3, 4, 5 and 6, methyl N-(3-hydroxypropyl)-3-carbomethoxy-4-methylpyrrole-2-acetate (IV, R=CH$_3$, n=1) is converted successively into:
methyl N-(3-mesyloxypropyl)-3-carbomethoxy-4-methylpyrrole-2-acetate,
methyl N-(3-iodopropyl)-3-carbomethoxy-4-methylpyrrole-2-acetate,
dimethyl 2-methyl-5,6,7,8-tetrahydropyrrolo-[1,2-a]pyridine-1,8-carboxylate,
2-methyl-5,6,7,8-tetrahydropyrrolo[1,2-a]pyridine-1,8-dicarboxylic acid,
isopropyl 2-methyl-5,6,7,8-tetrahydropyrrolo-[1,2-a]pyridine-8-carboxylate-1-carboxylic acid and
isopropyl 2-methyl-5,6,7,8-tetrahydropyrrolo[1,2-a]pyridine-8-carboxylate (X, R=CH$_3$, R$^2$=iC$_3$H$_7$, n=1).

In like manner, by following the methods of Examples 2, 3, 4, 5, and 6, methyl N-(4-hydroxybutyl-3-carbomethoxy-4-methylpyrrole-2-acetate (IV, R=CH$_3$, n=2) is converted successively into:
methyl N-(3-mesyloxybutyl)-3-carbomethoxy-4-methylpyrrole-2-acetate,
methyl N-(3-iodobutyl)-3-carbomethoxy-4-methylpyrrole-2acetate,
dimethyl 2-methyl-6,7,8,9-tetrahydro-5H-pyrrolo-[1,2-a]azepine-1,9-carboxylate,
2-methyl-6,7,8,9-tetrahydro-5H-pyrrolo[1,2-a]azepine-1,9-carboxylic acid,
isopropyl 2-methyl-6,7,8,9-tetrahydro-5H-pyrrolo[1,2-a]azepine-9-carboxylate-1-carboxylic acid and
isopropyl 2-methyl-6,7,8,9-tetrahydro-5H-pyrrolo[1,2-a]azepine-9-carboxylate (X, R=CH$_3$, R$^2$=iC$_3$H$_7$, n=2).

In a similar manner substituting methyl N-(3-hydroxypropyl)-3-carbomethoxy-4-ethylpyrrole-2-acetate, methyl N-(3-hydroxypropyl)-3-carbomethoxy-4-propylpyrrole-2-acetate, methyl N-(3-hydroxyethyl)-3-carbomethoxy-4-butylpyrrole-2-acetate; methyl N-(4-hydroxybutyl)-3-carbomethoxy-4-ethylpyrrole-2-acetate, methyl N-(4-hydroxybutyl)-3-carbomethoxy-4-propylpyrrole-2-acetate, and methyl N-(4-hydroxybutyl)-3-carbomethoxy-4-butylpyrrole-2-acetate, for methyl N-(3-hydroxypropyl)-3-carbomethoxy-4-methylpyrrole-2-acetate there are respectively obtained as final products:
isopropyl 2-ethyl-5,6,7,8-tetrahydropyrrolo[1,2-a]-pyridine-8-carboxylate,
isopropyl 2-propyl-5,6,7,8-tetrahydropyrrolo[1,2-a]-pyridine-8-carboxylate and
isopropyl 2-butyl-5,6,7,8-tetrahydropyrrolo[1,2-a]-pyridine-8-carboxylate; and
isopropyl 2-ethyl-6,7,8,9-tetrahydro-5H-pyrrolo-[1,2-a]azepine-9-carboxylate,
isopropyl 2-propyl-6,7,8,9-tetrahydro-5H-pyrrolo-[1,2-a]azepine-9-carboxylate,
isopropyl 2-butyl-6,7,8,9-tetrahydro-5H-pyrrolo-[1,2-a]azepine-9-carboxylate.

EXAMPLE 15

3-Amino-1-propanol (300 g, 3.99 moles) was added with efficient agitation to glacial acetic acid (540 ml, cooled in an ice-salt mixture) at a rate such that the internal temperature was maintained at 15°–25° C. When the above adition was completed, 2,5-dimethoxytetrahydrofuran (150 g, 1.14 moles) was added and the apparatus was removed from the cooling bath and set up for downward distillation. The solution was heated with an oil bath until distillation commenced (118° C.) and the distillate, b.p. 118°–120° C. was collected (ca. 200 ml) during 1.5 h. The residual liquid was cooled to room temperature, and poured into a mixture of ice and saturated sodium chloride solution (900 ml). The product was extracted into dichloromethane (4×700 ml), the extract was washed with saturated sodium chloride solution and then with saturated sodium carbonate solution. After drying over sodium sulfate the extract was concentrated in vacuo to leave an oil (146.4 g) which consists of a compound of Formula (XV where n=1) (major) and a lesser amount of the corresponding acetate.

This mixture was dissolved in methanol (150 ml) and a 20 wt% solution (85 ml) of aqueous sodium hydroxide (17 g of NaOH, 0.425 moles) was added. The solution was agitated at room temperature for 1 hour and then it was poured into a mixture of ice and saturated sodium chloride solution (600 ml). The product was extracted into dichloromethane (4×500 ml), the extract was washed twice with a dilute solution of sodium chloride and then it was dried over sodium sulfate. The solvent was removed in vacuo and the residue was purified by column chromatography on Florisil to give 79.6 g (56%) of 1-(3-hydroxypropyl)pyrrole (XV where n is 1) in those fractions eluted by hexane dichloromethane (3:1 and 1:1). The oil is further purified by distillation, b.p. 141°/0.15 mm for analysis.

Calcd. for C$_7$H$_{11}$NO: C, 67.17; H, 8.96; N, 11.15.
Found: C, 67.04; H, 8.93; N, 11.12.
U.V.: (MeOH) 223 nm ($\epsilon$ 4570).
I.R.: (CHCl$_3$); 3436, cm$^{-1}$.
N.M.R.: (CDCl$_3$); 2.00 (m, 2H)); 3.55 (t, 2H, J=6 Hz); 3.95 (t, 2H, J=6 Hz); 6.10 (m, 2H); 6.61 (m, 2H); M.S. 125 (M+).

In like manner, by substituting 4-amino-1-butanol for 3-amino-1-propanol there is obtained 1-(4-hydroxybutyl)pyrrole (XV where n is 1) having the following physical constants:

B.P.: 91° (0.25 mm).
U.V.: 224 nm ($\epsilon$ 3802).
I.R.: (CHCl$_3$). 3597, 3460, cm$^{-1}$.
N.M.R.: (CHCl$_3$); 1.66 (m, 4H); 3.56 (t, 2H, J=6 Hz); 3.86 (t, 2H, J=6 Hz); 6.10 (m, 2H); 6.60 (m, 2H); 1.33, 2.0 (OH).
M.S.: 139 (M+).
Calcd. for C$_8$H$_{13}$NO: C, 69.02; H, 9.41; N, 10.06 Found: C, 68.55; H, 9.48; N, 10.03.

EXAMPLE 16

60 G (0.479 moles) of 1-(3-hydroxypropyl)pyrrole is heated in an oil bath to 50° and a preheated (45°) solution of dimethylamine hydrochloride (46 g, 0.564 moles) in 37% aqueous formaldehyde (43 g, 0.698 moles) is added slowly with stirring at a rate such that the reaction temperature does not exceed 60°. The reaction mixture is then cooled to room temperature and agitation is continued for 2 hours. The reaction is followed by t.l.c. on silica gel using dichloromethane-methanol (90:10) as the developing solvent. At the end of the above time period, 20% aqueous sodium hydroxide (34 ml, equivalent to 16.8 g, 0.42 moles of NaOH) and water (240 ml) is added and the product is extracted into dichloromethane. The extract is washed successively with saturated sodium chloride solution and water then dried over sodium sulfate. The solvent is removed in vacuo and the residue (83.0 g) is purified by column chromatography on silica gel. The fractions eluted with dichloromethane-methanol (95:5) contained 1-(3-hydroxypropyl)-2-dimethylaminomethylpyrrole (XVI where n is 1) (57 g, 62%) which could be made analytically pure by distillation, b.p. 129°/0.15 mm.)

Calcd. for C$_{10}$H$_{18}$N$_2$): C, 65.89; H, 9.95; N, 15.37 Found: C, 65.78; H, 10.10; N, 15.09.
U.V. (MeOH) 226.5 nm ($\epsilon$ 6310).
I.R. (CHCl$_3$); 3115, cm$^{-1}$.
N.M.R.: (CDCl$_3$); 1.83 (m, 2H); 2.21 (s, 6H); 3.21 (m, 2H); 3.33 (s, 2H); 3.98 (m, 2H); 6.06 (m, 2H); 6.65 (m, 1H).
M.S.: 182 (M+).

In like manner, by substituting 1-(4-hydroxybutyl)pyrrole for 1-(3-hydroxypropyl)pyrrole, there is obtained 1-(4-hydroxybutyl)-2-dimethylaminomethylpyrrole (Formula (XVI) where n=2) which is purified by distillation in vacuo to give an oil with the following physical constants:

U.V.: 227.5 nm ($\epsilon$ 6166).
I.R.: (CHCl$_3$); 3289, cm$^{-1}$.
N.M.R.: (CHCl$_3$); 1.5 (m, 4H); 2.21 (s, 6H); 3.8 (s, 2H); 3.56 (t, 2H); 2.95 (t, 2H); 6.00 (m, 2H); 6.61 (m, 1H).

EXAMPLE 17

Dimethyl sulfate (44.2 g, 0.362 moles) is added to a stirred and cooled solution of 1-(3-hydroxypropyl)-2-dimethylaminopyrrole (57 g, 0.313 moles) in acetone (285 ml), maintained in an atmosphere of nitrogen, at a rate such that the reaction temperature does not exceed 4° C. The reaction is then allowed to come to room temperature at which point stirring is continued for a further 1 hour. The reaction is complete (t.l.c., silica gel, CH$_2$Cl$_2$—MeOH; 90:10) at this time and a solution of sodium cyanide (33.4 g., 1.28 moles) in water (74 ml.) is added. The apparatus is equipped to permit distillation and the reaction is heated to 95° during which time a distillate (ca. 275 ml.) is collected. The reaction is then heated at gentle reflux for 0.5 hours and 150 ml. water is added. the product is extracted into dichloromethane (4×200 ml.), the extract is washed with dilute sodium chloride solution and then dried over sodium sulfate. The solvent is removed in vacuo and the oily residue (51 g) is purrified by column chromatography over silica gel to give 38.1 g (74%) 1-(3-hydroxypropyl)pyrrol-2-acetonitrile (Formula (XVII) where n is 1) which is contained in the hexane-ethyl acetate (85:15) eluate. The product on distillation, b.p. 146°/0.15 mm is analytically pure and exhibited the following physical characteristics:

Calcd. for C$_9$H$_{12}$N$_2$: C, 65.82; H, 7.37; N, 17.06; Found: C, 65.70; H, 7.57; N, 16.81.
U.V.: 222.5, 259 nm ($\epsilon$ 5890, 1950).
I.R.: (CHCl$_3$); 3425, 2183 cm$^{-1}$.
N.M.R.: (CDCl$_3$): 1.95 (m, 3H); 3.61 (m, 4H); 4.10 (t, 2H, J=4 Hz); 6.06 (m, 2H); 6.63 (m, 1H);
M.S.: 164 (M+).

In like manner, by substituting 1-(4-hydroxy)butyl-2-dimethylaminopyrrole for 1-(3-hydroxypropyl)-2-dimethylaminopyrrole, there is obtained 1-(4-hydroxybutyl)pyrrol-2-acetonitrile (Formula (XVII) where n is 2) which exhibits the following physical characteristics:

U.V.: 224.5, 260 nm ($\epsilon$ 5130, 1150).
I.R.: (CHCl$_3$); 3460, 2232, 2188 cm$^{-1}$.
N.M.R.: (CHCl$_3$); 1.76 (m, 4H); 3.76 (m, 6H); 6.06 (m, 2H); 6.63 (m, 1H).
M.S.: 178 (M+).

EXAMPLE 18

Triethylamine (31 g, 0.306 moles) and methanesulfonyl chloride (32 g, 0.279 moles) are successively added to a stirred and cooled (−8°) solution of 1-(3-hydroxypropyl)pyrrol-2-acetonitrile (38.1 g., 0.232 moles) in dichloromethane (250 ml.), maintained in an atmosphere of nitrogen, at a rate such that the reaction temperature did not exceed 0°. After a further 1 hour at this temperature (t.l.c. silica gel, dichloromethane-acetone, 95:5), saturated sodium becarbonate solution (4.4 ml.), saturated sodium chloride solution (45 ml.) and water (50 ml.) is added. The mixture is stirred for 5 min., the organic phase is separated, and combined with the dichloromethane extracts (2×100 ml.) of the aqueous phase. The extract is washed successively with saturated sodium bicarbonate solution (25 ml.), saturated sodium chloride solution (50 ml.) and water (50 ml.), and then dried over sodium sulfate. The solvent was removed in vacuo and the residual oil (77 g) is purified by chromatography on silica gel to give 42.7 g of 1-(3-methansul-fonyloxypropyl)pyrrol-2-acetonitrile (Formula (XVIII) where n is 1), (76%) was contained in the fraction eluted with hexane-dichloromethane (90:10). This product has the following physical characteristics:

Calcd. for C$_{10}$H$_{14}$N$_2$O$_3$S: C, 49.57; H, 5.92; N, 11.56 Found: C, 49.46; H, 5.91; N, 11.60.
U.V.: 222.5, 259 nm ($\epsilon$6030, 4370).
I.R.: (CHCl$_3$); 2183 cm$^{-1}$.
N.M.R.: (CDCl$_3$); 2.13 (m, 2H); 3.03 (s, 3H); 4.00 (m, 6H); 6.01 (m, 2H); 6.68 (m, 1H).
M.S.: 242 (M+).

In like manner, by substituting 1-(4-hydroxybutyl)-pyrrol-2-acetonitrile for 1-(3-hydroxypropyl)pyrrol-2-acetonitrile there is obtained 1-(4-methansulfonyloxybutyl)pyrrol-2-acetonitrile (Formula (XVIII) where n is 2) which is an oil having the following physical characteristics:

U.V.: 223, 260 nm ($\epsilon$5890, 1480).
I.R.: (CHCl$_3$); 2217, 2179 cm$^{-1}$.
N.M.R.: (CHCl$_3$); 1.85 (m, 4H); 3.00 (s, 3H); 3.7 (s, 2H); 3.86 (t, 2H, J=6 Hz); 4.21 (t, 2H, J=5 Hz); 6.11 (m, 2H); 6.66 (m, 1H).
Calcd. for $C_{11}H_{16}O_3N_2S$: C, 51.49; H, 6.29; N, 10.93. Found: C, 51.69; H, 6.37; N, 10.74.

EXAMPLE 19

A solution of 8 g. of 1-(3-methansulfonyloxypropyl)-pyrrol-2-acetonitrile (0.33 moles) in dry acetonitrile (270 ml.) containing dry sodium iodide (12.2 g., 0.081 moles) is stirred under reflux for 40 min. (t.l.c., silica gel, hexane-ethyl acetate, 1:1). The reaction is cooled to 40°, water (50 ml.) is added, and the solvent is then removed in vacuo almost to dryness. To the residue is added saturated sodium chloride solution (300 ml.) and dichloromethane (350 ml.). The organic phase is separated combined with the dichloromethane extracts of the aqueous phase (3×150 ml.), and washed successively with saturated sodium chloride solution, saturated sodium sulfite solution (once) and dilute sodium chloride solution. The solution is dried with sodium sulfate and evaporated in vacuo giving 1-(3-iodopropyl)pyrrol-2-acetonitrile which is an oil (7.7 g) having the following characteristics:

U.V.: 219 (Sh), 255 nm ($\epsilon$6760, 5750).
I.R.: (CHCl$_3$); 2212 cm$^{-1}$.
N.M.R: (CDCl$_3$); 2.21 (m, 2H); 3.06 (t, 2H); 3.86 (m, 4H); 6.20 (m, 2H); 6.63 (m, 1H).
M.S.: 274 (M+).

1-(3-Iodopropyl)pyrrol-2-acetonitrile (31 g., 0.128 moles) is dissolved in dry dimethylformanide (35 ml.) is added with stirring to a cooled (−5°) suspension of sodium hydride (50%, 7.5 g., 0.156 moles) in dry dimethylformamide (100 ml.), maintained in an atmosphere of dry nitrogen, at a rate such that the reaction temperature is maintained between −5° to +5°. When the addition is completed, stirring at this temperature is continued for 1 hour at which time the starting material is shown to be absent by t.l.c. (silica gel, hexane-ethyl acetate, 1:1). A cold, dilute solution of sodium chloride (150 ml.) is added to the reaction during 15 minutes and the product is extracted into benzene. The extract is washed with dilute sodium chloride solution (3 times), with water (once) and then it is dried over sodium sulfate. The solvent is removed in vacuo leaving an oil (21.1 g.) which is chromatographed on silica gel. The crystalline product (13.6 g., 72%) is eluted with hexane-ethyl acetate (97.5:25 and 95:5). Crystallization from hexane-acetone yields 8-cyano-5,6,7,8-tetrahydropyrrolo[1,2-a]pyridine (XIX, n is 1), m.p. 47°-49°.

EXAMPLE 20

To a stirred suspension of sodium hydride (obtained from 2.5 g. of 50% sodium hydride in mineral oil which had been freed of the carrier with hexane) in anhydrous dimethylformamide (60 ml.), maintained in an atmosphere of nitrogen and cooled to −5°, is added a solution of 1-(4-methansulfonyloxybutyl)pyrrol-2-acetonitrile (10 g, 0.062 moles) in dimethylformamide (40 ml.) at a rate such that the temperature is maintained at 10°-15° C. After the addition, stirring at this temperature is continued for 1 hours, and then a dilute sodium chloride solution (500 ml.) is added. The product is extracted into benzene (4×200 ml.), the extract is washed with water (4×500 ml.), dried, and evaporated in vacuo. The residue is purified by column chromatography on silica gel using hexane-ethyl acetate (95:5) as the eluting solvent to give a crude product in a 69% yield. Crystallization from acetone-hexane gives 9-cyano-6,7,8,9-tetrahydro-5H-pyrrolo[1,2-a]azepine (Formula (XIX) where n is 1), m.p. of 70°-72° C.

EXAMPLE 21

A solution of 8-cyano-5,6,7,8-tetrahydropyrrolo[1,2-a]pyridine (1.0 g., 6.8 mmoles) and benzoyl chloride (2 ml., 17 mmoles) in dry xylene (70 ml.) is heated at reflux temperature in a nitrogen atmosphere for 24 hours. The solvent is then removed in vacuo and the residue is purified by column chromatography on silica gel (50 g.). The starting material is put on the column with dichloromethane-hexane (1:1) and elution with dichloromethane gives 1.12 g. (65%) of a product containing 8-cyano-3-benzoyl-5,6,7,8-tetrahydropyrrolo[1,2-a]pyridine (Formula (XXI) where n is 1 and L is H). Crystallization from acetone-hexane gives a purified product having a m.p. of 100°-102° C.

A mixture of the nitrile so prepared (1.5 g., 0.006 moles), 88% potassium hydroxide (2.0 g., 0.035 moles), ethylene glycol (20 ml.) and water (2 ml.) is heated in an oil bath at 110°-115° for 3 hours. Water (60 ml.) is added to the cooled solution and the resultant mixture is extracted with ether. The alkaline solution is made acidic (at 5°) to a pH-2 with concentrated hydrochloric acid and the product is extracted into ethyl acetate. The extract is washed with water, dried over sodium sulfate and evaporation in vacuo. The residue is crystallized from ethyl acetate-ether to give 3-benzoyl-5,6,7,8-tetrahydropyrrolo[1,2-a]pyridine-8-carboxylic which has m.p. 168°-169° C.

EXAMPLE 22

A solution of potassium hydroxide (2.02 g) in water (1.2 ml.) is added to a solution of 9-cyano-5,6,7,8-tetrahydro-9H-pyrrolo[1,2-a]azepine (1.0 g., 0.006 moles) in ethylene glycol (11 ml.) at 5°. The solution thus obtained is placed in an oil bath at 118° and after 3 hours the cooled solution is poured into water (50 ml.). The aqueous alkaline phase is extracted with ether (20 ml.) the aqueous phase is made acidic to pH-2 with concentrated hydrochloric acid at 5°. The product is extracted into ethyl acetate (4×40 ml.), the extract is washed with water to neutrality, dried and evaporated. Crystallization of the residue from ethyl acetate-ether gave 5,6,7,8-tetrahydro-9H-pyrrolo[1,2,a]azepine-9-carboxylic acid, (92% yield), m.p. 129°-130° C.

Excess ethereal diazomethane is added to a solution of the resulting acid (0.600 g, 0.003 moles) in dichloromethane (15 ml.). The volatiles were removed in vacuo and the residue is purified by t.l.c. on silica gel using hexane-ethyl acetate (3:1) as the eluting solvent. The product, obtained in 68% yield is crystallized from acetone-hexane to give methyl-5,6,7,8-tetrahydro-9H-pyrrolo[1,2,a]azepine-9-carboxylate, m.p. 56°-57° C.

A solution of the resulting ester (1.2 g., 0.006 moles) in dry xylene (50 ml.) containing benzoyl chloride (1.5 g., 0.01 moles) is heated at reflux temperature, in a nitrogen atmosphere, for 44 hours. The solvent is removed in vacuo and the residue is purified by t.l.c. on silica gel (hexane-ethyl acetate, 3:1) to give a product in 50% yield which, when crystallized from acetone hexane, gives methyl-3-benzoyl-5,6,7,8-tetrahydro-9H-pyrrolo[1,2-a]azepine-9-carboxylate having a m.p. 98°–99° C.

EXAMPLE 23

Following in principle the procedure of Example 21, using 1.1 to 5 molar equivalents of
p-methylbenzoyl chloride,
o-methylbenzoyl chloride,
m-methylbenzoyl chloride,
p-ethylbenzoyl chloride,
o-propylbenzoyl chloride,
m-butylbenzoyl chloride,
o-methoxybenzoyl chloride,
p-methoxybenzoyl chloride,
p-ethoxybenzoyl chloride,
p-isopropoxybenzoyl chloride,
o-chlorobenzoyl chloride,
m-chlorobenzoyl chloride,
p-chlorobenzoyl chloride,
o-fluorobenzoyl chloride,
p-fluorobenzoyl chloride,
m-bromobenzoyl chloride,
o-bromobenzoyl chloride,
in place of benzoyl chloride, and monitoring the course of the reaction by t.l.c., there are obtained respectively:
3-p-toluoyl-5,6,7,8-tetrahydropyrrolo[1,2-a]pyridine-8-carboxylic acid, m.p. 146°–147° C. (recrystallized from acetone/hexane),
3-o-toluoyl-5,6,7,8-tetrahydropyrrolo[1,2-a]pyridine-8-carboxylic acid,
3-m-toluoyl-5,6,7,8-tetrahydropyrrolo[1,2-a]pyridine-8-carboxylic acid,
3-p-ethylbenzoyl-5,6,7,8-tetrahydropyrrolo[1,2-a]-pyridine-8-carboxylic acid,
3-o-propylbenzoyl-5,6,7,8-tetrahydropyrrolo[1,2-a]-pyridine-8-carboxylic acid,
3-m-butylbenzoyl-5,6,7,8-tetrahydropyrrolo[1,2-a]-pyridine-8-carboxylic acid,
3-o-methoxybenzoyl-5,6,7,8-tetrahydropyrrolo[1,2-a]-pyridine-8-carboxylic acid,
3-p-methoxybenzoyl-5,6,7,8-tetrahydropyrrolo[1,2,-a]-pyridine-8-carboxylic acid, m.p. 156°–157° C.,
3-p-ethoxybenzoyl-5,6,7,8-tetrahydropyrrolo[1,2-a]pyridine-8-carboxylic acid,
3-p-isopropoxybenzoyl-5,6,7,8-tetrahydropyrrolo-[1,2-a]pyridine-8-carboxylic acid,
3-o-chlorobenzoyl-5,6,7,8-tetrahydropyrrolo[1,2-a]-pyridine-8-carboxylic acid,
3-m-chlorobenzoyl-5,6,7,8-tetrahydropyrrolo[1,2-a]-pyridine-8-carboxylic acid,
3-p-chlorobenzoyl-5,6,7,8-tetrahydropyrrolo[1,2-a]-pyridine-8-carboxylic acid, m.p. 153°–155° C.,
3-o-fluorobenzoyl-5,6,7,8-tetrahydropyrrolo[1,2-a]-pyridine-8-carboxylic acid,
3-p-fluorobenzoyl-5,6,7,8-tetrahydropyrrolo[1,2-a]-pyridine-8-carboxylic acid, m.p. 161°–162° C.,
3-m-bromobenzoyl-5,6,7,8-tetrahydropyrrolo[1,2-a]-pyridine-8-carboxylic acid and By esterifying the above acids according to the process of Example 22 the corresponding methyl esters are obtained such as
methyl 3-benzoyl-5,6,7,8-tetrahydropyrrolo[1,2-a]-pyridine-8-carboxylate,
methyl 3-p-toluoyl-5,6,7,8-tetrahydropyrrolo[1,2-a]-pyridine-8-carboxylate,
methyl 3-o-toluoyl-5,6,7,8-tetrahydropyrrolo[1,2-a]-pyridine-8-carboxylate,
methyl 3-m-toluoyl-5,6,7,8-tetrahydropyrrolo[1,2-a]-pyridine-8-carboxylate
methyl 3p-ethylbenzoyl-5,6,7,8-tetrahydropyrrolo-[1,2-a]pyridine-8-carboxylate,
methyl 3-o-propylbenzoyl-5,6,7,8-tetrahydropyrrolo-[1,2-a]pyridine-8-carboxylate,
methyl 3-m-butylbenzoyl-5,6,7,8-tetrahydropyrrolo-[1,2-a]pyridine-8-carboxylate,
methyl 3-o-methoxybenzoyl-5,6,7,8-tetrahydropyrrolo-[1,2-a]pyridine-8-carboxylate,
methyl 3-p-methoxybenzoyl-5,6,7,8-tetrahydropyrrolo-[1,2-a]pyridine-8-carboxylate,
methyl 3-p-ethoxybenzoyl-5,6,7,8-tetrahydropyrrolo-[1,2-a]pyridine-8-carboxylate,
methyl 3p-isopropoxybenzoyl-5,6,7,8-tetrahydropyrrolo[1,2-a]pyridine-8-carboxylate,
methyl 3-o-chlorobenzoyl-5,67,8-tetrahydropyrrolo[1,2-a]pyridine-8-carboxylate,
methyl 3-m-chlorobenzoyl-5,6,7,8-tetrahydropyrrolo[1,2-a]pyridine-8-carboxylate,
methyl 3-p-chlorobenzoyl-5,6,7,8-tetrahydropyrrolo-[1,2-a]pyridine-8-carboxylate,
methyl 3-o-fluorobenzoyl-5,6,7,8-tetrahydropyrrolo-[1,2]pyridine-8-carboxylate,
methyl 3-p-fluorobenzoyl-5,6,7,8-tetrahydropyrrolo[1,2-a]pyridine-8-carboxylate, m.p. 78°–79° C.,
methyl 3-m-bromobenzoyl-5,6,7,8-tetrahydropyrrolo[1,2-a]pyridine-8-carboxylate, and p0 methyl 3-p-bromobenzoyl-5,6,7,8-tetrahydropyrrolo[1,2-a]pyridine-8-carboxylate; and By following in principle the process of Example 11, other corresponding esters are prepared, i.e. the ethyl, propyl, isopropyl and butyl carboxylates.

EXAMPLE 24

A. Following the procedure of Example 22 using 1.1 to 5 molar equivalents of
o-methylbenzoyl chloride,
m-methylbenzoyl chloride,
p-ethylbenzoyl chloride,
o-propylbenzoyl chloride,
m-butylbenzoyl chloride,
o-methoxybenzoyl chloride,
p-methoxybenzoyl chloride,
p-ethoxybenzoyl chloride,
p-isopropoxybenzoyl chloride,
o-chlorobenzoyl chloride,
m-chlorobenzoyl chloride,
p-chlorobenzoyl chloride,
o-fluorobenzoyl chloride,
p-fluorobenzoyl chloride, m-bromobenzyl chloride,
p-bromobenzoyl chloride,
in place of benzoyl chloride and monitoring the course of the reaction by t.l.c. there are obtained respectivelyl:
methyl 3-o-toluoyl-6,7,8,9-tetrahydro-5H-pyrrolo-[1,2-a]azepine-9-carboxylate,
methyl 3-m-toluoyl-6,7,8,9-tetrahydro-5H-pyrrolo[1,2-a]azepine-9-carboxylate,
methyl 3-p-ethylbenzoyl-6,7,8,9-tetrahydro-5H-pyrrolo[1,2-a]azepine-9-carboxylate,
methyl 3-o-propylbenzoyl-6,7,8,9-tetrahydro-5H-pyrrolo[1,2-a]azepine-9-carboxylate,
methyl 3-m-butylbenzoyl-6,7,8,9-tetrahydro-5H-pyrrolo[1,2-a]azepine-9-carboxylate,
methyl 3-o-methoxybenzoyl-6,7,8,9-tetrahydro-5H-pyrrolo[1,2-a]azepine-9-carboxylate,
methyl 3-p-methoxybenzoyl-6,7,8,9-tetrahydro-5H-pyrrolo[1,2-a]azepine-9-carboxylate, methyl 3-p-ethoxybenzoyl-6,7,8,9-tetrahydro-5H-pyrrolo[1,2-a]azepine-9-carboxylate,
methyl 3-p-isopropoxybenzoyl-6,7,8,9-tetrahydro-5H-pyrrolo[1,2-a]azepine-9-carboxylate,
methyl 3-o-chlorobenzoyl-6,7,8,9-tetrahydro-5H-pyrrolo[1,2,-a]azepine-9-carboxylate,
methyl 3-m-chlorobenzoyl-6,7,8,9-tetrahydro-5H-pyrrolo[1,2-a]azepine-9-carboxylate,
methyl 3-p-chlorobenzoyl-6,7,8,9-tetrahydro-5H-pyrrolo[1,2-a]azepine-9-carboxylate,
methyl 3-o-fluorobenzoyl-6,7,8, 9-tetrahydro-5H-pyrrolo[1,2-a]azepine-9-carboxylate,
methyl 3-p-fluorobenzoyl-6,7,8,9-tetrahydro-5H-pyrrolo[1,2-a]azepine-9-carboxylate,
methyl 3-m-bromobenzoyl-6,7,8,9-tetrahydro-5H-pyrrolo[1,2-a]azepine-9-carboxylate, and
methyl 3-p-bromobenzoyl-6,7,8,9-tetrahydro-5H-pyrrolo[1,2-a]azepine-9-carboxylate.

B. A solution of methyl 2-benzoyl-6,7,8,9-tetrahydro-5H-pyrrolo[1,2-a]azepine-9-carboxylate (1.00 g., 0.0034 moles) in methanol (30 ml.) and water (10 ml.) containing potassium carbonate (0.940 g., 0.0068 moles) was heated at reflux temperature, in a nitrogen atmosphere, for 2 hours. The solvent was removed in vacuo, water (25 ml.) was added and the solution was extracted with ether (2×50 ml.). The aqueous phase was cooled to 5°, oxalic acid (2.55 g., 0.02 moles) was added, and after agitation for 0.5 hours the product was extracted into ethyl acetate (3×100 ml.). The extract was washed with water, dried over sodium sulfate and evaporated in vacuo. The residue, on crystallization from ethylacetate/hexane gives 3-benzoyl-5,6,7,8-tetrahydro-9H-pyrrolo[1,2-a]azepine-9-carboxylic acid in 73% yield, m.p. 163°-165° C.

In like, manner, the hydrolysis of the above esters of this example gives the following products:
3-o-toluoyl-6,7,8,9-tetrahydro-5H-pyrrolo[1,2-a]azepine-9-carboxylic acid,
3-m-toluoyl-6,7,8,9-tetrahydro-5H-pyrrolo[1,2-a]azepine-9-carboxylic acid,
3-p-ethylbenzoyl-6,7,8,9-tetrahydro-5H-pyrrolo[1,2-a]azepine-9-carboxylic acid,
3-o-propylbenzoyl-6,7,8,9-tetrahydro-5H-pyrrolo[1,2-a]azepine-9-carboxylic acid,
3-m-butylbenzoyl-6,7,8,9-tetrahydro-5H-pyrrolo[1,2-a]azepine-9-carboxylic acid,
3-o-methoxybenzoyl-6,7,8,9-tetrahydro-5H-pyrrolo[1,2-a]azepine-9-carboxylic acid,
3-p-methoxybenzoyl-6,7,8,9-tetrahydro-5H-pyrrolo[1,2-a]azepine-9carboxylic acid,
3-p-ethoxybenzoyl-6,7,8,9-tetrahydro-5H-pyrrolo[1,2-a]azepine-9-carboxylic acid,
3-p-isopropoxybenzoyl-6,7,8,9-tetrahydro-5H-pyrrolo[1,2-a]azepine-9-carboxylic acid,
3-o-chlorobenzoyl-6,7,8,9-tetrahydro-5H-pyrrolo[1,2-a]azepine-9-carboxylic acid,
3-m-chlorobenzoyl-6,7,8,9-tetrahydro-5H-pyrrolo[1,2-a]azepine-9-carboxylic acid,
3-p-chlorobenzoyl-6,7,8,9-tetrahydro-5H-pyrrolo[1,2-a]azepine-9-carboxylic acid,
3-o-fluorobenzoyl-6,7,8,9-tetrahydro-5H-pyrrolo[1,2-a]azepine-9-carboxylic acid,
3-p-fluorobenzoyl-6,7,8,9-tetrahydro-5H-pyrrolo[1,2-a]azepine-9-carboxylic acid,
3-m-bromobenzoyl-6,7,8,9-tetrahydro-5H-pyrrolo[1,2-a]azepine-9-carboxylic acid and
3-p-bromobenzoyl-6,7,8,9-tetrahydro-5H-pyrrolo[1,2-a]azepine-9-carboxylic acid.

EXAMPLE 25

A solution of 8-cyano-5,6,7,8-tetrahydropyrrolo[1.2-a]pyridine (8 g., 0.054 moles) in anhydrous xylene (100 ml.) containing p-methylthiobenzoyl chloride (18.2 g., 0.098 moles) is heated at reflux temperature in a nitrogen atmosphere for 24 hours. The solvent is removed in vacuo and the residue is purified by t.l.c. on silica gel using dichloromethane as the developing solvent. The product (24% yield) is crystallized from acetone-hexane to give 3-p-methylthiobenzoyl-8-cyano-5,6,7,8-tetrahydropyrrolo[1,2-a]pyridine, m.p. 118°-119°.

A solution of the resulting nitrile (1.5 g., 0.005 moles) in ethylene glycol (20 ml.) containing water (1.6 ml.) and potassium hydroxide (1.65 g.) is heated in an oil bath at 110°-120°, in a nitrogen atmosphere, for 2.5 hours. The solution is cooled to room temperature, it is poured into water (60 ml.) and extracted with ether (2×30 ml.). The aqueous alkaline phase is cooled to 5° C. and made acidic to pH-4. The product is extracted into ethyl acetate (3×100 ml.), the extract is washed with water, dried, and evaporated in vacuo. The residue is crystallized from dichloromethane-methanol to give 3-p-methylthiobenzoyl-5,6,7,8-tetrahydropyrrolo[1,2-a]pyridine-8-carboxylic acid, m.p. 174°-175°.

By following in principle the above procedure but substituting other alkylthiobenzoyl chlorides for methylthiobenzoyl chloride, i.e.
o-methylthiobenzoyl chloride,
m-methylthiobenzoyl chloride,
p-ethylthiobenzoyl chloride,
p-propylthiobenzoyl chloride,
p-isopropylthiobenzoyl chloride,
p-butylthiobenzoyl chloride,
p-isobutylthiobenzoyl chloride and the like one obtains
3-o-methylthiobenzoyl-5,6,7,8-tetrahydropyrrolo[1,2-a]pyridine-8-carboxylic acid,
3-m-methylthiobenzoyl-5,6,7,8-tetrahydropyrrolo[1,2-a]pyridine-8-carboxylic acid,
3-p-ethylthiobenzoyl-5,6,7,8-tetrahydropyrrolo[1,2-a]pyridine-8-carboxylic acid,
3-p-propylthiobenzoyl-5,6,7,8-tetrahydropyrrolo[1,2-a]pyridine-8-carboxylic acid,
3-p-isopropylthiobenzoyl-5,6,7,8-tetrahydropyrrolo[1,2,-a]pyridine-8-carboxylic acid,
3-p-butylthiobenzoyl-5,6,7,8-tetrahydropyrrolo[1,2-a]pyridine-8-carboxylic acid, and
3-p-isobutylthiobenzoyl-5,6,7,8-tetrahydropyrrolo[1,2-a]pyridine-8-carboxylic acid.

By esterifying the above acids according to the process of Example 22 the corresponding methyl esters are obtained such as
methyl 3-p-methylthiobenzoyl-5,6,7,8-tetrahydropyrrolo[1,2-a]pyridine-8-carboxylate,
methyl 3-o-methylthiobenzoyl-5,6,7,8-tetrahydropyrrolo[1,2-a]pyridine-8-carboxylate,
methyl 3-m-methylthiobenzoyl-5,6,7,8-tetrahydropyrrolo[1,2-a]pyridine-8-carboxylate,
methyl 3-p-ethylthiobenzoyl-5,6,7,8-tetrahydropyrrolo[1,2-a]pyridine-8-carboxylate,
methyl 3-p-propylthiobenzoyl-5,6,7,8-tetrahydropyrrolo[1,2-a]pyridine-8-carboxylate,
methyl 3-p-isopropylthiobenzoyl-5,6,7,8-tetrahydropyrrolo[1,2-a]pyridine-8-carboxylate,
methyl 3-p-butylthiobenzoyl-5,6,7,8-tetrahydropyrrolo[1,2-a]pyridine-8-carboxylate,
methyl 3-p-isobutylthiobenzoyl-5,6,7,8-tetrahydropyrrolo[1,2-a]pyridine-8-carboxylate.

EXAMPLE 26

To a stirred solution of 3-p-methylthiobenzoyl-8-cyano-5,6,7,8-tetrahydropyrrolo[1,2-a]pyridine (2.0 g., 0.0067 moles) in chloroform (135 ml) cooled to −5°, in a nitrogen atmosphere, is added m-chloroperbenzoic acid (3.5 g., 85%, 0.02 moles). The reaction is stirred at this temperature for 1 hour, the solution is then washed with 10% sodium bicarbonate solution (2×50 ml.) and with water to neutrality. The extract is dried and evaporated in vacuo to give a product in 74% yield. Crystallization from acetone gives 3-p-methylsulfonylbenzoyl-8-cyano-5,6,7,8-tetrahydropyrrolo[1,2-a]pyridine, m.p. 199°–201°.

The resulting compound is hydrolyzed to the corresponding 8-carboxylic acid by following the procedure set forth in the second paragraph of Example 25 to give 3-p-methylsulfonylbenzoyl-5,6,7,8-tetrahydropyrrolo[1,2-a]pyridine-8-carboxylic acid, which when crystallized from acetone/ether gives crystals having a m.p. of 179°–180° C.

Similarly, by following in principle the procedure of this example but substituting other appropriate 3-alkylthiobenzoyl-8-cyano-5,6,7,8-tetrahydropyrrolo[1,2-a]pyridines for 3-p-methylthiobenzoyl-8-cyano-5,6,7,8-tetrahydropyrrolo[1,2-a]pyridine, e.g.

3-o-methylthiobenzoyl-8-cyano-5,6,7,8-tetrahydropyrrolo[1,2-a]pyridine,
3-m-methylthiobenzoyl-8-cyano-5,6,7,8-tetrahydropyrrolo[1,2-a]pyridine,
3-p-ethylthiobenzoyl-8-cyano-5,6,7,8-tetrahydropyrrolo[1,2-a]pyridine,
3-p-propylthiobenzoyl-8-cyano-5,6,7,8-tetrahydropyrrolo[1,2-a]pyridine,
3-p-isopropylthiobenzoyl-8-cyano-5,6,7,8-tetrahydropyrrolo[1,2-a]pyridine,
3-p-butylthiobenzoyl-8-cyano-5,6,7,8-tetrahydropyrrolo[1,2-a]pyridine, and
3-p-isobutylthiobenzoyl-8-cyano-5,6,7,8-tetrahydropyrrolo[1,2-a]pyridine, one obtains
3-o-methylsulfonylbenzoyl-5,6,7,8-tetrahydropyrrolo[1,2-a]pyridine-8-carboxylic acid,
3-m-methylsulfonylbenzoyl-5,6,7,8-tetrahydropyrrolo[1,2-a]pyridine-8-carboxylic acid,
3-p-ethylsulfonylbenzoyl-5,6,7,8-tetrahydropyrrolo[1,2-a]pyridine-8-carboxylic acid,
3-p-propylsulfonylbenzoyl-5,6,7,8-tetrahydropyrrolo[1,2-a]pyridine-8-carboxylic acid,
3-p-butylsulfonylbenzoyl-5,6,7,8-tetrahydropyrrolo[1,2-a]pyridine-8-carboxylic acid, and
3-p-isobutylsulfonylbenzoyl-5,6,7,8-tetrahydropyrrolo[1,2-a]pyridine-8-carboxylic acid.

By esterifying the above acids according to the process of Example 22, the corresponding methyl esters are obtained, such as
methyl 3-p-methylsulfonylbenzoyl-5,6,7,8-tetrahydropyrrolo[1,2-a]pyridine-8-carboxylate,
methyl 3-o-methylsulfonylbenzoyl-5,6,7,8-tetrahydropyrrolo[1,2-a]pyridine-8-carboxylate,
methyl 3-m-methylsulfonylbenzoyl-5,6,7,8-tetrahydropyrrolo[1,2-a]pyridine-8-carboxylate,
methyl 3-p-ethylsulfonylbenzoyl-5,6,7,8-tetrahydropyrrolo[1,2-a]pyridine-8-carboxylate,
methyl 3-p-propylsulfonylbenzoyl-5,6,7,8-tetrahydropyrrolo[1,2-a]pyridine-8-carboxylate,
methyl 3-p-butylsulfonylbenzoyl-5,6,7,8-tetrahydropyrrolo[1,2-a]pyridine-8-carboxylate, and
methyl 3-p-isobutylsulfonylbenzoyl-5,6,7,8-tetrahydropyrrolo[1,2-a]pyridine-8-carboxylate.

EXAMPLE 27

To a solution of 3-p-methylthiobenzoyl-5,6,7,8-tetrahydropyrrolo[1,2-a]pyridine-8-carboxylic acid (0.150 g.) in methanol (5 ml.) and tetrahydrofuran (2 ml.), cooled to 0°, is added sodium periodate (0.200 g.). After 18 hours at room temperature, the mixture is poured into water, the precipitated solid is collected by filtration, washed with water and dried. Crystallization of this material from dichloromethane-methanol gives 3-p-methylthiobenzoyl-5,6,7,8-tetrahydropyrrolo[1,2-a]pyridine-8-carboxylic acid, m.p. 201°–202° C.

Similarly, by following the procedure of this example, but substituting the other carboxylic acids prepared in Example 25 for 3-p-methylthiobenzoyl-5,6,7,8-tetrahydropyrrolo[1,2-a]pyridine-8-carboxylic acid the following compounds of this invention are obtained:
3-o-methylsulfinylbenzoyl-5,6,7,8-tetrahydropyrrolo[1,2-a]pyridine-8-carboxylic acid,
3-m-methylsulfinylbenzoyl-5,6,7,8-tetrahydropyrrolo[1,2-a]pyridine-8-carboxylic acid,
3-p-ethylsulfinylbenzoyl-5,6,7,8-tetrahydropyrrolo[1,2-a]pyridine-8-carboxylic acid,
3-p-propylsulfinylbenzoyl-5,6,7,8-tetrahydropyrrolo[1,2-a]pyridine-8-carboxylic acid,
3-p-butylsulfinylbenzoyl-5,6,7,8-tetrahydropyrrolo[1,2-a]pyridine-8-carboxylic acid, and
3-p-isobutylsulfinylbenzoyl-5,6,7,8-tetrahydropyrrolo[1,2-a]pyridine-8-carboxylic acid.

By esterifying the above acids according to the process of Example 22, the corresponding methyl esters are obtained, such as
methyl 3-p-methylsulfinylbenzoyl-5,6,7,8-tetrahydropyrrolo[1,2-a]pyridine-8-carboxylate,
methyl 3-o-methylsulfinylbenzoyl-5,6,7,8-tetrahydropyrrolo[1,2-a]pyridine-8-carboxylate,
methyl 3-m-methylsulfinylbenzoyl-5,6,7,8-tetrahydropyrrolo[1,2-a]pyridine-8-carboxylate,
methyl 3-p-ethylsulfinylbenzoyl-5,6,7,8-tetrahydropyrrolo[1,2-a]pyridine-8-carboxylate,
methyl 3-p-propylsulfinylbenzoyl-5,6,7,8-tetrahydropyrrolo[1,2-a]pyridine-8-carboxylate,
methyl 3-p-butylsulfinylbenzoyl-5,6,7,8-tetrahydropyrrolo[1,2-a]pyridine-8-carboxylate, and
methyl 3-p-isobutylsulfinylbenzoyl-5,6,7,8-tetrahydropyrrolo[1,2-a]pyridine-8-carboxylate.

EXAMPLE 28

A solution of 8-cyano-5,6,7,8-tetrahydropyrrolo[1,2-a]pyridine (5.0 g.) in ethanol (150 ml.) containing 85% potassium hydroxide (11.0 g.) and water (8 ml.) is heated at reflux temperature for 9 hours. The solvent is evaporated in vacuo, water (300 ml.) is added to the residue, and the solution is made acidic to pH-2 with hydrochloric acid. The product is extracted with ethyl acetate (3×100 ml.), the extract is washed with water, dried over sodium sulfate, and evaporated in vacuo. The residue is dissolved in dichloromethane and excess ethereal diazomethane is added. The solvent is evaporated, and the residue (4.80 g.) was chromatographed on a column of silica gel (250 g.). Hexane-ethyl acetate (95:5) removed methyl 5,6,7,8-tetrahydropyrrolo[1,2-a]pyridine-8-carboxylate (2.60 g., 51%) which is purified further for analysis by t.l.c. on silica gel using hexane-ether (1:1) as the developing solvent to give an oil having the following physical characteristics:

U.V.: 220 nm (ε 5890).
I.R.: (CHCl$_3$); 1726 cm$^{-1}$.
N.M.R.: (CDCl$_3$); 2.08 (m, 4H); 3.70 (s, 3H); 3.91 (m, 3H); 6.06 (m, 2H); 6.51 (m, 1H).

EXAMPLE 29

A solution of methyl-5,6,7,8-tetrahydropyrrolo[1,2-a]pyridine-8-carboxylate (2.0 g., 0.01 moles) in dry xylene (30 ml.) containing 4-fluorobenzoyl chloride (4.5 g., 0.028 moles) is heated at reflux temperature in a nitrogen atmosphere for 20 hours. The solvent is removed in vacuo and the residue is purified by t.l.c. on silica gel using hexane-ethyl acetate (3:1) as the developing solvent. Removal of the solvent gives methyl-3-p-fluorobenzoyl-5,6,7,8-tetrahydropyrrolo[1,2-a]pyridine-8-carboxylate which, when crystallized from acetone-hexane exhibits a m.p. of 78°–79° C.

A solution of the resulting methyl ester (1.5 g., 0.0049 moles) and potassium carbonate (1.4 g., 0.01 moles) in methanol (30 ml.) and water (10 ml.) is heated at reflux temperature for 2 hours. The methanol is removed in vacuo, water (25 ml.) is added to the residue and the resultant is extracted with ether (75 ml.). The aqueous phase is cooled to 5° and oxalic acid (3 g., 0.023 moles) is added. After agitation for 10 minutes the product is extracted into ethyl acetate (3×75 ml.). The extract is washed with water (3×100 ml.), dried, and evaporated in vacuo. The residue is crystallized from acetone-hexane to give 3-p-fluorobenzoyl-5,6,7,8-tetrahydropyrrolo[1,2-a]pyridine-8-carboxylic acid, m.p. 161°–162° C.

In like manner by substituting other benzoyl chlorides such as those set forth in Example 23 for p-fluorobenzoyl chloride, other compounds disclosed in Example 23 are prepared by this method.

EXAMPLE 30

In accordance with the method of Example 8, isopropyl 2-methyl-5,6,7,8-tetrahydropyrrolo[1,2-a]pyridine-8-carboxylate is condensed with N,N-dimethyl-p-toluamide, to produce isopropyl 3-p-toluoyl-2-methyl-5,6,7,8-tetrahydropyrrolo[1,2-a]pyridine-8-carboxylate (XI, R=CH$_3$, L=p-CH$_3$, R$^2$=iC$_3$H$_7$, n=1).

In like manner, condensing isopropyl 2-methyl-6,7,8,9-tetrahydro-5H-pyrrolo[1,2-a]azepine-9-carboxylate with N,N-dimethyl-p-toluamide there is obtained isopropyl 5-p-toluoyl-2-methyl-6,7,8,9-tetrahydro-5H-pyrrolo[1,2-a]azepine-1-carboxylate (XI, R=CH$_3$, L=p-CHR=iC$_3$H$_7^2$, n=2).

In a similar manner but using the N,N-dimethyl arylamides which correspond to the chlorides listed in Example 23 in place of N,N-dimethyl-p-toluamide, there are respectively obtained:

isopropyl 3-benzoyl-2-methyl-5,6,7,8-tetrahydropyrrolo[1,2-a]pyridine-8-carboxylate,
isopropyl 3-o-toluoyl-2-methyl-5,6,7,8-tetrahydropyrrolo[1,2-a]pyridine-8-carboxylate,
isopropyl 3-m-toluoyl-2-methyl-5,6,7,8-tetrahydropyrrolo[1,2-a]pyridine-8-carboxylate,
isopropyl 3-p-ethylbenzoyl-2-methyl-5,6,7,8-tetrahydropyrrolo[1,2-a]pyridine-8-carboxylate,
isopropyl 3-o-propylbenzoyl-2-methyl-5,6,7,8-tetrahydropyrrolo[1,2-a]pyridine-8-carboxylate,
isopropyl 3-m-butylbenzoyl-2-methyl-5,6,7,8-tetrahydropyrrolo[1,2-a]pyridine-8-carboxylate,
isopropyl 3-o-methoxybenzoyl-2-methyl-5,6,7,8-tetrahydropyrrolo[1,2-a]pyridine-8-carboxylate,
isopropyl 3-p-methoxybenzoyl-2-methyl-5,6,7,8-tetrahydropyrrolo[1,2-a]pyridine-8-carboxylate,
isopropyl 3-p-ethoxybenzoyl-2-methyl-5,6,7,8-tetrahydropyrrolo[1,2-a]pyridine-8-carboxylate,
isopropyl 3-p-isopropoxybenzoyl-2-methyl-5,6,7,8-tetrahydropyrrolo[1,2-a]pyridine-8-carboxylate,
isopropyl 3-o-chlorobenzoyl-2-methyl-5,6,7,8-tetrahydropyrrolo[1,2-a]pyridine-8-carboxylate,
isopropyl 3-m-chlorobenzoyl-2-methyl-5,6,7,8-tetrahydropyrrolo[1,2-a]pyridine-8-carboxylate,
isopropyl 3-p-chlorobenzoyl-2-methyl-5,6,7,8-tetrahydropyrrolo[1,2-a]pyridine-8-carboxylate,
isopropyl 3-o-fluorobenzoyl-2-methyl-5,6,7,8-tetrahydropyrrolo[1,2-a]pyridine-8-carboxylate,
isopropyl 3-p-fluorobenzoyl-2-methyl-5,6,7,8-tetrahydropyrrolo[1,2-a]pyridine-8-carboxylate,
isopropyl 3-m-bromobenzoyl-2-methyl-5,6,7,8-tetrahydropyrrolo[1,2-a]pyridine-8-carboxylate, and
isopropyl 3-o-bromobenzoyl-2-methyl-5,6,7,8-tetrahydropyrrolo[1,2-a]pyridine-8-carboxylate,
isopropyl 3-p-methylthiobenzoyl-5,6,7,8-tetrahydropyrrolo[1,2-a]pyridine-8-carboxylate,
isopropyl 3-o-ethylthiobenzoyl-5,6,7,8-tetrahydropyrrolo[1,2-a]pyridine-8-carboxylate,
isopropyl 3-m-propylthiobenzoyl-5,6,7,8-tetrahydropyrrolo[1,2-a]pyridine-8-carboxylate,
isopropyl 3-o-methylsulfinylbenzoyl-5,6,7,8-tetrahydropyrrolo[1,2-a]pyridine-8-carboxylate,
isopropyl 3-p-methylsulfinylbenzoyl-5,6,7,8-tetrahydropyrrolo[1,2-a]pyridine-8-carboxylate,
isopropyl 3-m-ethylsulfinylbenzoyl-5,6,7,8-tetrahydropyrrolo[1,2-a]pyridine-8-carboxylate,
isopropyl 3-p-butylsulfinylbenzoyl-5,6,7,8-tetrahydropyrrolo[1,2-a]pyridine-8-carboxylate,
isopropyl 3-o-ethylsulfonylbenzoyl-5,6,7,8-tetrahydropyrrolo[1,2-a]pyridine-8-carboxylate,
isopropyl 3-m-methylsulfonylbenzoyl-5,6,7,8-tetrahydropyrrolo[1,2-a]pyridine-8-carboxylate,
isopropyl 3-p-methylsulfonylbenzoyl-5,6,7,8-tetrahydropyrrolo[1,2-a]pyridine-8-carboxylate, and
isopropyl 3p-isopropylsulfonylbenzoyl-5,6,7,8-tetrahydropyrrolo[1,2-a]pyridine-8-carboxylate, and
isopropyl 3-benzoyl-2-methyl-6,7,8,9-tetrahydro-5H-pyrrolo[1,2-a]azepine-9-carboxylate,
isopropyl 3-o-toluoyl-2-methyl-6,7,8,9-tetrahydro-5H-pyrrolo[1,2-a]azepine-9-carboxylate,
isopropyl 3-m-toluoyl-2-methyl-6,7,8,9-tetrahydro-5H-pyrrolo[1,2-a]azepine-9-carboxylate,
isopropyl 3-p-ethylbenzoyl-2-methyl-6,7,8,9-tetrahydro-5H-pyrrolo[1,2-a]azepine-9-carboxylate,
isopropyl 3-o-propylbenzoyl-2-methyl-6,7,8,9-tetrahydro-5H-pyrrolo[1,2-a]azepine-9-carboxylate,
isopropyl 3-m-butylbenzoyl-2-methyl-6,7,8,9-tetrahydro-5H-pyrrolo[1,2-a]azepine-9-carboxylate,
isopropyl 3-o-methoxybenzoyl-2-methyl-6,7,8,9-tetrahydro-5H-pyrrolo[1,2-a]azepine-9-carboxylate,
isopropyl 3-p-methoxybenzoyl-2-methyl-6,7,8,9-tetrahydro-5H-pyrrolo[1,2-a]azepine-9-carboxylate,
isopropyl 3-p-ethoxybenzoyl-2-methyl-6,7,8,9-tetrahydro-5H-pyrrolo[1,2-a]azepine-9-carboxylate,
isopropyl 3-p-isopropoxybenzoyl-2-methyl-5,6,7,8-tetrahydropyrrolo[1,2-a]pyridine-8-carboxylate,
isopropyl 3-o-chlorobenzoyl-2-methyl-6,7,8,9-tetrahydro-5H-pyrrolo[1,2-a]azepine-9-carboxylate,
isopropyl 3-m-chlorobenzoyl-2-methyl-6,7,8,9-tetrahydro-5H-pyrrolo[1,2-a]azepine-9-carboxylate,
isopropyl 3-p-chlorobenzoyl-2-methyl-6,7,8,9-tetrahydro-5H-pyrrolo[1,2-a]azepine-9-carboxylate,
isopropyl 3-o-fluorobenzoyl-2-methyl-6,7,8,9-tetrahydro-5H-pyrrolo[1,2-a]azepine-9-carboxylate, isopropyl 3-p-fluorobenzoyl-2-methyl-6,7,8,9-tetrahydro-5H-pyrrolo[1,2-a]azepine-9-carboxylate,
isopropyl 3-m-bromobenzoyl-2-methyl-6,7,8,9-tetrahydro-5H-pyrrolo[1,2-a]azepine-9-carboxylate, and
isopropyl 3-p-bromobenzoyl-2-methyl-6,7,8,9-tetrahydro-5H-pyrrolo[1,2-a]azepine-9-carboxylate, and
isopropyl 3-p-methylthiobenzoyl-5,6,7,8-tetrahydro-5H-pyrrolo[1,2-a]azepine-8-carboxylate,
isopropyl 3-o-ethylthiobenzoyl-5,6,7,8-tetrahydro-5H-pyrrolo[1,2-a]azepine-8-carboxylate,
isopropyl 3-m-propylthiobenzoyl-5,6,7,8-tetrahydro-5H-pyrrolo[1,2-a]azepine-8-carboxylate,
isopropyl 3-o-methylsulfinylbenzoyl-5,6,7,8-tetrahydro-5H-pyrrolo[1,2-a]azepine-8-carboxylate,
isopropyl 3-p-methylsulfinylbenzoyl-5,6,7,8-tetrahydro-5H-pyrrolo[1,2-a]azepine-8-carboxylate,
isopropyl 3-m-ethylsulfinylbenzoyl-5,6,7,8-tetrahydro-5H-pyrrolo[1,2-a]azepine-8-carboxylate,
isopropyl 3-p-butylsulfinylbenzoyl-5,6,7,8-tetrahydro-5H-pyrrolo[1,2-a]azepine-8-carboxylate,
isopropyl 3-o-ethylsulfonylbenzoyl-5,6,7,8-tetrahydro-5H-pyrrolo[1,2-a]azepine-8-carboxylate,
isopropyl 3-m-methylsulfonylbenzoyl-5,6,7,8-tetrahydro-5H-pyrrolo[1,2-a]azepine-8-carboxylate,
isopropyl 3-p-methylsulfonylbenzoyl-5,6,7,8-tetrahydro-5H-pyrrolo[1,2-a]azepine-8-carboxylate, and
isopropyl 3-p-isopropylsulfonylbenzoyl-5,6,7,8-tetrahydro-5H-pyrrolo[1,2-a]azepine-8-carboxylate.

Likewise, the remaining final compounds obtained in Example 14 are converted into the corresponding 3-benzoyl substituted derivatives by reacting with N,N-dimethyl benzamide. Representative compounds thus obtained are:

isopropyl 3-benzoyl-2-ethyl-5,6,7,8-tetrahydropyrrolo[1,2-a]pyridine-8-carboxylate,
isopropyl 3-benzoyl-2-propyl-5,6,7,8-tetrahydropyrrolo[1,2-a]pyridine-8-carboxylate,
isopropyl 3-benzoyl-2-butyl-5,6,7,8-tetrahydropyrrolo[1,2-a]pyridine-8-carboxylate,
isopropyl 3-benzoyl-2-ethyl-5,6,7,8-tetrahydropyrrolo[1,2-a]azepine-8-carboxylate,
isopropyl 3-benzoyl-2-propyl-5,6,7,8-tetrahydropyrrolo[1,2-a]azepine-8-carboxylate,
ispropyl 3-benzoyl-2-butyl-5,6,7,8-tetrahydropyrrolo[1,2-a]azepine-8-carboxylate.

Other substituted benzoyl derivatives are obtained in accordance with this example employing other N,N-dimethylbenzamides corresponding to the chlorides listed in Example 23.

EXAMPLE 31

A solution of 500 mg. of isopropyl 5-p-toluoyl-2-methyl-5,6,7,8-tetrahydropyrrolo[1,2-a]pyridine-8-carboxylate in 15 ml.. of methanol is treated with a solution of 640 mg. of potassium carbonate in 7.5 ml. of water. The reaction mixture is refluxed under nitrogen atmosphere for 2 hours, cooled, and evaporated to dryness. Water is added to the residue and the solution is made acidic with 10% hydrochloric acid. The residue is 10% aqueous hydrochloric acid and 50 ml. of water. The resultant mixture is extracted with ethyl acetate (3×50 ml.). The combined extracts are dried over magnesium sulfate and evaporated to dryness under reduced pressure, to give 3-p-toluoyl-2-methyl-5,6,7,8-tetrahydropyrrolo[1,2-a]pyridine-8-carboxylic acid (XIa, R=CH$_3$, L=p-CH$_3$, n=1).

In like manner, by substituting isopropyl 5-p-toluoyl-2-methyl-6,7,8,9-tetrahydro-5H-pyrrolo[1,2-a]azepine-9-carboxylate for isopropyl 3-p-toluoyl-2-methyl-5,6,7,8-tetrahydropyrrolo[1,2-a]pyridine-8-carboxylate there is obtained 3-p-toluoyl-2-methyl-6,7,8,9-tetrahydro-5H-pyrrolo[1,2-a]azepine-9-carboxylic acid (XIa, R=CH$_3$, L=p-CH$_3$, n=2).

In a similar manner, or alternatively by the hydrolysis method of Example 10, the remaining isopropyl ester compounds obtained in Example 30 are converted into the corresponding free acids, namely:
3-benzoyl-2-methyl-5,6,7,8-tetrahydropyrrolo[1,2-a]pyridine-8-carboxylic acid,
3-o-toluoyl-2-methyl-5,6,7,8-tetrahydropyrrolo[1,2-a]pyridine-8-carboxylic acid,
3-m-toluoyl-2-methyl-5,6,7,8-tetrahydropyrrolo[1,2-a]pyridine-8-carboxylic acid,
3-p-ethylbenzoyl-2-methyl-5,6,7,8-tetrahydropyrrolo[1,2-a]pyridine-8-carboxylic acid,
3-o-propylbenzoyl-2-methyl-5,6,7,8-tetrahydropyrrolo[1,2-a]pyridine-8-carboxylic acid,
3-m-butylbenzoyl-2-methyl-5,6,7,8-tetrahydropyrrolo[1,2-a]pyridine-8-carboxylic acid,
3-o-methoxybenzoyl-2-methyl-5,6,7,8-tetrahydropyrrolo[1,2-a]pyridine-8-carboxylic acid,
3-p-methoxybenzoyl-2-methyl-5,6,7,8-tetrahydropyrrolo[1,2-a]pyridine-8-carboxylic acid,
3-p-ethoxybenzoyl-2-methyl-5,6,7,8-tetrahydropyrrolo[1,2-a]pyridine-8-carboxylic acid,
3-p-isopropoxybenzoyl-2-methyl-5,6,7,8-tetrahydropyrrolo[1,2-a]pyridine-8-carboxylic acid,
3-o-chlorobenzoyl-2-methyl-5,6,7,8-tetrahydropyrrolo[1,2-a]pyridine-8-carboxylic acid,
3-m-chlorobenzoyl-2-methyl-5,6,7,8-tetrahydropyrrolo[1,2-a]pyridine-8-carboxylic acid,
3-p-chlorobenzoyl-2-methyl-5,6,7,8-tetrahydropyrrolo[1,2-a]pyridine-8-carboxylic acid,
3-o-fluorobenzoyl-2-methyl-5,6,7,8-tetrahydropyrrolo[1,2-a]pyridine-8-carboxylic acid,
3-p-fluorobenzoyl-2-methyl-5,6,7,8-tetrahydropyrrolo[1,2-a]pyridine-8-carboxylic acid,
3-m-bromobenzoyl-2-methyl-5,6,7,8-tetrahydropyrrolo[1,2-a]pyridine-8-carboxylic acid,
3-p-bromobenzoyl-2-methyl-5,6,7,8-tetrahydropyrrolo[1,2-a]pyridine-8-carboxylic acid,
3-p-methylthiobenzoyl-2-methyl-5,6,7,8-tetrahydropyrrolo[1,2-a]pyridine-8-carboxylic acid,
3-o-ethylthiobenzoyl-2-methyl-5,6,7,8-tetrahydropyrrolo[1,2-a]pyridine-8-carboxylic acid,
3-m-propylthiobenzoyl-2-methyl-5,6,7,8-tetrahydropyrrolo[1,2-a]pyridine-8-carboxylic acid,
3-o-methylsulfinylbenzoyl-2-methyl-5,6,7,8-tetrahydropyrrolo[1,2-a]pyridine-8-carboxylic acid,
3-p-methylsulfinylbenzoyl-2-methyl-5,6,7,8-tetrahydropyrrolo[1,2-a]pyridine-8-carboxylic acid,
3-m-ethylsulfinylbenzoyl-2-methyl-5,6,7,8-tetrahydropyrrolo[1,2-a]pyridine-8-carboxylic acid,
3-p-butylsulfinylbenzoyl-2-methyl-5,6,7,8-tetrahydropyrrolo[1,2-a]pyridine-8-carboxylic acid,
3-o-ethylsulfonylbenzoyl-2-methyl-5,6,7,8-tetrahydropyrrolo[1,2-a]pyridine-8-carboxylic acid,
3-m-methylsulfonylbenzoyl-2-methyl-5,6,7,8-tetrahydropyrrolo[1,2-a]pyridine-8-carboxylic acid,
3-p-methylsulfonylbenzoyl-2-methyl-5,6,7,8-tetrahydropyrrolo[1,2-a]pyridine-8-carboxylic acid, and
3-p-isopropylsulfonylbenzoyl-2-methyl-5,6,7,8-tetrahydropyrrolo[1,2-a]pyridine-8-carboxylic acid;
3-benzoyl-2-methyl-6,7,8,9-tetrahydro-5H-pyrrolo[1,2-a]azepine-9-carboxylic acid, 3-o-toluoyl-2-methyl-6,7,8,9-tetrahydro-5H-pyrrolo[1,2-a]azepine-9-carboxylic acid,
3-m-toluoyl-2-methyl-6,7,8,9-tetrahydro-5H-pyrrolo[1,2-a]azepine-9-carboxylic acid,
3-p-ethylbenzoyl-2-methyl-6,7,8,9-tetrahydro-5H-pyrrolo[1,2-a]azepine-9-carboxylic acid,
3-o-propylbenzoyl-2-methyl-6,7,8,9-tetrahydro-5H-pyrrolo[1,2-a]azepine-9-carboxylic acid,
3-m-butylbenzoyl-2-methyl-6,7,8,9-tetrahydro-5H-pyrrolo[1,2-a]azepine-9-carboxylic acid,
3-o-methoxybenzoyl-2-methyl-6,7,8,9-tetrahydro-5H-pyrrolo[1,2-a]azepine-9-carboxylic acid,
3-p-methoxybenzoyl-2-methyl-6,7,8,9-tetrahydro-5H-pyrrolo[1,2-a]azepine-9-carboxylic acid,
3-p-ethoxybenzoyl-2-methyl-6,7,8,9-tetrahydro-5H-pyrrolo[1,2-a]azepine-9-carboxylic acid,
3-p-isopropoxybenzoyl-2-methyl-6,7,8,9-tetrahydro-5H-pyrrolo[1,2-a]azepine-9-carboxylic acid,
3-o-chlorobenzoyl-2-methyl-6,7,8,9-tetrahydro-5H-pyrrolo[1,2-a]azepine-9-carboxylic acid,
3-m-chlorobenzoyl-2-methyl-6,7,8,9-tetrahydro-5H-pyrrolo[1,2-a]azepine-9-carboxylic acid,
3-p-chlorobenzoyl-2-methyl-6,7,8,9-tetrahydro-5H-pyrrolo[1,2-a]azepine-9-carboxylic acid,
3-o-fluorobenzoyl-2-methyl-6,7,8,9-tetrahydro-5H-pyrrolo[1,2-a]azepine-9-carboxylic acid,
3-p-fluorobenzoyl-2-methyl-6,7,8,9-tetrahydro-5H-pyrrolo[1,2-a]azepine-9-carboxylic acid,
3-m-bromobenzoyl-2-methyl-6,7,8,9-tetrahydro-5H-pyrrolo[1,2-a]azepine-9-carboxylic acid,
3-p-bromobenzoyl-2-methyl-6,7,8,9-tetrahydro-5H-pyrrolo[1,2-a]azepine-9-carboxylic acid,
3-p-methylthiobenzoyl-2-methyl-5,6,7,8-tetrahydropyrrolo[1,2-a]azepine-9-carboxylic acid,
3-o-ethylthiobenzoyl-2-methyl-5,6,7,8-tetrahydropyrrolo[1,2-a]azepine-9-carboxylic acid,
3-m-propylthiobenzoyl-2-methyl-5,6,7,8-tetrahydropyrrolo[1,2-a]azepine-9-carboxylic acid,
3-o-methylsulfinylbenzoyl-2-methyl-5,6,7,8-tetrahydropyrrolo[1,2-a]azepine-9-carboxylic acid,
3-p-methylsulfinylbenzoyl-2-methyl-5,6,7,8-tetrahydropyrrolo[1,2-a]azepine-9-carboxylic acid,
3-m-ethylsulfinylbenzoyl-2-methyl-5,6,7,8-tetrahydropyrrolo[1,2-a]azepine-9-carboxylic acid,
3-p-butylsulfinylbenzoyl-2-methyl-5,6,7,8-tetrahydropyrrolo[1,2-a]azepine-9-carboxylic acid,
3-o-ethylsulfonylbenzoyl-2-methyl-5,6,7,8-tetrahydropyrrolo[1,2-a]azepine-9-carboxylic acid,
3-m-methylsulfonylbenzoyl-2-methyl-5,6,7,8-tetrahydropyrrolo[1,2-a]azepine-9-carboxylic acid,
3-p-methylsulfonylbenzoyl-2-methyl-5,6,7,8-tetrahydropyrrolo[1,2-a]azepine-9-carboxylic acid, and
3-p-isopropylsulfonylbenzoyl-2-methyl-5,6,7,8-tetrahydropyrrolo[1,2-a]azepine-9-carboxylic acid.

Similarly, the corresponding 2-ethyl, 2-propyl and 2-butyl substituted 3-aroyl-2-methyl-5,6,7,8-tetrahydropyrrolo[1,2-a]pyridine-8-carboxylic acids and 3-aroyl-6,7,8,9-tetrahydropyrrolo[1,2-a]azepine-9-carboxylic acids of Example 25 are prepared.

EXAMPLE 32

A 50% suspension of sodium hydride in mineral oil is washed with anhydrous hexane under an atmosphere of nitrogen, and then suspended in dimethylformamide. The suspension is cooled to −5° C. and 4.5 g. of methyl N-(3-methanesulfonyloxypropyl)-3-carbomethoxypyrrol-2-acetate are added, stirring the reaction mixture at −5° to 0° C. for 1 hour. The reaction mixture is then poured into iced sodium chloride solution and extracted several times with benzene. The combined extracts are washed with water, dried and evaporated to dryness under reduced pressure. The solid residue is crystallized from ether, thus obtaining dimethyl 5,6,7,8-tetrahydropyrrolo[1,2-a]pyridine-1,8-dicarboxylate (VII, R=H, n=1) identical to the product obtained in Example 4.

In like manner, by substituting methyl N-(3-mesyloxybutyl)-3-carbomethoxypyrrole-2-acetate for methyl N-(3-mesyloxybutyl)-3-carbomethoxypyrrole-2-acetate there is obtained dimethyl 6,7,8,9-tetrahydro-5H-pyrrolo[1,2-a]azepine-1,9-dicarboxylate (VII, R=H, n=2).

EXAMPLE 33

A solution of 150 mg. of N,N-dimethylthiophene-2-carboxamide and 0.088 ml. of phosphorous oxychloride in 10 ml. of 1,2-dichloroethane is refluxed for 1 hour. To this solution is added a solution of 100 mg. of isopropyl 5,6,7,8-tetrahydropyrrolo[1,2-a]pyridine-8-carboxylate. The reaction mixture is refluxed under an argon atmosphere for 3 hours, treated with 657 mg. of sodium acetate trihydrate in 5 ml. of water and refluxed for a further 9–10 hours. The organic phase was separated, washed with saturated salt solution, dried over sodium sulfate and evaporated in vacuo. The residue is chromatographed on 12 g. of silica gel, eluting with hexane:ethyl acetate (90:10), thus obtaining isopropyl 3-(2-thenoyl)-5,6,7,8-tetrahydropyrrolo[1,2-a]pyridine-8-carboxylate (XII, R and M=H, $R^2$=i$C_3H_7$, X=S, n=1), m.p. 113° C. after crystallization from acetone-hexane.

In like manner, substituting isopropyl 6,7,8,9-tetrahydro-5H-pyrrolo[1,2-a]azepine-9-carboxylate for isopropyl 5,6,7,8-tetrahydropyrrolo[1,2-a]pyridine-8-carboxylate there is obtained isopropyl 3-(2-thenoyl)-6,7,8,9-tetrahydro-5H-pyrrolo[1,2-a]azepine-9-carboxylate (XII, R and M=H, $R^2$=i$C_3H_7$, X=S, n=2).

EXAMPLE 34

A solution of 225 mg. of isopropyl 3-(2-thenoyl)-5,6,7,8-tetrahydropyrrolo[1,2-a]pyridine-8-carboxylate in 10 ml. of methanol containing potassium carbonate (200 mg.) and water (1 ml.) is heated at reflux temperature for 4 hours. The solvent is removed in vacuo, water is added to the residue and neutral materials are removed by extraction with ethyl acetate. The aqueous alkaline phase is acidified with hydrochloric acid and extracted three times with ethyl acetate. The extracts are dried over sodium sulfate and evaporated to dryness under reduced pressure, thus obtaining 3-(2-thenoyl)-5,6,7,8-tetrahydropyrrolo[1,2-a]pyridine-8-carboxylic acid, (XIIa, R and M=H, X=S, n=1), m.p. 145°–146° after crystallization from ethanol-ether-hexane.

In like manner, substituting isopropyl 5-(2-thenoyl)-6,7,8,9-tetrahydro-5H-pyrrolo[1,2-a]azepine-9-carboxylate for isopropyl 3-(2-thenoyl)-5,6,7,8-tetrahydropyrrolo[1,2-a]pyridine-8-carboxylate there is obtained 3-(2-thenoyl)-6,7,8,9-tetrahydro-5H-pyrrolo[1,2-a]azepine-9-carboxylic acid (XIIa, R and M=H, X=S, n=2).

EXAMPLE 35

By following the methods of Examples 6, the remaining compounds obtained in Example 5 are converted respectively into:
methyl 5,6,7,8-tetrahydropyrrolo[1,2-a]pyridine-8-carboxylate, ethyl 5,6,7,8-tetrahydropyrrolo[1,2-a]pyridine-8-carboxylate,
propyl 5,6,7,8-tetrahydropyrrolo[1,2-a]pyridine-8-carboxylate and
butyl 5,6,7,8-tetrahydropyrrolo[1,2-a]pyridine-8-carboxylate; and
methyl 6,7,8,9-tetrahydro-5H-pyrrolo[1,2-a]azepine-9-carboxylate,
ethyl 6,7,8,9-tetrahydro-5H-pyrrolo[1,2-a]azepine-9-carboxylate,
propyl 6,7,8,9-tetrahydro-5H-pyrrolo[1,2-a]azepine-9-carboxylate, and
butyl 6,7,8,9-tetrahydro-5H-pyrrolo[1,2-a]azepine-9-carboxylate.

Upon condensation of these compounds with N,N-dimethylthiophene-2-carboxamide, in accordance with the method of Example 33 there are respectively obtained:
methyl 3-(2-thenoyl)-5,6,7,8-tetrahydropyrrolo[1,2-a]pyridine-8-carboxylate,
ethyl 3-(2-thenoyl)-5,6,7,8-tetrahydropyrrolo[1,2-a]pyridine-8-carboxylate,
propyl 3-(2-thenoyl)-5,6,7,8-tetrahydropyrrolo[1,2-a]pyridine-8-carboxylate and
butyl 3-(2-thenoyl)-5,6,7,8-tetrahydropyrrolo[1,2-a]pyridine-8-carboxylate; and
methyl 3-(2-thenoyl)-6,7,8,9-tetrahydro-5H-pyrrolo[1,2-a]azepine-9-carboxylate,
ethyl 3-(2-thenoyl)-6,7,8,9-tetrahydro-5H-pyrrolo[1,2-a]azepine-9-carboxylate,
propyl 3-(2-thenoyl)-6,7,8,9-tetrahydro-5H-pyrrolo[1,2-a]azepine-9-carboxylate and
butyl 3-(2-thenoyl)-6,7,8,9-tetrahydro-5H-pyrrolo[1,2-a]azepine-9-carboxylate.

EXAMPLE 36

Following the procedure of Example 33, using 1.1 to 2 molar equivalents of
N,N-dimethylfuran-2-carboxamide,
N,N-dimethyl-3-methylthiophene-2-carboxamide,
N,N-dimethyl-4-methylthiophene-2-carboxamide,
N,N-dimethyl-5-methylthiophene-2-carboxamide,
N,N-dimethyl-4-chlorothiophene-2-carboxamide,
N,N-dimethyl-5-chlorothiophene-2-carboxamide,
N,N-dimethyl-3-bromothiophene-2-carboxamide,
N,N-dimethyl-4-bromothiophene-2-carboxamide,
N,N-dimethyl-5-bromothiophene-2-carboxamide,
N,N-dimethyl-3-methylfuran-2-carboxamide,
N,N-dimethyl-4-methylfuran-2-carboxamide,
N,N-dimethyl-5-methylfuran-2-carboxamide,
N,N-dimethyl-3-chlorofuran-2-carboxamide,
N,N-dimethyl-4-chlorofuran-2-carboxamide,
N,N-dimethyl-5-chlorofuran-2-carboxamide,
N,N-dimethyl-4-bromofuran-2-carboxamide and
N,N-dimethyl-5-bromofuran-2-carboxamide,
in place of N,N-dimethylthiophene-2-carboxamide, and monitoring the course of the reaction by t.l.c., there are obtained respectively:
isopropyl 3-(2-furoyl)-5,6,7,8-tetrahydropyrrolo[1,2-a]pyridine-8-carboxylate,
isopropyl 3-(3-methyl-2-thenoyl)-5,6,7,8-tetrahydropyrrolo[1,2-a]pyridine-8-carboxylate,
isopropyl 3-(4-methyl-2-thenoyl)-5,6,7,8-tetrahydropyrrolo[1,2-a]pyridine-8-carboxylate,
isopropyl 3-(5-methyl-2-thenoyl)-5,6,7,8-tetrahydropyrrolo[1,2-a]pyridine-8-carboxylate,
isopropyl 3-(4-chloro-2-thenoyl)-5,6,7,8-tetrahydropyrrolo[1,2-a]pyridine-8-carboxylate,
isopropyl 3-(5-chloro-2-thenoyl)-5,6,7,8-tetrahydropyrrolo[1,2-a]pyridine-8-carboxylate,
isopropyl 3-(3-bromo-2-thenoyl)-5,6,7,8-tetrahydropyrrolo[1,2-a]pyridine-8-carboxylate,
isopropyl 3-(4-bromo-2-thenoyl)-5,6,7,8-tetrahydropyrrolo[1,2-a]pyridine-8-carboxylate,
isopropyl 3-(5-bromo-2-thenoyl)-5,6,7,8-tetrahydropyrrolo[1,2-a]pyridine-8-carboxylate,
isopropyl 3-(3-methyl-2-furoyl)-5,6,7,8-tetrahydropyrrolo[1,2-a]pyridine-8-carboxylate,
isopropyl 3-(4-methyl-2-furoyl)-5,6,7,8-tetrahydropyrrolo[1,2-a]pyridine-8-carboxylate,
isopropyl 3-(5-methyl-2-furoyl)-5,6,7,8-tetrahydropyrrolo[1,2-a]pyridine-8-carboxylate,
isopropyl 5-(3-chloro-2-furoyl)-5,6,7,8-tetrahydropyrrolo[1,2-a]pyridine-8-carboxylate,
isopropyl 3-(4-chloro-2-furoyl)-5,6,7,8-tetrahydropyrrolo[1,2-a]pyridine-8-carboxylate,
isopropyl 3-(5-chloro-2-furoyl)-5,6,7,8-tetrahydropyrrolo[1,2-a]pyridine-8-carboxylate,
isopropyl 3-(4-bromo-2-furoyl)-5,6,7,8-tetrahydropyrrolo[1,2-a]pyridine-8-carboxylate and
isopropyl 3-(5-bromo-2-furoyl)-5,6,7,8-tetrahydropyrrolo[1,2-a]pyridine-8-carboxylate; and
isopropyl 3-(2-furoyl)-6,7,8,9-tetrahydro-5H-pyrrolo[1,2-a]azepine-9-carboxylate,
isopropyl 3-(3-methyl-2-thenoyl)-6,7,8,9-tetrahydro-5H-pyrrolo[1,2-a]azepine-9-carboxylate,
isopropyl 2-(4-methyl-2-thenoyl)-6,7,8,9-tetrahydro-5H-pyrrolo[1,2-a]azepine-9-carboxylate,
isopropyl 3-(5-methyl-2-thenoyl)-6,7,8,9-tetrahydro-5H-pyrrolo[1,2-a]azepine-9-carboxylate,
isopropyl 2-(4-chloro-2-thenoyl)-6,7,8,9-tetrahydro-5H-pyrrolo[1,2-a]azepine-9-carboxylate,
isopropyl 3-(5-chloro-2-thenoyl)-6,7,8,9-tetrahydro-5H-pyrrolo[1,2-a]azepine-9-carboxylate,
isopropyl 3-(3-bromo-2-thenoyl)-6,7,8,9-tetrahydro-5H-pyrrolo[1,2-a]azepine-9-carboxylate,
isopropyl 3-(4-bromo-2-thenoyl)-6,7,8,9-tetrahydro-5H-pyrrolo[1,2-a]azepine-9-carboxylate,
isopropyl 3-(5-bromo-2-thenoyl)-6,7,8,9-tetrahydro-5H-pyrrolo[1,2-a]azepine-9-carboxylate,
isopropyl 3-(3-methyl-2-furoyl)-6,7,8,9-tetrahydro-5H-pyrrolo[1,2-a]azepine-9-carboxylate,
isopropyl 3-(4-methyl-2-furoyl)-6,7,8,9-tetrahydro-5H-pyrrolo[1,2-a]azepine-2-carboxylate,
isopropyl 3-(5-methyl-2-furoyl)-6,7,8,9-tetrahydro-5H-pyrrolo[1,2-a]azepine-9-carboxylate,
isopropyl 5-(3-chloro-2-furoyl)-6,7,8,9-tetrahydro-5H-pyrrolo[1,2-a]azepine-9-carboxylate,
isopropyl 3-(4-chloro-2-furoyl)-6,7,8,9-tetrahydro-5H-pyrrolo[1,2-a]azepine-9-carboxylate,
isopropyl 3-(5-chloro-2-furoyl)-6,7,8,9-tetrahydro-5H-pyrrolo[1,2-a]azepine-9-carboxylate,
isopropyl 3-(4-bromo-2-furoyl)-6,7,8,9-tetrahydro-5H-pyrrolo[1,2-a]azepine-9-carboxylate and
isopropyl 3-(5-bromo-2-furoyl)-6,7,8,9-tetrahydro-5H-pyrrolo[1,2-a]azepine-9-carboxylate.

Upon hydrolysis of the isopropyl ester group, in accordance with the methods of Examples 20 or 21, there are obtained the corresponding free acids, namely:
3-(2-furoyl)-5,6,7,8-tetrahydropyrrolo[1,2-a]pyridine-8-carboxylic acid,
3-(3-methyl-2-thenoyl)-5,6,7,8-tetrahydropyrrolo[1,2-a]pyridine-8-carboxylic acid,
3-(4-methyl-2-thenoyl)-5,6,7,8-tetrahydropyrrolo[1,2-a]pyridine-8-carboxylic acid, 3-(5-methyl-2-thenoyl)-5,6,7,8-tetrahydropyrrolo[1,2-a]pyridine-8-carboxylic acid,
3-(4-chloro-2-thenoyl)-5,6,7,8-tetrahydropyrrolo[1,2-a]pyridine-8-carboxylic acid,
3-(5-chloro-2-thenoyl)-5,6,7,8-tetrahydropyrrolo[1,2-a]pyridine-8-carboxylic acid,
3-(3-bromo-2-thenoyl)-5,6,7,8-tetrahydropyrrolo[1,2-a]pyridine-8-carboxylic acid,
3-(4-bromo-2-thenoyl)-5,6,7,8-tetrahydropyrrolo[1,2-a]pyridine-8-carboxylic acid,
3-(5-bromo-2-thenoyl)-5,6,7,8-tetrahydropyrrolo[1,2-a]pyridine-8-carboxylic acid,
3-(3-methyl-2-furoyl)-5,6,7,8-tetrahydropyrrolo[1,2-a]pyridine-8-carboxylic acid,
3-(4-methyl-2-furoyl)-5,6,7,8-tetrahydropyrrolo[1,2-a]pyridine-8-carboxylic acid,
3-(5-methyl-2-furoyl)-5,6,7,8-tetrahydropyrrolo[1,2-a]pyridine-8-carboxylic acid,
3-(3-chloro-2-furoyl)-5,6,7,8-tetrahydropyrrolo[1,2-a]pyridine-8-carboxylic acid,
3-(4-chloro-2-furoyl)-5,6,7,8-tetrahydropyrrolo[1,2-a]pyridine-8-carboxylic acid,
3-(5-chloro-2-furoyl)-5,6,7,8-tetrahydropyrrolo[1,2-a]pyridine-8-carboxylic acid,
3-(4-bromo-2-furoyl)-5,6,7,8-tetrahydropyrrolo[1,2-a]pyridine-8-carboxylic acid, and
3-(5-bromo-2-furoyl)-5,6,7,8-tetrahydropyrrolo[1,2-a]pyridine-8-carboxylic acid; and
3-(2-furoyl)-6,7,8,9-tetrahydro-5H-pyrrolo[1,2-a]azepine-9-carboxylic acid,
3-(3-methyl-2-thenoyl)-6,7,8,9-tetrahydro-5H-pyrrolo[1,2-a]azepine-9-carboxylic acid,
3-(4-methyl-2-thenoyl)-6,7,8,9-tetrahydro-5H-pyrrolo[1,2-a]azepine-9-carboxylic acid,
3-(5-methyl-2-thenoyl)-6,7,8,9-tetrahydro-5H-pyrrolo[1,2-a]azepine-9-carboxylic acid,
3-(4-chloro-2-thenoyl)-6,7,8,9-tetrahydro-5H-pyrrolo[1,2-a]azepine-9-carboxylic acid,
3-(5-chloro-2-thenoyl)-6,7,8,9-tetrahydro-5H-pyrrolo[1,2-a]azepine-9-carboxylic acid,
3-(3-bromo-2-thenoyl)-6,7,8,9-tetrahydro-5H-pyrrolo[1,2-a]azepine-9-carboxylic acid,
3-(4-bromo-2-thenoyl)-6,7,8,9-tetrahydro-5H-pyrrolo[1,2-a]azepine-9-carboxylic acid,
3-(5-bromo-2-thenoyl)-6,7,8,9-tetrahydro-5H-pyrrolo[1,2-a]azepine-9-carboxylic acid,
3-(3-methyl-2-furoyl)-6,7,8,9-tetrahydro-5H-pyrrolo[1,2-a]azepine-9-carboxylic acid,
3-(4-methyl-2-furoyl)-6,7,8,9-tetrahydro-5H-pyrrolo[1,2-a]azepine-9-carboxylic acid,
3-(5-methyl-2-furoyl)-6,7,8,9-tetrahydro-5H-pyrrolo[1,2-a]azepine-9-carboxylic acid,
3-(3-chloro-2-furoyl)-6,7,8,9-tetrahydro-5H-pyrrolo[1,2-a]azepine-9-carboxylic acid,
3-(4-chloro-2-furoyl)-6,7,8,9-tetrahydro-5H-pyrrolo[1,2-a]azepine-9-carboxylic acid,
3-(5-chloro-2-furoyl)-6,7,8,9-tetrahydro-5H-pyrrolo[1,2-a]azepine-9-carboxylic acid,
3-(4-bromo-2-furoyl)-6,7,8,9-tetrahydro-5H-pyrrolo[1,2-a]azepine-9-carboxylic acid,
3-(5-bromo-2-furoyl)-6,7,8,9-tetrahydro-5H-pyrrolo[1,2-a]azepine-9-carboxylic acid.

EXAMPLE 37

In accordance with the method of Example 33, isopropyl 2-methyl-5,6,7,8-tetrahydropyrrolo[1,2-a]pyridine-8-carboxylate is condensed with N,N-dimethylthiophene-2-carboxamide to produce isopropyl 3-(2-thenoyl)-2-methyl-5,6,7,8-tetrahydropyrrolo[1,2-a]pyridine-8-carboxylate (XII, R=CH$_3$, M=H, R$^2$=iC$_3$H$_7$, X=S, n=1).

In like manner substituting isopropyl 2-methyl-6,7,8,9-tetrahydro-5H-pyrrolo[1,2-a]azepine-9-carboxylate for isopropyl 2-methyl-5,6,7,8-tetrahydropyrrolo[1,2-a]pyrimidine-8-carboxylate there is obtained isopropyl 2-methyl-6,7,8,9-tetrahydro-5H-pyrrolo[1,2-a]azepine-9-carboxylate (XII, R=CH$_3$, M=H, R$^2$=iC$_3$H$_7$, n=2).

In a similar manner but using the N,N-dimethylthiophene- or furan-2-carboxamides listed in Example 32 in place of N,N-dimethylthiophene-2-carboxamide, there are respectively obtained:
isopropyl 3-(2-furoyl)-2-methyl-5,6,7,8-tetrahydropyrrolo[1,2-a]pyridine-8-carboxylate,
isopropyl 3-(3-methyl-2-thenoyl)-2-methyl-5,6,7,8-tetrahydropyrrolo[1,2-a]pyridine-8-carboxylate,
isopropyl 3-(4-methyl-2-thenoyl)-2-methyl-5,6,7,8-tetrahydropyrrolo[1,2-a]pyridine-8-carboxylate,
isopropyl 3-(5-methyl-2-thenoyl)-2-methyl-5,6,7,8-tetrahydropyrrolo[1,2-a]pyridine-8-carboxylate,
isopropyl 3-(4-chloro-2-thenoyl)-2-methyl-5,6,7,8-tetrahydropyrrolo[1,2-a]pyridine-8-carboxylate,
isopropyl 3-(5-chloro-2-thenoyl)-2-methyl-5,6,7,8-tetrahydropyrrolo[1,2-a]pyridine-8-carboxylate,
isopropyl 3-(3-bromo-2-thenoyl)-2-methyl-5,6,7,8-tetrahydropyrrolo[1,2-a]pyridine-8-carboxylate,
isopropyl 3-(4-bromo-2-thenoyl)-2-methyl-5,6,7,8-tetrahydropyrrolo[1,2-a]pyridine-8-carboxylate,
isopropyl 3-(5-bromo-2-thenoyl)-2-methyl-5,6,7,8-tetrahydropyrrolo[1,2-a]pyridine-8-carboxylate,
isopropyl 3-(3-methyl-2-furoyl)-2-methyl-5,6,7,8-tetrahydropyrrolo[1,2-a]pyridine-8-carboxylate,
isopropyl 3-(4-methyl-2-furoyl)-2-methyl-5,6,7,8-tetrahydropyrrolo[1,2-a]pyridine-8-carboxylate,
isopropyl 3-(5-methyl-2-furoyl)-2-methyl-5,6,7,8-tetrahydropyrrolo[1,2-a]pyridine-8-carboxylate,
isopropyl 3-(3-chloro-2-furoyl)-2-methyl-5,6,7,8-tetrahydropyrrolo[1,2-a]pyridine-8-carboxylate,
isopropyl 3-(4-chloro-2-furoyl)-2-methyl-5,6,7,8-tetrahydropyrrolo[1,2-a]pyridine-8-carboxylate,
isopropyl 3-(5-chloro-2-furoyl)-2-methyl-5,6,7,8-tetrahydropyrrolo[1,2-a]pyridine-8-carboxylate,
isopropyl 3-(4-bromo-2-furoyl)-2-methyl-5,6,7,8-tetrahydropyrrolo[1,2-a]pyridine-8-carboxylate and
isopropyl 3-(4-bromo-2-furoyl)-2-methyl-5,6,7,8-tetrahydropyrrolo[1,2-a]pyridine-8-carboxylate,
isopropyl 3-(5-bromo-2-furoyl)-2-methyl-5,6,7,8-tetrahydropyrrolo[1,2-a]pyridine-8-carboxylate; and
isopropyl 3-(2-furoyl)-2-methyl-6,7,8,9-tetrahydro-5H-pyrrolo[1,2-a]azepine-9-carboxylate,
isopropyl 3-(3-methyl-2-thenoyl)-2-methyl-6,7,8,9-tetrahydro-5H-pyrrolo[1,2-a]azepine-9-carboxylate,
isopropyl 3-(4-methyl-2-thenoyl)-2-methyl-6,7,8,9-tetrahydro-5H-pyrrolo[1,2-a]azepine-9-carboxylate,
isopropyl 3-(5-methyl-2-thenoyl)-2-methyl-6,7,8,9-tetrahydro-5H-pyrrolo[1,2-a]azepine-9-carboxylate,
isopropyl 3-(4-chloro-2-thenoyl)-2-methyl-6,7,8,9-tetrahydro-5H-pyrrolo[1,2,-a]azepine-9-carboxylate,
isopropyl 3-(5-chloro-2-thenoyl)-2-methyl-6,7,8,9-tetrahydro-5H-pyrrolo[1,2-a]azepine-9-carboxylate,
isopropyl 3-(3-bromo-2-thenoyl)-2-methyl-6,7,8,9-tetrahydro-5H-pyrrolo[1,2-a]azepine-9-carboxylate,
isopropyl 3-(4-bromo-2-thenoyl)-2-methyl-6,7,8,9-tetrahydro-5H-pyrrolo[1,2-a]azepine-9-carboxylate,
isopropyl 3-(5-bromo-2-thenoyl)-2-methyl-6,7,8,9-tetrahydro-5H-pyrrolo[1,2-a]azepine-9-carboxylate, isopropyl 3-(3-methyl-2-furoyl)-2-methyl-6,7,8,9-tetrahydro-5H-pyrrolo[1,2-a]azepine-9-carboxylate,
isopropyl 3-(4-methyl-2-furoyl)-2-methyl-6,7,8,9-tetrahydro-5H-pyrrolo[1,2-a]azepine-9-carboxylate,
isopropyl 3-(5-methyl-2-furoyl)-2-methyl-6,7,8,9-tetrahydro-5H-pyrrolo[1,2-a]azepine-9-carboxylate,
isopropyl 3-(3-chloro-2-furoyl)-2-methyl-6,7,8,9-tetrahydro-5H-pyrrolo[1,2-a]azepine-9-carboxylate,
isopropyl 3-(4-chloro-2-furoyl)-2-methyl-6,7,8,9-tetrahydro-5H-pyrrolo[1,2-a]azepine-9-carboxylate,
isopropyl 3-(5-chloro-2-furoyl)-2-methyl-6,7,8,9-tetrahydro-5H-pyrrolo[1,2-a]azepine-9-carboxylate,
isopropyl 3-(4-bromo-2-furoyl)-2-methyl-6,7,8,9-tetrahydro-5H-pyrrolo[1,2-a]azepine-9-carboxylate and
isopropyl 3-(4-bromo-2-furoyl)-2-methyl-6,7,8,9-tetrahydro-5H-pyrrolo[1,2-a]azepine-9-carboxylate,
isopropyl 3-(5-bromo-2-furoyl)-2-methyl-6,7,8,9-tetrahydro-5H-pyrrolo[1,2-a]azepine-9-carboxylate.

Likewise, the remaining final compounds obtained in Example 13 are converted into the corresponding 5-furoyl or thenoyl substituted derivatives. Representative compounds thus obtained are:
isopropyl 3-(2-thenoyl)-2-ethyl-5,6,7,8-tetrahydropyrrolo[1,2-a]pyridine-8-carboxylate,
isopropyl 3-(2-furoyl)-2-propyl-5,6,7,8-tetrahydropyrrolo[1,2-a]pyridine-8-carboxylate,
isopropyl 3-(3-methyl-2-thenoyl)-2-butyl-5,6,7,8-tetrahydropyrrolo[1,2-a]pyridine-8-carboxylate,
isopropyl 3-(4-chloro-2-thenoyl)-2-ethyl-5,6,7,8-tetrahydropyrrolo[1,2-a]pyridine-8carboxylate,
isopropyl 3-(5-methyl-2-furoyl)-2-propyl-5,6,7,8-tetrahydropyrrolo[1,2-a]pyridine-8-carboxylate and
isopropyl 3-(3-chloro-2-furoyl)-2-butyl-5,6,7,8-tetrahydropyrrolo[1,2-a]pyridine-8-carboxylate; and
isopropyl 3-(2-thenoyl)-2-ethyl-6,7,8,9-tetrahydro-5H-pyrrolo[1,2-a]azepine-9-carboxylate,
isopropyl 3-(2-furoyl)-2-propyl-6,7,8,9-tetrahydro-5H-pyrrolo[1,2-a]azepine-9-carboxylate,
isopropyl 3-(3-methyl-2-thenoyl)-2-butyl-6,7,8,9-tetrahydro-5H-pyrrolo[1,2-a]azepine-9-carboxylate,
isopropyl 3-(4-chloro-2-thenoyl)-2-ethyl-6,7,8,9-tetrahydro-5H-pyrrolo[1,2-a]azepine-9-carboxylate,
isopropyl 3-(5-methyl-2-furoyl)-2-propyl-6,7,8,9-tetrahydro-5H-pyrrolo[1,2-a]azepine-9-carboxylate and
isopropyl 3-(3-chloro-2-furoyl)-2-butyl-6,7,8,9-tetrahydro-5H-pyrrolo[1,2-a]azepine-9-carboxylate.

EXAMPLE 38

A solution of 900 mg. of isopropyl 3-(2-thenoyl)-2-methyl-5,6,7,8-tetrahydropyrrolo[1,2-a]pyridine-8-carboxylate in 15 ml. of methanol is treated with a solution of 125 g. of potassium carbonate in 10 ml. of water. The reaction mixture is refluxed under nitrogen atmosphere for 3 hours, cooled, and evaporated to dryness. The residue is taken up in 50 ml. of water, cooled to 0° and made acidic with 10% aqueous hydrochloric acid. The resultant mixture is extracted with ethyl acetate (3×50 ml.). The extracts are dried over magnesium sulfate and evaporated to dryness under reduced pressure, to give 3-(2-thenoyl)-2-methyl-5,6,7,8-tetrahydropyrrolo[1,2-a]pyridine-8-carboxylic acid (XIIa, R=CH$_3$, M=H, X=S, n=1).

In like manner substituting isopropyl 3-(2-thenoyl)-2-methyl-6,7,8,9-tetrahydro-5H-pyrrolo[1,2-a]azepine-9-carboxylate for isopropyl 3-(2-thenoyl)-2-methyl-5,6,7,8-tetrahydropyrrolo[1,2-a]pyridine-8-carboxylate there is obtained 3-(2-thenoyl)-2-methyl-6,7,8,9-tetrahydro-5H-pyrrolo[1,2-a]azepine-9-carboxylic acid (XIIa, R=CH, M=H,$_3$X=S, n=2).

In a similar manner, or alternatively by the hydrolysis method of Example 20, the remaining isopropyl ester compounds obtained in Example 24A are converted into the corresponding free acids, namely:
3-(2-furoyl)-2-methyl-5,6,7,8-tetrahydropyrrolo[1,2-a]pyridine-8-carboxylic acid,
3-(3-methyl-2-thenoyl)-2-methyl-5,6,7,8-tetrahydropyrrolo[1,2-a]pyridine-8-carboxylic acid,
3-(4-methyl-2-thenoyl)-2-methyl-5,6,7,8-tetrahydropyrrolo[1,2-a]pyridine-8-carboxylic acid,
3-(5-methyl-2-thenoyl)-2-methyl-5,6,7,8-tetrahydropyrrolo[1,2-a]pyridine-8-carboxylic acid,
3-(4-chloro-2-thenoyl)-2-methyl-5,6,7,8-tetrahydropyrrolo[1,2-a]pyridine-8-carboxylic acid,
3-(5-chloro-2-thenoyl)-2-methyl-5,6,7,8-tetrahydropyrrolo[1,2-a]pyridine-8-carboxylic acid,
3-(3-bromo-2-thenoyl)-2-methyl-5,6,7,8-tetrahydropyrrolo[1,2-a]pyridine-8-carboxylic acid,
3-(4-bromo-2-thenoyl)-2-methyl-5,6,7,8-tetrahydropyrrolo[1,2-a]pyridine-8-carboxylic acid,
3-(5-bromo-2-thenoyl)-2-methyl-5,6,7,8-tetrahydropyrrolo[1,2-a]pyridine-8-carboxylic acid,
3-(3-methyl-2-furoyl)-2-methyl-5,6,7,8-tetrahydropyrrolo[1,2-a]pyridine-8carboxylic acid,
3-(4-methyl-2-furoyl)-2-methyl-5,6,7,8-tetrahydropyrrolo[1,2-a]pyridine-8-carboxylic acid,
3-(5-methyl-2-furoyl)-2-methyl-5,6,7,8-tetrahydropyrrolo[1,2-a]pyridine-8-carboxylic acid,
3-(3-chloro-2-furoyl)-2-methyl-5,6,7,8-tetrahydropyrrolo[1,2-a]pyridine-8-carboxylic acid,
3-(4-chloro-2-furoyl)-2-methyl-5,6,7,8-tetrahydropyrrolo[1,2-a]pyridine-8-carboxylic acid,
3-(5-chloro-2-furoyl)-2-methyl-5,6,7,8-tetrahydropyrrolo[1,2-a]pyridine-8-carboxylic acid,
3-(4-bromo-2-furoyl)-2-methyl-5,6,7,8-tetrahydropyrrolo[1,2-a]pyridine-8-carboxylic acid,
3-(5-bromo-2-furoyl)-2-methyl-5,6,7,8-tetrahydropyrrolo[1,2-a]pyridine-8-carboxylic acid,
3-(2-furoyl)-2-methyl-6,7,8,9-tetrahydro-5H-pyrrolo[1,2-a]azepine-9-carboxylic acid,
3-(3-methyl-2-thenoyl)-2-methyl-6,7,8,9-tetrahydro-5H-pyrrolo[1,2-a]azepine-9-carboxylic acid,
3-(4-methyl-2-thenoyl)-2-methyl-6,7,8,9-tetrahydro-5H-pyrrolo[1,2-a]azepine-9-carboxylic acid,
3-(5-methyl-2-thenoyl)-2-methyl-6,7,8,9-tetrahydro-5H-pyrrolo[1,2-a]azepine-9-carboxylic acid,
3-(4-chloro-2-thenoyl)-2-methyl-6,7,8,9-tetrahydro-5H-pyrrolo[1,2-a]azepine-9-carboxylic acid,
3-(5-chloro-2-thenoyl)-2-methyl-6,7,8,9-tetrahydro-5H-pyrrolo[1,2-a]azepine-9-carboxylic acid,
3-(3-bromo-2-thenoyl)-2-methyl-6,7,8,9-tetrahydro-5H-pyrrolo[1,2-a]azepine-9-carboxylic acid,
3-(4-bromo-2-thenoyl)-2-methyl-6,7,8,9-tetrahydro-5H-pyrrolo[1,2-a]azepine-9-carboxylic acid,
3-(5-bromo-2-thenoyl)-2-methyl-6,7,8,9-tetrahydro-5H-pyrrolo[1,2-a]azepine-9-carboxylic acid,
3-(3-methyl-2-furoyl)-2-methyl-6,7,8,9-tetrahydro-5H-pyrrolo[1,2-a]azepine-9-carboxylic acid,
3-(4-methyl-2-furoyl)-2-methyl-6,7,8,9-tetrahydro-5H-pyrrolo[1,2-a]azepine-9-carboxylic acid,
3-(5-methyl-2-furoyl)-2-methyl-6,7,8,9-tetrahydro-5H-pyrrolo[1,2-a]azepine-9-carboxylic acid,
3-(3-chloro-2-furoyl)-2-methyl-6,7,8,9-tetrahydro-5H-pyrrolo[1,2-a]azepine-9-carboxylic acid,
3-(4-chloro-2-furoyl)-2-methyl-6,7,8,9-tetrahydro-5H-pyrrolo[1,2-a]azepine-9-carboxylic acid, 3-(5-chloro-2-furoyl)-2-methyl-6,7,8,9-tetrahydro-5H-pyrrolo[1,2-a]azepine-9-carboxylic acid,
3-(4-bromo-2-furoyl)-2-methyl-6,7,8,9-tetrahydro-5H-pyrrolo[1,2-a]azepine-9-carboxylic acid,
3-(5-bromo-2-furoyl)-2-methyl-6,7,8,9-tetrahydro-5H-pyrrolo[1,2-a]azepine-9-carboxylic acid,
3-(2-thenoyl)-2-ethyl-6,7,8,9-tetrahydro-5H-pyrrolo[1,2-a]azepine-9-carboxylic acid,
3-(2-furoyl)-2-propyl-6,7,8,9-tetrahydro-5H-pyrrolo[1,2-a]azepine-9-carboxylic acid,
3-(3-methyl-2-thenoyl)-2-butyl-6,7,8,9-tetrahydro-5H-pyrrolo[1,2-a]azepine-9-carboxylic acid,
3-(4-chloro-2-thenoyl)-2-ethyl-6,7,8,9-tetrahydro-5H-pyrrolo[1,2-a]azepine-9-carboxylic acid,
3-(5-methyl-2-furoyl)-2-propyl-6,7,8,9-tetrahydro-5H-pyrrolo[1,2-a]azepine-9-carboxylic acid and
3-(3-chloro-2-furoyl)-2-butyl-6,7,8,9-tetrahydro-5H-pyrrolo[1,2-a]azepine-9-carboxylic acid,
3-(2-thenoyl)-2-ethyl-5,6,7,8-tetrahydropyrrolo[1,2-a]pyridine-8-carboxylic acid,
3-(2-furoyl)-2-propyl-5,6,7,8-tetrahydropyrrolo[1,2-a]pyridine-8-carboxylic acid,
3-(3-methyl-2-thenoyl)-2-butyl-5,6,7,8-tetrahydropyrrolo[1,2-a]pyridine-8-carboxylic acid,
3-(4-chloro-2-thenoyl)-2-ethyl-5,6,7,8-tetrahydropyrrolo[1,2-a]pyridine-8-carboxylic acid,
3-(5-methyl-2-furoyl)-2-propyl-5,6,7,8-tetrahydropyrrolo[1,2-a]pyridine-8-carboxylic acid and
3-(3-chloro-2-furoyl)-2-butyl-5,6,7,8-tetrahydropyrrolo[1,2-a]pyridine-8-carboxylic acid; and

EXAMPLE 39

A solution of 1.55 mg. of N,N-dimethylthiophene-3-carboxamide and 0.95 ml. of phosphororus oxychloride in 30 ml. of 1,2-dichloroethane is refluxed for 30 minutes. To this solution is added a solution of 0.895 g. of isopropyl 5,6,7,8-tetrahydropyrrolo[1,2-a]pyridine-8-carboxylate in 20 ml. of 1,2-dichloroethane. The reaction mixture is refluxed under an argon atmosphere for 8 hours, treated with a solution of 4.1 g. of sodium acetate in 20 ml. of water and refluxed for a further 2 hours. The resultant mixture is then evaporated to dryness and the residue is chromatographed on silica gel, eluting with hexane:ethyl acetate, thus obtaining isopropyl 3-(3-thenoyl)-5,6,7,8-tetrahydropyrrolo[1,2-a]pyridine-8-carboxylate (XII, R=H, $R^2$=iC$_3$H$_7$, X=S, n=1).

In like manner, substituting isopropyl 6,7,8,9-tetrahydro-5H-pyrrolo[1,2-a]azepine-9-carboxylate for isopropyl 5,6,7,8-tetrahydropyrrolo[1,2-a]pyridine-8-carboxylate there is obtained isopropyl 3(3-thenoyl)-6,7,8,9-tetrahydro-5H-pyrrolo[1,2-a]azepine-9-carboxylate (XIII, R=H, $R^2$=iC$_3$H$_7$, X=S, n=2).

In a similar manner
isopropyl 2-methyl-5,6,7,8-tetrahydropyrrolo[1,2-a]pyridine-8-carboxylate,
isopropyl 2-propyl-tetrahydropyrrolo[1,2-a]pyrimidine-8-carboxylate; and
isopropyl 2-methyl-6,7,8,9-tetrahydro-5H-pyrrolo[1,2-a]azepine-9-carboxylate, and
isopropyl 2-propyl-6,7,8,9-tetrahydro-5H-pyrrolo[1,2-a]azepine-9-carboxylate,
are converted respectively into
isopropyl 3-(3-thenoyl)-2-methyl-5,6,7,8-tetrahydropyrrolo[1,2-a]pyridine-8-carboxylate and
isopropyl 3-(3-thenoyl)-2-propyl-5,6,7,8-tetrahydropyrrolo[1,2-a]pyridine-8-carboxylate; and isopropyl 2-methyl-6,7,8,9-tetrahydro-5H-pyrrolo[1,2-a]azepine-9-carboxylate and
isopropyl 2-propyl-6,7,8,9-tetrahydro-5H-pyrrolo[1,2-a]azepine-9-carboxylate.

By the same method, substituting N,N-dimethylfuran-3-carboxamide for N,N-dimethylthiophene-3-carboxamide there are obtained the corresponding 3-(3-furoyl) derivatives, namely:
isopropyl 3-(3-furoyl)-5,6,7,8-tetrahydropyrrolo[1,2-a]pyridine-8-carboxylate,
isopropyl 3-(3-furoyl)2-methyl-5,6,7,8-tetrahydropyrrolo[1,2-a]pyridine-8-carboxylate and
isopropyl 3-(3-furoyl)2-propyl-5,6,7,8-tetrahydropyrrolo[1,2-a]pyridine-8-carboxylate; and
isopropyl 3-(3-furoyl)-6,7,8,9-tetrahydro-5H-pyrrolo[1,2-a]azepine-9-carboxylate,
isopropyl 3-(3-furoyl)2-methyl-6,7,8,9-tetrahydro-5H-pyrrolo[1,2-a]azepine-9-carboxylate and
isopropyl 3-(3-furoyl)2-propyl-6,7,8,9-tetrahydro-5H-pyrrolo[1,2-a]azepine-9-carboxylate.

EXAMPLE 40

A solution of 321 mg. of isopropyl 3-(3-thenoyl)-5,6,7,8-tetrahydropyrrolo[1,2-a]pyridine-8-carboxylate in 50 ml. of 50% aqueous methanol containing 0.135 g. of 35% potassium hydroxide is refluxed under an atmosphere of nitrogen for 2 hours. The methanol is then removed under reduced pressure and the basic solution which remains is diluted with water and extracted with chloroform to remove any unsaponifiable product. The aqueous alkaline phase is acidified with 20% hydrochloric acid and extracted three times with ethyl acetate. The combined extracts are dried over sodium sulfate and evaporated to dryness under reduced pressure, thus obtaining 3-(3-thenoyl)-5,6,7,8-tetrahydropyrrolo[1,2-a]pyridine-8-carboxylic acid, (XIIIa, R=H, X=S, n=1).

In like manner, substituting isopropyl 3-(3-thenoyl)-6,7,8,9-tetrahydro-5H-pyrrolo[1,2-a]azepine-9-carboxylate for isopropyl 3-(3-thenoyl)-5,6,7,8-tetrahydropyrrolo[1,2-a]pyridine-8-carboxylate there is obtained isopropyl 3-(3-thenoyl)-6,7,8,9-tetrahydro-5H-pyrrolo[1,2-a]azepine-9-carboxylic acid (XIIIa, R=H, X=S, n=2).

By the same method, the remaining compounds obtained in Example 39 are converted into the free acids, namely:
3-(3-thenoyl)-2-methyl-5,6,7,8-tetrahydropyrrolo[1,2-a]pyridine-8-carboxylic acid,
3-(3-thenoyl)-2-propyl-5,6,7,8-tetrahydropyrrolo[1,2-a]pyridine-8-carboxylic acid,
3-(3-furoyl)-5,6,7,8-tetrahydropyrrolo[1,2-a]pyridine-8-carboxylic acid,
3-(3-furoyl)-6-methyl-5,6,7,8-tetrahydropyrrolo[1,2-a]pyridine-8-carboxylic acid, and
3-(3-thenoyl)-2-methyl-6,7,8,9-tetrahydro-5H-pyrrolo[1,2-a]azepine-9-carboxylic acid,
3-(3-thenoyl)-2-propyl-6,7,8,9-tetrahydro-5H-pyrrolo[1,2-a]azepine-9-carboxylic acid,
3-(3-furoyl)-6,7,8,9-tetrahydro-5H-pyrrolo[1,2-a]azepine-9-carboxylic acid and
3-(3-furoyl)-6-methyl-6,7,8,9-tetrahydro-5H-pyrrolo[1,2-a]azepine-9-carboxylic acid.

EXAMPLE 41

A solution of 1.40 g. of N,N-dimethyl-1-methylpyrrole-2-carboxamide in 30 ml. of anhydrous dichloromethane containing 1.53 g. of phosphorous oxychloride is refluxed for 30 minutes under an argon atmosphere.

To this solution is added a solution of 895 mg. of isopropyl 5,6,7,8-tetrahydropyrrolo[1,2-a]pyridine-8-carboxylate in 20 ml. of 1,2-dichloroethane. The reaction mixture is refluxed under an argon atmosphere for 50 hours, cooled to room temperature and treated with a solution of 4.1 g. of sodium acetate dissolved in 15 ml. of water. The resultant mixture is refluxed for 30 minutes further, and then cooled, the organic phase is separated and the aqueous phase extracted with chloroform. The combined organic solutions are washed with saturated sodium chloride solution (2×10 ml.), dried with anhydrous sodium sulfate and evaporated to dryness under reduced pressure. The oily residue is purified by t.l.c. using ethyl acetate:methylene chloride as eluant, to yield isopropyl 3-(N-methyl-2-pyrroyl)-5,6,7,8-tetrahydropyrrolo[1,2-a]pyridine-8-carboxylate (XIV, R=H, Q=CH$_3$, R$^2$=iC$_3$H$_7$, n=1).

In like manner, substituting isopropyl 6,7,8,9-tetrahydro-5H-pyrrolo[1,2-a]azepine-9-carboxylate for isopropyl 5,6,7,8-tetrahydropyrrolo[1,2-a]pyridine-8-carboxylate there is obtained isopropyl 3-(N-methyl-2-pyrroyl)-6,7,8,9-tetrahydro-5H-pyrrolo[1,2-a]azepine-9-carboxylate (XIV, R=H, Q=CH$_3$, R$^2$=iC$_3$H$_7$, n=2).

EXAMPLE 42

A mixture of 0.314 g. of isopropyl 3-(N-methyl-2-pyrroyl)-5,6,7,8-tetrahydropyrrolo[1,2-a]pyridine-8-carboxylate, 0.28 g. of potassium carbonate and 10 ml. of a (1:1) methanol-water mixture is refluxed under nitrogen atmosphere for 3 hours, cooled, and evaporated to dryness. The residue is taken up in 50 ml. of water and extracted with ethyl acetate (3×10 ml.). The aqueous solution is acidified with 10% hydrochloric acid and extracted with ethyl acetate (10×15 ml.). The combined extracts are washed with saturated sodium chloride solution dried with anhydrous sodium sulfate and evaporated to dryness under reduced pressure, to afford 3-(N-methyl-2-pyrroyl)-5,6,7,8-tetrahydropyrrolo[1,2-a]pyridine-8-carboxylic acid, (XIVa, R=H, Q=CH$_3$, n=2).

In like manner substituting isopropyl 3-(N-methyl-2-pyrroyl)-6,7,8,9-tetrahydro-5H-pyrrolo[1,2,-a]azepine-9-carboxylate for isopropyl 3-(N-methyl-2-pyrroyl)-5,6,7,8-tetrahydropyrrolo[1,2-a]pyridine-8-carboxylate there is obtained 3-(N-methyl-2-pyrroyl)-6,7,8,9-tetrahydro-5H-pyrrolo[1,2-a]azepine-9-carboxylic acid (XIVa, R=H, Q=CH$_3$, n=2).

EXAMPLE 43

By following the methods of Example 6, the remaining compounds obtained in Example 5 are converted respectively into:
methyl 5,6,7,8-tetrahydropyrrolo[1,2-a]pyridine-8-carboxylate,
ethyl 5,6,7,8-tetrahydropyrrolo[1,2-a]pyridine-8-carboxylate,
propyl 5,6,7,8-tetrahydropyrrolo[1,2-a]pyridine-8-carboxylate, and
butyl 5,6,7,8-tetrahydropyrrolo[1,2-a]pyridine-8-carboxylate; and
methyl 6,7,8,9-tetrahydro-5H-pyrrolo[1,2-a]azepine-9-carboxylate,
ethyl 6,7,8,9-tetrahydro-5H-pyrrolo[1,2-a]azepine-9-carboxylate,
propyl 6,7,8,9-tetrahydro-5H-pyrrolo[1,2-a]azepine-9-carboxylate, and
butyl 6,7,8,9-tetrahydro-5H-pyrrolo[1,2-a]azepine-9-carboxylate.

Upon condensation of these compounds with N,N-dimethyl-1-methylpyrrole-2-carboxamide, in accordance with the method of Example 42, there are respectively obtained:
methyl 3-(N-methyl-2-pyrroyl)-5,6,7,8-tetrahydropyrrolo[1,2-a]pyridine-8-carboxylate,
ethyl 3-(N-methyl-2-pyrroyl)-5,6,7,8-tetrahydropyrrolo[1,2-a]pyridine-8-carboxylate,
propyl 3-(N-methyl-2-pyrroyl)-5,6,7,8-tetrahydropyrrolo[1,2-a]pyridine-8-carboxylate,
butyl 3-(N-methyl-2-pyrroyl)-5,6,7,8-tetrahydropyrrolo[1,2-a]pyridine-8-carboxylate; and
methyl 3-(N-methyl-2-pyrroyl)-6,7,8,9-tetrahydro-5H-pyrrolo[1,2-a]azepine-9-carboxylate,
ethyl 3-(N-methyl-2-pyrroyl)-6,7,8,9-tetrahydro-5H-pyrrolo[1,2-a]azepine-9-carboxylate,
propyl 3-(N-methyl-2-pyrroyl)-6,7,8,9-tetrahydro-5H-pyrrolo[1,2-a]azepine-9-carboxylate,
butyl 3-(N-methyl-2-pyrroyl)-6,7,8,9-tetrahydro-5H-pyrrolo[1,2-a]azepine-9-carboxylate; and

EXAMPLE 44

Example 41 is repeated using 1.5 molar equivalents of:
N,N-dimethylpyrrole-2-carboxamide,
N,N-dimethyl-1-ethylpyrrole-2-carboxamide,
N,N-dimethyl-1-propylpyrrole-2-carboxamide and
N,N-dimethyl-1-butylpyrrole-2-carboxamide
in place of N,N-dimethyl-1-methylpyrrole-2-carboxamide, thus obtaining respectively:
isopropyl 3-(2-pyrroyl)-5,6,7,8-tetrahydropyrrolo[1,2-a]pyridine-8-carboxylate,
isopropyl 3-(N-ethyl-2-pyrroyl)-5,6,7,8-tetrahydropyrrolo[1,2-a]pyridine-8-carboxylate,
isopropyl 3-(N-propyl-2-pyrroyl)-5,6,7,8-tetrahydropyrrolo[1,2-a]pyridine-8-carboxylate and
isopropyl 3-(N-butyl-2-pyrroyl)-5,6,7,8-tetrahydropyrrolo[1,2-a]pyridine-8-carboxylate; and
isopropyl 3-(2-pyrroyl)-6,7,8,9-tetrahydro-5H-pyrrolo[1,2-a]azepine-9-carboxylate,
isopropyl 3-(N-ethyl-2-pyrroyl)-6,7,8,9-tetrahydro-5H-pyrrolo[1,2-a]azepine-9-carboxylate,
isopropyl 3-(N-propyl-2-pyrroyl)-6,7,8,9-tetrahydro-5H-pyrrolo[1,2-a]azepine-9-carboxylate and
isopropyl 3-(N-butyl-2-pyrroyl)-6,7,8,9-tetrahydro-5H-pyrrolo[1,2-a]azepine-9-carboxylate.

Upon hydrolysis of the isopropyl ester group, in accordance with the method of Example 42, there are obtained the corresponding free acids, namely:
3-(2-pyrroyl)-5,6,7,8-tetrahydropyrrolo[1,2-a]pyrimidine-8-carboxylic acid,
3-(N-ethyl-2-pyrroyl)-5,6,7,8-tetrahydropyrrolo[1,2-a]pyridine-8-carboxylic acid,
3-(N-propyl-2-pyrroyl)-5,6,7,8-tetrahydropyrrolo[1,2-a]pyridine-8-carboxylic acid,
3-(N-butyl-2-pyrroyl)-5,6,7,8-tetrahydropyrrolo[1,2-a]pyridine-8-carboxylic acid; and
3-(2-pyrroyl)-6,7,8,9-tetrahydro-5H-pyrrolo[1,2-a]azepine-9-carboxylic acid,
3-(N-ethyl-2-pyrroyl)-6,7,8,9-tetrahydro-5H-pyrrolo[1,2-a]azepine-9-carboxylic acid,
3-(N-propyl-2-pyrroyl)-6,7,8,9-tetrahydro-5H-pyrrolo[1,2-a]azepine-9-carboxylic acid,
3-(N-butyl-2-pyrroyl)-6,7,8,9-tetrahydro-5H-pyrrolo[1,2-a]azepine-9-carboxylic acid.

EXAMPLE 45

In accordance with the method of Example 37, isopropyl 2-methyl-5,6,7,8-tetrahydropyrrolo[1,2-a]pyridine-8-carboxylate is condensed with N,N-dimethyl-1-methylpyrrole-2-carboxamide, to produce isopropyl 3-(N-methyl-2-pyrroyl)-2-methyl-5,6,7,8-tetrahydropyrrolo[1,2-a]pyridine-8-carboxylate (XIV, R and Q=CH$_3$, R$^2$=iC$_3$H$_7$, n=1).

In like manner, substituting isopropyl 2-methyl-6,7,8,9-tetrahydro-5H-pyrrolo[1,2-a]azepine-9-carboxylate for isopropyl 2-methyl-5,6,7,8-tetrahydropyrrolo[1,2-a]pyridine-8-carboxylate there is obtained isopropyl 3-(N-methyl-2-pyrroyl)-2-methyl-6,7,8,9-tetrahydro-5H-pyrrolo[1,2-a]azepine-9-carboxylate (XIV, R and Q=CH$_3$, R$^2$=iC$_3$H$_7$, n=2).

In a similar manner but using the N,N-dimethylpyrrole-2-carboxamides listed in Example 29 in place of N,N-dimethyl-1-methylpyrrole-2-carboxamide, there are respectively obtained:

isopropyl 3-(2-pyrroyl)-2-methyl-5,6,7,8-tetrahydropyrrolo[1,2-a]pyridine-8-carboxylate,
isopropyl 3-(N-ethyl-2-pyrroyl)-2-methyl-5,6,7,8-tetrahydropyrrolo[1,2-a]pyridine-8-carboxylate,
isopropyl 3-(N-propyl-2-pyrroyl)-2-methyl-5,6,7,8-tetrahydropyrrolo[1,2-a]pyridine-8-carboxylate and
isopropyl 3-(N-butyl-2-pyrroyl)-2-methyl-5,6,7,8-tetrahydropyrrolo[1,2-a]pyridine-8-carboxylate; and
isopropyl 3-(2-pyrroyl)-2-methyl-6,7,8,9-tetrahydro-5H-pyrrolo[1,2-a]azepine-9-carboxylate,
isopropyl 3-(N-ethyl-2-pyrroyl)-2-methyl-6,7,8,9-tetrahydro-5H-pyrrolo[1,2-a]azepine-9-carboxylate,
isopropyl 3-(N-propyl -2-pyrroyl)-2-methyl-6,7,8,9-tetrahydro-5H-pyrrolo[1,2-a]azepine-9-carboxylate and
isopropyl 3-(N-butyl-2-pyrroyl)-2-methyl-6,7,8,9-tetrahydro-5H-pyrrolo[1,2-a]azepine-9-carboxylate.

EXAMPLE 46

By following the method of Example 41, the compounds obtained in Example 14 are condensed with the N,N-dimethyl-2-pyrrolamide reagents of Examples 41 and 44, to produce the corresponding 3-(2-pyrroyl) derivatives.

Representative compounds thus obtained are:
isopropyl 3-(N-ethyl-2-pyrroyl)-2-ethyl-5,6,7,8-tetrahydropyrrolo[1,2-a]pyridine-8-carboxylate,
isopropyl 3-(2-pyrroyl)-2-propyl-5,6,7,8-tetrahydropyrrolo[1,2-a]pyridine-8-carboxylate,
isopropyl 3-(N-methyl-2-pyrroyl)-2-butyl-5,6,7,8-tetrahydropyrrolo[1,2-a]pyridine-8-carboxylate,
isopropyl 3-(N-propyl-2-pyrroyl)-2-ethyl-5,6,7,8-tetrahydropyrrolo[1,2-a]pyridine-8-carboxylate,
isopropyl 3-(N-butyl-2-pyrroyl)-2-propyl-5,6,7,8-tetrahydropyrrolo[1,2-a]pyridine-8-carboxylate,
isopropyl 3-(N-methyl-2-pyrroyl)-2-butyl-5,6,7,8-tetrahydropyrrolo[1,2-a]pyridine-8-carboxylate and
isopropyl 3-(2-pyrroyl)-2-ethyl-5,6,7,8-tetrahydropyrrolo[1,2-a]pyridine-8-carboxylate; and
isopropyl 3-(N-methyl-2-pyrroyl)-2-ethyl-6,7,8,9-tetrahydro-5H-pyrrolo[1,2-a]azepine-9-carboxylate,
isopropyl 3-(2-pyrroyl)-2-propyl-6,7,8,9-tetrahydro-5H-pyrrolo[1,2-a]azepine-9-carboxylate,
isopropyl 3-(N-ethyl-2-pyrroyl)-2-butyl-6,7,8,9-tetrahydro-5H-pyrrolo[1,2-a]azepine-9-carboxylate,
isopropyl 3-(N-propyl-2-pyrroyl)-2-ethyl-6,7,8,9-tetrahydro-5H-pyrrolo[1,2-a]azepine-9-carboxylate,
isopropyl 3-(N-butyl-2-pyrroyl)-2-propyl-6,7,8,9-tetrahydro-5H-pyrrolo[1,2-a]azepine-9-carboxylate,
isopropyl 3-(N-methyl-2-pyrroyl)-2-butyl-6,7,8,9-tetrahydro-5H-pyrrolo[1,2-a]azepine-9-carboxylate and
isopropyl 3-(2-pyrroyl)-2-ethyl-6,7,8,9-tetrahydro-5H-pyrrolo[1,2-a]azepine-9-carboxylate.

EXAMPLE 47

A solution of 328 mg. of isopropyl 5-(N-methyl-2-pyrroyl)-2-methyl-5,6,7,8-tetrahydropyrrolo[1,2-a]pyridine-8-carboxylate in 5 ml. of methanol is treated with a solution of 0.28 g. of potassium carbonate in 5 ml. of water. The reaction mixture is refluxed under nitrogen atmosphere for 3 hours, cooled, and evaporated to dryness. The residue is taken up in 50 ml. of water, cooled to 0°, made acidic with 10% hydrochloric acid and the resultant mixture extracted with ethyl acetate (3×50 ml.). The combined extracts are dried over magnesium sulfate and evaporated to dryness under reduced pressure, to give 5-(N-methyl-2-pyrroyl)-2-methyl-5,6,7,8-tetrahydropyrrolo[1,2-a]pyridine-8-carboxylic acid (XIVa, R and Q=CH$_3$, n−1).

In like manner, substituting isopropyl 5-(N-methyl-2-pyrroyl)-2-methyl-6,7,8,9-tetrahydro-5H-pyrrolo[1,2-a]azepine-9-carboxylate for isopropyl 5-(N-methyl-2-pyrroyl)-2-methyl-5,6,7,8-tetrahydropyrrolo[1,2-a]pyridine-8-carboxylate is productive of 5-(N-methyl-2-pyrroyl)-2-methyl-6,7,8,9-tetrahydro-5H-pyrrolo[1,2-a]azepine-9-carboxylate (XIVa, R=CH$_3$, Q=CH$_3$, n=2).

In a similar manner the remaining isopropyl ester compounds obtained in Example 45 and 46 are converted into the corresponding free acids, namely:
3-(2-pyrroyl)-2-methyl-5,6,7,8-tetrahydropyrrolo[1,2-a]pyridine-8-carboxylic acid,
3-(N-ethyl-2-pyrroyl)-2-methyl-5,6,7,8-tetrahydropyrrolo[1,2-a]pyridine-8-carboxylic acid,
3-(N-propyl-2-pyrroyl)-2-methyl-5,6,7,8-tetrahydropyrrolo[1,2-a]pyridine-8-carboxylic acid,
3-(N-butyl-2-pyrroyl)-2-methyl-5,6,7,8-tetrahydropyrrolo[1,2-a]pyridine-8-carboxylic acid,
3-(N-methyl-2-pyrroyl)-2-ethyl-5,6,7,8-tetrahydropyrrolo[1,2-a]pyridine-8-carboxylic acid,
3-(N-ethyl-2-pyrroyl)-2-ethyl-5,6,7,8-tetrahydropyrrolo[1,2-a]pyridine-8-carboxylic acid,
3-(2-pyrroyl)-2-propyl-5,6,7,8-tetrahydropyrrolo[1,2-a]pyridine-8-carboxylic acid,
3-(N-ethyl-2-pyrroyl)-2-butyl-5,6,7,8-tetrahydropyrrolo[1,2-a]pyridine-8-carboxylic acid,
3-(N-propyl-2-pyrroyl)-2-ethyl-5,6,7,8-tetrahydropyrrolo[1,2-a]pyridine-8-carboxylic acid,
3-(N-butyl-2-pyrroyl)-2-propyl-5,6,7,8-tetrahydropyrrolo[1,2-a]pyridine-8-carboxylic acid,
3-(N-methyl-2-pyrroyl)-2-butyl-5,6,7,8-tetrahydropyrrolo[1,2-a]pyridine-8-carboxylic acid and
3-(2-pyrroyl)-2-ethyl-5,6,7,8-tetrahydropyrrolo[1,2-a]pyridine-8-carboxylic acid; and
3-(2-pyrroyl)-2-methyl-6,7,8,9-tetrahydro-5H-pyrrolo[1,2-a]azepine-9-carboxylate,
3-(N-ethyl-2-pyrroyl)-2-methyl-6,7,8,9-tetrahydro-5H-pyrrolo[1,2-a]azepine-9-carboxylate,
3-(N-propyl-2-pyrroyl)-2-methyl-6,7,8,9-tetrahydro-5H-pyrrolo[1,2-a]azepine-9-carboxylate,
3-(N-butyl-2-pyrroyl)-2-methyl-6,7,8,9-tetrahydro-5H-pyrrolo[1,2-a]azepine-9-carboxylate,
3-(N-methyl-2-pyrroyl)-2-ethyl-6,7,8,9-tetrahydro-5H-pyrrolo[1,2-a]azepine-9-carboxylate,
3-(N-ethyl-2-pyrroyl)-2-ethyl-6,7,8,9-tetrahydro-5H-pyrrolo[1,2-a]azepine-9-carboxylate, 3-(2-pyrroyl)-2-propyl-6,7,8,9-tetrahydro-5H-pyrrolo[1,2-a]azepine-9-carboxylate,
3-(N-ethyl-2-pyrroyl)-2-butyl-6,7,8,9-tetrahydro-5H-pyrrolo[1,2-a]azepine-9-carboxylate,
3-(N-propyl-2-pyrroyl)-2-ethyl-6,7,8,9-tetrahydro-5H-pyrrolo[1,2-a]azepine-9-carboxylate,
3-(N-butyl-2-pyrroyl)-2-propyl-6,7,8,9-tetrahydro-5H-pyrrolo[1,2-a]azepine-9-carboxylate,
3-(N-methyl-2-pyrroyl)-2-butyl-6,7,8,9-tetrahydro-5H-pyrrolo[1,2-a]azepine-9-carboxylate and
3-(2-pyrroyl)-2-ethyl-6,7,8,9-tetrahydro-5H-pyrrolo[1,2-a]azepine-9-carboxylate.

EXAMPLE 48

A solution of 269 mg. of 3-benzoyl-5,6,7,8-tetrahydropyrrolo[1,2-a]pyridine-8-carboxylic acid in 10 ml. of dichloromethane is treated with an excess of ethereal diazomethane, and the reaction mixture is maintained at room temperature for 30 minutes. The solvents and excess reagent are eliminated under reduced pressure and the residue crystallized from ethyl acetate-methanol, to yield methyl 3-benzoyl-5,6,7,8-tetrahydropyrrolo[1,2-a]pyridine-8-carboxylate.

Likewise but using diazoethane and diazopropane in place of diazomethane there are respectively obtained ethyl 3-benzoyl-5,6,7,8-tetrahydropyrrolo[1,2-a]pyridine-8-carboxylate and propyl 3-benzoyl-5,6,7,8-tetrahydropyrrolo[1,2-a]pyridine-8-carboxylate.

In a similar manner, the free acids obtained in Examples 8, 9, 11, 24B-29, 31, 34, 36, 38, 40, 42, 44 and 47 are converted into the corresponding methyl, ethyl and propyl esters.

EXAMPLE 49

A solution of 283 mg. of 3-p-toluoyl-5,6,7,8-tetrahydropyrrolo[1,2-a]pyridine-8-carboxylic acid in 20 ml. of isoamyl alcohol is saturated with hydrogen chloride. After 24 hours, the excess alcohol is distilled off in vacuo and the residue purified by chromatography on alumina, to yield isoamyl 3-p-toluoyl-5,6,7,8-tetrahydropyrrolo[1,2-a]pyridine-8-carboxylate.

Likewise other esters, e.g., pentyl, hexyl, octyl, nonyl, dodecyl, and the like, of 3-p-toluoyl-5,6,7,8-tetrahydropyrrolo[1,2-a]pyridine-8-carboxylic acid are obtained by substituting other alcohols, e.g., pentyl, hexyl, octyl, nonyl, dodecyl alcohol, and the like, for isoamyl alcohol.

By the same method the free acid compounds obtained in Examples 9, 10, 12, 24B-29, 34, 36, 38, 40, 42, 44 and 47 are esterfied with the appropriate alcohol thus obtaining the corresponding esters. Representative esters include:
isoamyl 3-benzoyl-5,6,7,8-tetrahydropyrrolo[1,2-a]pyridine-8-carboxylate,
pentyl 3-m-toluoyl-5,6,7,8-tetrahydropyrrolo[1,2-a]pyridine-8-carboxylate,
hexyl 3-p-ethylbenzoyl-5,6,7,8-tetrahydropyrrolo[1,2-a]pyridine-8-carboxylate,
isoamyl 3-o-propylbenzoyl-5,6,7,8-tetrahydropyrrolo[1,2-a]pyridine-8-carboxylate,
octyl 3-p-methoxybenzoyl-5,6,7,8-tetrahydropyrrolo[1,2-a]pyridine-8-carboxylate,
nonyl 3-p-isopropoxybenzoyl-5,6,7,8-tetrahydropyrrolo[1,2-a]pyridine-8-carboxylate,
dodecyl 3-o-chlorobenzoyl-5,6,7,8-tetrahydropyrrolo[1,2-a]pyridine-8-carboxylate,
isoamyl 3-m-chlorobenzoyl-5,6,7,8-tetrahydropyrrolo[1,2-a]pyridine-8-carboxylate,
dodecyl 3-o-fluorobenzoyl-5,6,7,8-tetrahydropyrrolo[1,2-a]pyridine-8-carboxylate,
hexyl 3-p-fluorobenzoyl-5,6,7,8-tetrahydropyrrolo[1,2-a]pyridine-8-carboxylate,
nonyl 3-p-bromobenzoyl-5,6,7,8-tetrahydropyrrolo[1,2-a]pyridine-8-carboxylate,
isoamyl 3-benzoyl-2-methyl-5,6,7,8-tetrahydropyrrolo[1,2-a]pyridine-8-carboxylate,
hexyl 3-p-ethylbenzoyl-2-methyl-5,6,7,8-tetrahydropyrrolo[1,2-a]pyridine-8-carboxylate,
nonyl 3-o-methoxybenzoyl-2-methyl-5,6,7,8-tetrahydropyrrolo[1,2-a]pyridine-8-carboxylate,
dodecyl 3-o-fluorobenzoyl-2-methyl-5,6,7,8-tetrahydropyrrolo[1,2-a]pyridine-8-carboxylate,
nonyl 3-benzoyl-2-ethyl-5,6,7,8-tetrahydropyrrolo[1,2-a]pyridine-8-carboxylate,
isoamyl 3-p-ethoxybenzoyl-2-ethyl-5,6,7,8-tetrahydropyrrolo[1,2-a]pyridine-8-carboxylate,
pentyl 3-p-fluorobenzoyl-2-propyl-5,6,7,8-tetrahydropyrrolo[1,2-a]pyridine-8-carboxylate,
hexyl 3-m-chlorobenzoyl-2-butyl-5,6,7,8-tetrahydropyrrolo[1,2-a]pyridine-8-carboxylate and
dodecyl 3-p-bromobenzoyl-2-butyl-5,6,7,8-tetrahydropyrrolo[1,2-a]pyridine-8-carboxylate; and
isoamyl 3-benzoyl-6,7,8,9-tetrahydro-5H-pyrrolo[1,2-a]azepine-9-carboxylate,
pentyl 3-m-toluoyl-6,7,8,9-tetrahydro-5H-pyrrole[1,2-a]azepine-9-carboxylate,
hexyl 3-p-ethylbenzoyl-6,7,8,9-tetrahydro-5H-pyrrole[1,2-a]azepine-9-carboxylate,
isoamyl 3-o-propylbenzoyl-6,7,8,9-tetrahydro-5H-pyrrole[1,2-a]azepine-9-carboxylate,
octyl 3-p-methoxybenzoyl-6,7,8,9-tetrahydro-5H-pyrrolo[1,2-a]azepine-9-carboxylate,
nonyl 3-p-isopropoxybenzoyl-6,7,8,9-tetrahydro-5H-pyrrole[1,2-a]azepine-9-carboxylate,
dodecyl 3-o-chlorobenzoyl-6,7,8,9-tetrahydro-5H-pyrrolo[1,2-a]azepine-9-carboxylate,
isoamyl 3-m-chlorobenzoyl-6,7,8,9-tetrahydro-5H-pyrrolo[1,2-a]azepine-9-carboxylate,
dodecyl 3-o-fluorobenzoyl-6,7,8,9-tetrahydro-5H-pyrrolo[1,2-a]azepine-9-carboxylate,
hexyl 3-p-fluorobenzoyl-6,7,8,9-tetrahydro-5H-pyrrolo[1,2-a]azepine-9-carboxylate,
nonyl 3-p-bromobenzoyl-6,7,8,9-tetrahydro-5H-pyrrolo[1,2-a]azepine-9-carboxylate,
isoamyl 3-benzoyl-2-methyl-6,7,8,9-tetrahydro-5H-pyrrolo[1,2-a]azepine-9-carboxylate,
hexyl 3-p-ethylbenzoyl-2-methyl-6,7,8,9-tetrahydro-5H-pyrrole[1,2-a]azepine-9-carboxylate,
nonyl 3-o-methoxybenzoyl-2-methyl-6,7,8,9-tetrahydro-5H-pyrrole[1,2-a]azepine-9-carboxylate,
dodecyl 3-o-fluorobenzoyl-2-methyl-6,7,8,9-tetrahydro-5H-pyrrole[1,2-a]azepine-9-carboxylate,
nonyl 3-benzoyl-2-ethyl-6,7,8,9-tetrahydro-5H-pyrrolo[1,2-a]azepine-9-carboxylate,
isoamyl 3-p-ethoxybenzoyl-2-ethyl-6,7,8,9-tetrahydro-5H-pyrrole[1,2-a]azepine-9-carboxylate,
pentyl 3-p-fluorobenzoyl-2-propyl-6,7,8,9-tetrahydro-5H-pyrrole[1,2-a]azepine-9-carboxylate,
hexyl 3-m-chlorobenzoyl-2-butyl-6,7,8,9-tetrahydro-5H-pyrrole[1,2-a]azepine-9-carboxylate,
dodecyl 3-p-bromobenzoyl-2-butyl-6,7,8,9-tetrahydro-5H-pyrrole[1,2-a]azepine-9-carboxylate, and the like.

EXAMPLE 50

To a solution of 283 mg. of 3-p-toluoyl-5,6,7,8-tetrahydropyrrolo[1,2-a]pyridine-8-carboxylic acid in 10 ml. of methanol is added 1 molar equivalent of sodium hydroxide, in the form of a 0.1 N solution. The solvent is then evaporated under reduced pressure and the residue taken up in 2 ml. of methanol, followed by precipitation with ether, to yield crude sodium 3-p-toluoyl-5,6,7,8-tetrahydropyrrolo[1,2-a]pyridine-8-carboxylate.

Likewise other salts, e.g., ammonium and potassium of 5-p-toluoyl-5,6,7,8-tetrahydropyrrolo[1,2-a]pyridine-8-carboxylic acid are prepared by substituting ammonium hydroxide and potassium hydroxide for sodium hydroxide.

In a similar manner, the carboxylic acid compounds obtained in Examples 8, 9, 11, 24B-29, 31, 34, 36, 38, 40, 42, 44 and 47 can be converted into the corresponding sodium, potassium and ammonium salts.

Representative compounds thus obtained are:
sodium 3-o-toluoyl-5,6,7,8-tetrahydropyrrolo[1,2-a]pyridine-8-carboxylate,
sodium 3-benzoyl-5,6,7,8-tetrahydropyrrolo[1,2-a]pyridine-8-carboxylate,
potassium 3-p-ethylbenzoyl-5,6,7,8-tetrahydropyrrolo[1,2-a]pyridine-8-carboxylate,
potassium 3-o-butylbenzoyl-5,6,7,8-tetrahydropyrrolo[1,2-a]pyridine-8-carboxylate,
sodium 3-p-methoxybenzoyl-5,6,7,8-tetrahydropyrrolo[1,2-a]pyridine-8-carboxylate,
ammonium 3-p-chlorobenzoyl-5,6,7,8-tetrahydropyrrolo[1,2-a]pyridine-8-carboxylate,
ammonium 3-o-fluorobenzoyl-5,6,7,8-tetrahydropyrrolo[1,2-a]pyridine-8-carboxylate,
potassium 3-p-bromobenzoyl-5,6,7,8-tetrahydropyrrolo[1,2-a]pyridine-8-carboxylate,
sodium 3-benzoyl-2-ethyl-5,6,7,8-tetrahydropyrrolo[1,2-a]pyridine-8-carboxylate,
potassium 3-toluoyl-2-methyl-5,6,7,8-tetrahydropyrrolo[1,2-a]pyridine-8-carboxylate,
ammonium 3-o-methoxybenzoyl-2-methyl-5,6,7,8-tetrahydropyrrolo[1,2-a]pyridine-8-carboxylate,
sodium 3-p-fluorobenzoyl-2-propyl-5,6,7,8-tetrahydropyrrolo[1,2-a]pyridine-8-carboxylate and
potassium 5-m-chlorobenzoyl-2-butyl-5,6,7,8-tetrahydropyrrolo[1,2-a]pyridine-8-carboxylate; and
sodium 3-o-toluoyl-6,7,8,9-tetrahydro-5H-pyrrolo[1,2-a]azepine-9-carboxylate,
sodium 3-benzoyl-6,7,8,9-tetrahydro-5H-pyrrolo[1,2-a]azepine-9-carboxylate,
potassium 3-p-ethylbenzoyl-6,7,8,9-tetrahydro-5H-pyrrolo[1,2-a]azepine-9-carboxylate,
potassium 3-o-butylbenzoyl-6,7,8,9-tetrahydro-5H-pyrrolo[1,2-a]azepine-9-carboxylate,
sodium 3-p-methoxybenzoyl-6,7,8,9-tetrahydro-5H-pyrrolo[1,2-a]azepine-9-carboxylate,
ammonium 3-p-chlorobenzoyl-6,7,8,9-tetrahydro-5H-pyrrolo[1,2-a]azepine-9-carboxylate,
ammonium 3-o-fluorobenzoyl-6,7,8,9-tetrahydro-5H-pyrrolo[1,2-a]azepine-9-carboxylate,
potassium 3-p-bromobenzoyl-6,7,8,9-tetrahydro-5H-pyrrolo[1,2-a]azepine-9-carboxylate,
sodium 3-benzoyl-2-ethyl-6,7,8,9-tetrahydro-5H-pyrrolo[1,2-a]azepine-9-carboxylate,
potassium 3-toluoyl-2-methyl-6,7,8,9-tetrahydro-5H-pyrrolo[1,2-a]azepine-9-carboxylate,
ammonium 3-o-methoxybenzoyl-2-methyl-6,7,8,9-tetrahydro-5H-pyrrolo[1,2-a]azepine-9-carboxylate,
sodium 3-p-fluorobenzoyl-2-propyl-6,7,8,9-tetrahydro-5H-pyrrolo[1,2-a]azepine-9-carboxylate and
potassium 5-m-chlorobenzoyl-2-butyl-6,7,8,9-tetrahydro-5H-pyrrolo[1,2-a]azepine-9-carboxylate.

EXAMPLE 51

To a solution of 283 mg. of 3-p-toluoyl-5,6,7,8-tetrahydropyrrolo[1,2-a]pyridine-8-carboxylic acid in 10 ml. of methanol is added 1 molar equivalent of potassium hydroxide, in the form of a 0.1 N solution, thus yielding a solution containing potassium 3-p-toluoyl-5,6,7,8-tetrahydropyrrolo[1,2-a]pyridine-8-carboxylate. A solution of 50 mg. of calcium carbonate dissolved in the minimum amount of 1 N hydrochloric acid necessary to effect solution of the calcium carbonate, is buffered with solid ammonium chloride, followed by the further addition of 5 ml. of water. The thus obtained buffered calcium solution is then added to the solution of potassium 3-p-toluoyl-5,6,7,8-tetrahydropyrrolo[1,2-a]pyridine-8-carboxylate and the precipitate which forms is collected by filtration, washed with water and air dried, to yield calcium 3-p-toluoyl-5,6,7,8-tetrahydropyrrolo[1,2-a]pyridine-8-carboxylate.

Likewise, magnesium 3-p-toluoyl-5,6,7,8-tetrahydropyrrolo[1,2-a]pyridine-8-carboxylate is prepared by substituting magnesium carbonate for calcium carbonate.

Similarly, by substituting 3-benzoyl-5,6,7,8-tetrahydropyrrolo[1,2-a]pyridine-8-carboxylic acid,
3-p-chlorobenzoyl-5,6,7,8-tetrahydropyrrolo[1,2-a]pyridine-8-carboxylic acid,
3-o-methoxybenzoyl-5,6,7,8-tetrahydropyrrolo[1,2-a]pyridine-8-carboxylic acid,
3-p-methoxybenzoyl-5,6,7,8-tetrahydropyrrolo[1,2-a]pyridine-8-carboxylic acid,
3-benzoyl-2-methyl-5,6,7,8-tetrahydropyrrolo[1,2-a]pyridine-8-carboxylic acid and
3-o-fluorobenzoyl-2-ethyl-5,6,7,8-tetrahydropyrrolo[1,2-a]pyridine-8-carboxylic acid; and
3-p-chlorobenzoyl-6,7,8,9-tetrahydro-5H-pyrrolo[1,2-a]azepine-9-carboxylate,
3-o-methoxybenzoyl-6,7,8,9-tetrahydro-5H-pyrrolo[1,2-a]azepine-9-carboxylate,
3-p-methoxybenzoyl-6,7,8,9-tetrahydro-5H-pyrrolo[1,2-a]azepine-9-carboxylate,
3-benzoyl-2-methyl-6,7,8,9-tetrahydro-5H-pyrrolo[1,2-a]azepine-9-carboxylate and
3-o-fluorobenzoyl-2-ethyl-6,7,8,9-tetrahydro-5H-pyrrolo[1,2-a]azepine-9-carboxylate for 3-p-toluoyl-5,6,7,8-tetrahydropyrrolo[1,2-a]pyridine-8-carboxylic acid there are obtained the corresponding calcium and magnesium salts.

EXAMPLE 52

To a solution of 283 mg. of 3-p-toluoyl-5,6,7,8-tetrahydropyrrolo[1,2-a]pyridine-8-carboxylic acid in 10 ml. of methanol is added 1 molar equivalent of potassium hydroxide in the form of a 0.1 N solution. The solvent is stripped and the residue is dissolved in 2 ml. of water. The thus obtained aqueous solution of potassium 3-p-toluoyl-5,6,7,8-tetrahydropyrrolo[1,2-a]pyridine-8-carboxylate is added to a solution of 63 mg. of cupric nitrate trihydrate in 5 ml. of water. The formed precipitate is collected, washed with water and air dried, thus obtaining copper 3-p-toluoyl-5,6,7,8-tetrahydropyrrolo[1,2-a]pyridine-8-carboxylate.

In a similar manner the free acid compounds obtained in Examples 8, 9, 11, 24B-29, 31, 34, 36, 38, 40, 42, 44 and 47 can be converted into the corresponding copper salts.

EXAMPLE 53

A solution of 283 mg. of 3-p-toluoyl-5,6,7,8-tetrahydropyrrolo[1,2-a]pyridine-8-carboxylic acid in 50 ml. of hot benzene is treated with 60 mg. of isopropylamine. The solution is allowed to cool to room temperature and the product filtered off, washed with ether and dried to yield the isopropylamine salt of 3-p-toluoyl-5,6,7,8-tetrahydropyrrolo[1,2-a]pyridine-8-carboxylic acid.

Likewise other amine salts, e.g., diethylamine, ethanolamine, piperidine, tromethamine, choline and caffeine salts of 3-p-toluoyl-5,6,7,8-tetrahydropyrrolo[1,2-a]pyridine-8-carboxylic acid are prepared by substituting each of the respective amines for isopropylamine.

In similar manner the free acid compounds obtained in Examples 8, 9, 11, 24B-29, 31, 36, 38, 40, 42, 44 and 47 can be converted into the corresponding isopropylamine, diethylamine, ethanolamine, piperidine, tromethamine, chline and caffeine salts.

EXAMPLE 54

A solution of 283 mg. of 3-o-toluoyl-5,6,7,8-tetrahydropyrrolo[1,2-a]pyridine-8-carboxylic acid in 50 ml. of benzene is treated with dicyclohexylamine. The reaction mixture is stirred for 10 minutes, and the solid which forms is separated by filtration and washed with anhydrous ether thus obtaining 190 mg. of the dicyclohexylamine salt of 3-o-toluoyl-5,6,7,8-tetrahydropyrrolo[1,2-a]pyridine-8-carboxylic acid.

In a similar manner the free acid compounds obtained in Examples 8, 9, 11, 24B-29, 31, 36, 38, 40, 42, 44 and 47 can be converted into the corresponding dicyclohexylamine salts.

EXAMPLE 55

| Ingredients | Quantity per tablet, mgs. |
|---|---|
| 3-benzoyl-5,6,7,8-tetrahydropyrrolo[1,2,-a]pyridine-8-carboxylic acid | 25 |
| cornstarch | 20 |
| lactose, spray-dried | 153 |
| magnesium stearate | 2 |

The above ingredients are thoroughly mixed and pressed into single scored tablets.

EXAMPLE 56

| Ingredients | Quantity per tablet, mgs. |
|---|---|
| 3-benzoyl-5,6,7,8-tetrahydropyrrolo[1,2-a]pyridine-8-carboxylic acid | 200 |
| cornstarch | 50 |
| lactose | 145 |
| magnesium stearate | 5 |

The above ingredients are mixed intimately and pressed into single scored tablets.
5-benzoyl-6,7,8,9-tetrahydro-5H-pyrrolo[1,2-a]azepine-9-carboxylic acid is substituted for the compound of the above composition.

EXAMPLE 57

| Ingredients | Quantity per tablet, mgs. |
|---|---|
| sodium 3-benzoyl-5,6,7,8-tetrahydropyrrolo[1,2-a]pyridine-8-carboxylate | 108 |
| lactose | 15 |
| cornstarch | 25 |
| magnesium stearate | 2 |

The above ingredients are mixed and introduced into a hard-shell gelatin capsule.

EXAMPLE 58

| Ingredients | Quantity per tablet, mgs. |
|---|---|
| calcium-3-benzoyl-5,6,7,8-tetrahydropyrrolo[1,2-a]pyridine-8-carboxylate | 115 |
| lactose | 93 |
| cornstarch | 40 |
| magnesium stearate | 2 |

The above ingredients are mixed and introduced into a hard-shell gelatin capsule.

EXAMPLE 59

| Ingredients | Quantity per tablet, mgs. |
|---|---|
| isopropylammonium 3-benzoyl-6,7,8,9-tetrahydro-5H-pyrrolo[1,2-a]azepine-9-carboxylate | 245 |
| cornstarch | 75 |
| lactose | 175 |
| magnesium stearate | 5 |

The above ingredients are mixed intimately and pressed into single scored tablets.

EXAMPLE 60

| Ingredients | Quantity per tablet, mgs. |
|---|---|
| methyl 3-benzoyl-5,6,7,8-tetrahydropyrrolo[1,2-a]pyridine-8-carboxylate | 25 |
| lactose | 125 |

The above ingredients are mixed and introduced into a No. 1 hard-shell gelatin capsule.

EXAMPLE 61

| Ingredients | Quantity per tablet, mgs. |
|---|---|
| 3-benzoyl-5,6,7,8-tetrahydropyrrolo[1,2-a]pyridine-8-carboxylic acid | 300 |
| sucrose | 300 |

The above ingredients are thoroughly mixed and processed into single scored tablets, one tablet being administered every three to four hours.

EXAMPLE 62

| Ingredients | Quantity per tablet, mgs. |
|---|---|
| isoamyl 3-benzoyl-6,7,8,9-tetra-hydro-5H-pyrrolo[1,2-a]azepine-9-carboxylate | 254 |
| cornstarch | 50 |
| lactose | 190 |
| magnesium stearate | 6 |

The above ingredients are mixed intimately and pressed into single scored tablets.

EXAMPLE 63

| Ingredients | Quantity per tablet, mgs. |
|---|---|
| 3-benzoyl-5,6,7,8-tetra-hydropyrrolo[1,2-a]pyridine-8-carboxylic acid | 100 |
| lactose | 148 |
| dextrose | 2 |

The above ingredients are mixed and introduced into a hard-shell gelatin capsule.
3-benzoyl-6,7,8,9-tetrahydro-5H-pyrrolo[1,2-a]azepine-9-carboxylatic acid is substituted compound of the above composition.

EXAMPLE 64

| Ingredients | Quantity per tablet, mgs. |
|---|---|
| methyl 3-benzoyl-5,6,7,8-tetra-hydropyrrolo[1,2-a]pyridine-8-carboxylate | 158 |
| lactose | 92 |

The above ingredients are mixed and introduced into a hard-shell gelatin capsule.

EXAMPLE 65

| Ingredients | Quantity per tablet, mgs. |
|---|---|
| isoamyl 3-benzoyl-5,6,7,8-tetra-hydropyrrolo[1,2-a]pyridine-8-carboxylate | 127 |
| lactose | 91 |
| cornstarch | 25 |
| magnesium stearate | 2 |
| gelatin | 5 |

The above ingredients are mixed and pressed into single scored tablets.

EXAMPLE 66

| Ingredients | Quantity per tablet, mgs. |
|---|---|
| calcium 3-benzoyl-5,6,7,8-tetra-hydropyrrolo[1,2-a]pyridine-8-carboxylate | 230 |
| cornstarch (paste) | 40 |
| cornstarch | 50 |
| magnesium stearate | 2 |
| lactose | 178 |

The above ingredients are thoroughly mixed and pressed into single scored tablets.

EXAMPLE 67

| Ingredients | Quantity per tablet, mgs. |
|---|---|
| sodium 5,6,7,8-tetra-hydropyrrolo[1,2-a]pyridine-8-carboxylate | 217 |
| cornstarch | 50 |
| magnesium stearate | 2 |
| gelatin | 226 |
| lactose | 5 |

The above ingredients are mixed intimately and pressed into single scored tablets.

EXAMPLE 68

| Ingredients | Quantity per tablet, mgs. |
|---|---|
| isopropylammonium 3-benzoyl-5,6,7,8-tetra-hydropyrrolo[1,2-a]pyridine-8-carboxylate | 122 |
| cornstarch | 30 |
| lactose | 98 |

The above ingredients are mixed and introduced into a hard-shell gelatin capsule.

EXAMPLE 69

| Ingredients | Quantity per tablet, mgs. |
|---|---|
| isoamyl 3-benzoyl-5,6,7,8-tetra-hydropyrrolo[1,2-a]pyridine-8-carboxylate | 32 |
| lactose | 101 |
| cornstarch | 15 |
| magnesium stearate | 2 |

The above ingredients are mixed and introduced into a hard-shell gelatin capsule.

EXAMPLE 70

An injectable preparation buffered to a pH of 7 is prepared having the following composition:

| | |
|---|---|
| 3-benzoyl-5,6,7,8-tetra-hydropyrrolo[1,2-a]pyridine-8-carboxylic acid | 0.2 g |
| $K_2HPO_4$ buffer (0.4 M solution) | 2 ml. |
| KOH (1N) | q.s. to pH7 |
| water (distilled sterile) | q.s. to 20 ml. |

3-benzoyl-6,7,8,9-tetrahydro-5H-pyrrolo[1,2-a]azepine-9-carboxylic acid is substituted for the compound of the above composition.

EXAMPLE 71

A suppositiory totaling 2.8 grams is prepared having the following composition:

| | |
|---|---|
| 3-benzoyl-5,6,7,8-tetra-hydropyrrolo[1,2-a]pyridine-8-carboxylic acid | 25 mg. |
| Witepsol H-15 (triglycerides of saturated vegetable fatty acids; a product of Riches-Nelson, Inc., New York, N.Y.) | balance |

3-benzoyl-6,7,8,9-tetrahydro-5H-pyrrolo[1,2-a]azepine-9-carboxylic acid is substituted for the compound of the above composition.

EXAMPLE 72

An oral suspension for pediatric use is prepared having the following composition:

| | |
|---|---|
| 3-benzoyl-5,6,7,8-tetrahydropyrrolo[1,2-a]pyridine-8-carboxylic acid | 0.1 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water | q.s. to 100 ml. |

3-benzoyl-6,7,8,9-tetrahydro-5H-pyrrolo[1,2-a]azepine-9-carboxylic acid is substituted for the compound of the above composition.

EXAMPLES 73-74

Powdered top dressings for veterinary use are prepared having the following compositions:

| | Ex. 73 | Ex. 74 |
|---|---|---|
| 3-benzoyl-5,6,7,8-tetrahydropyrrolo[1,2-a]pyridine-8-carboxylic acid | 0.1 g. | 1.2 g. |
| sucrose | 5.7 g. | 3.7 g. |
| polyvinyl pyrrolidone | 0.3 g. | 0.3 g. |

3-benzoyl-6,7,8,9-tetrahydro-5H-pyrrolo[1,2-a]azepine-9-carboxylic acid is substituted for the compound of the composition of Example 73.

3-benzoyl-6,7,8,9-tetrahydro-5H-pyrrolo[1,2-a]azepine-9-carboxylic acid is substituted for the compound of the composition of Example 74.

EXAMPLE 75

| Ingredients | Quantity per tablet, mgs. |
|---|---|
| 3-(2-thenoyl)-5,6,7,8-tetrahydropyrrolo[1,2-a]pyridine-8-carboxylic acid | 25 |
| cornstarch | 20 |
| lactose, spray-dried | 153 |
| magnesium stearate | 2 |

The above ingredients are thoroughly mixed and pressed into single scored tablets.

EXAMPLE 76

| Ingredients | Quantity per tablet, mgs. |
|---|---|
| 3-(2-thenoyl)-5,6,7,8-tetrahydropyrrolo[1,2-a]pyridine-8-carboxylic acid | 200 |
| cornstarch | 50 |
| lactose | 145 |
| magnesium stearate | 5 |

The above ingredients are mixed intimately and pressed into single scored tablets.

3-(2-thenoyl)-6,7,8,9-tetrahydro-5H-pyrrolo[1,2-a]azepine-9-carboxylic acid is substituted for the compound of the above composition.

EXAMPLE 77

| Ingredients | Quantity per tablet, mgs. |
|---|---|
| potassium 3-(2-thenoyl)-5,6,7,8-tetrahydropyrrolo[1,2-a]pyridine-8-carboxylate | 108 |
| lactose | 15 |
| cornstarch | 25 |
| magnesium stearate | 2 |

The above ingredients are mixed and introduced into a hard-shell gelatin capsule.

EXAMPLE 78

| Ingredients | Quantity per tablet, mgs. |
|---|---|
| calcium 3-(2-thenoyl)-5,6,7,8-tetrahydropyrrolo[1,2-a]pyridine-8-carboxylate | 115 |
| lactose | 93 |
| cornstarch | 40 |
| magnesium stearate | 2 |

The above ingredients are mixed and introduced into a hard-shell gelatin capsule.

EXAMPLE 79

| Ingredients | Quantity per tablet, mgs. |
|---|---|
| isopropylammonium 3-(2-thenoyl)-5,6,7,8-tetrahydropyrrolo[1,2-a]pyridine-8-carboxylate | 245 |
| cornstarch | 75 |
| lactose | 175 |
| magnesium stearate | 5 |

The above ingredients are mixed intimately and pressed into single scored tablets.

EXAMPLE 80

| Ingredients | Quantity per tablet, mgs. |
|---|---|
| methyl 3-(2-thenoyl)-5,6,7,8-tetrahydropyrrolo[1,2-a]pyridine-8-carboxylate | 25 |
| lactose | 125 |

The above ingredients are mixed and introduced into a No. 1 hard-shell gelatin capsule.

EXAMPLE 81

| Ingredients | Quantity per tablet, mgs. |
|---|---|
| 3-(2-thenoyl)-5,6,7,8-tetrahydropyrrolo[1,2-a]pyridine-8-carboxylic acid | 300 |
| sucrose | 300 |

The above ingredients are thoroughly mixed and processed into single scored tablets, one tablet being administered every three to four hours.

EXAMPLE 82

| Ingredients | Quantity per tablet, mgs. |
|---|---|
| isoamyl 3-(2-thenoyl)-5,6,7,8-tetrahydropyrrolo-[1,2-a]pyridine-8-carboxylate | 254 |
| cornstarch | 50 |
| lactose | 190 |
| magnesium stearate | 6 |

The above ingredients are mixed intimately and pressed into single scored tablets.

EXAMPLE 83

| Ingredients | Quantity per tablet, mgs. |
|---|---|
| 3-(2-thenoyl)-5,6,7,8-tetrahydropyrrolo-[1,2-a]pyridine-8-carboxylic acid | 100 |
| lactose | 148 |
| dextrose | 2 |

The above ingredients are mixed and introduced into a hard-shell gelatin capsule.
3-(2-thenoyl)-6,7,8,9-tetrahydro-5H-pyrrolo[1,2-a]azepine-9-carboxylic acid is substituted for the compound of the above composition.

EXAMPLE 84

| Ingredients | Quantity per tablet, mgs. |
|---|---|
| methyl 3-(2-thenoyl)-5,6,7,8-tetrahydropyrrolo-[1,2-a]pyridine-8-carboxylate | 158 |
| lactose | 92 |

The above ingredients are mixed and introduced into a hard-shell gelatin capsule.

EXAMPLE 85

| Ingredients | Quantity per tablet, mgs. |
|---|---|
| isoamyl 3-(2-thenoyl)-5,6,7,8-tetrahydropyrrolo-[1,2-a]pyridine-8-carboxylate | 127 |
| lactose | 91 |
| cornstarch | 25 |
| magnesium stearate | 2 |
| gelatin | 5 |

The above ingredients are mixed and pressed into single scored tablets.

EXAMPLE 86

| Ingredients | Quantity per tablet, mgs. |
|---|---|
| calcium 3-(2-thenoyl)-5,6,7,8-tetrahydropyrrolo-[1,2-a]pyridine-8-carboxylate | 230 |
| cornstarch (paste) | 40 |
| cornstarch | 50 |
| magnesium stearate | 2 |
| lactose | 178 |

The above ingredients are mixed and pressed into single scored tablets.

EXAMPLE 87

| Ingredients | Quantity per tablet, mgs. |
|---|---|
| potassium 3-(2-thenoyl)-5,6,7,8-tetrahydropyrrolo-[1,2-a]pyridine-8-carboxylate | 217 |
| cornstarch | 50 |
| magnesium stearate | 2 |
| gelatin | 226 |
| lactose | 005 |

The above ingredients are mixed and pressed into single scored tablets.

EXAMPLE 88

| Ingredients | Quantity per tablet, mgs. |
|---|---|
| isopropylammonium 3-(2-thenoyl)-5,6,7,8-tetrahydropyrrolo-[1,2-a]pyridine-8-carboxylate | 122 |
| cornstarch | 30 |
| lactose | 98 |

The above ingredients are mixed and introduced into a hard-shell gelatin capsule.

EXAMPLE 89

| Ingredients | Quantity per tablet, mgs. |
|---|---|
| isoamyl 3-(2-thenoyl)-5,6,7,8-tetrahydropyrrolo-[1,2-a]pyridine-8-carboxylate | 32 |
| lactose | 101 |
| cornstarch | 15 |
| magnesium stearate | 2 |

The above ingredients are mixed and introduced into a hard-shell gelatin capsule.

EXAMPLE 90

An injectable preparation buffered to a pH of 7 is prepared having the following composition:

| | |
|---|---|
| 3-(2-thenoyl)-5,6,7,8-tetrahydropyrrolo-[1,2-a]pyridine-8-carboxylic acid | 0.2 g. |
| $K_2HPO_4$ buffer (0.4 M solution) | 2 ml. |
| KOH (1N) | q.s. to pH7 |
| water (distilled sterile) | q.s. to 20 ml. |

3-(2-thenoyl)-6,7,8,9-tetrahydro-5H-pyrrolo[1,2-a]azepine-9-carboxylic acid is substituted for the compound of the above composition.

EXAMPLE 91

A suppository totaling 2.8 grams is prepared having the following composition:

| | |
|---|---|
| 3-(2-thenoyl)-5,6,7,8-tetrahydropyrrolo-[1,2-a]pyridine-8-carboxylic acid | 25 mg. |
| Witepsol H-15 (triglycerides of saturated vegetable fatty acids; a product of Riches-Nelson, Inc., New York, N.Y.) | balance |

3-(2-thenoyl)-6,7,8,9-tetrahydro-5H-pyrrolo[1,2-a]azepine-9-carboxylic acid is substituted for the compound of the above composition.

EXAMPLE 92

An oral suspension for pediatric use is prepared having the following composition:

| | |
|---|---|
| 3-(2-thenoyl)-5,6,7,8-tetrahydropyrrolo-[1,2-a]pyridine-8-carboxylic acid | 0.1 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegem K (Vanderbilt Co.) | 1.0 g. |
| flavoring | 0.035 ml. |
| colorings | 0.5 mg. |
| distilled water | q.s. to 100 ml. |

3-(2-thenoyl)-6,7,8,9-tetrahydro-5H-pyrrolo[1,2-a]azepine-9-carboxylic acid is substituted for the compound of the above composition.

EXAMPLE 93-94

Powdered top dressings for veterinary use are prepared having the following compositions:

| | Ex. 93 | Ex. 94 |
|---|---|---|
| 3-(2-thenoyl)-5,6,7,8-tetrahydropyrrolo[1,2-a]-pyridine-8-carboxylic acid | 0.1 g. | 1.2 g. |
| sucrose | 5.7 g. | 3.7 g. |
| polyvinyl pyrrolidone | 0.3 g. | 0.3 g. |

3-(2-thenoyl)-6,7,8,9-tetrahydro-5H-pyrrolo[1,2-a]azepine-9-carboxylic acid is substituted for the compound of the composition of Example 93.
3-(2-thenoyl)-6,7,8,9-tetrahydro-5H-pyrrolo[1,2-a]azepine-9-carboxylic acid is substituted for the compound of the composition of Example 94.

EXAMPLE 95

| Ingredients | Quantity per tablet, mgs. |
|---|---|
| 3-(2-pyrroyl)-5,6,7,8-tetrahydropyrrolo-[1,2-a]pyridine-8-carboxylic acid | 25 |
| cornstarch | 20 |
| lactose, spray-dried | 153 |
| magnesium stearate | 2 |

The above ingredients are thoroughly mixed and pressed into single scored tablets.

EXAMPLE 96

| Ingredients | Quantity per tablet, mgs. |
|---|---|
| 3-(N—methyl-2-pyrroyl)-5,6,7,8-tetrahydropyrrolo-[1,2-a]pyridine-8-carboxylic acid | 200 |
| cornstarch | 50 |
| lactose | 145 |
| magnesium stearate | 5 |

The above ingredients are mixed intimately and pressed into single scored tablets.

3-(N-methyl-2-pyrroyl)-6,7,8,9-tetrahydro-5H-pyrrolo[1,2-a]azepine-9-carboxylic acid is substituted for the compound of the above composition.

EXAMPLE 97

| Ingredients | Quantity per tablet, mgs. |
|---|---|
| sodium 3-(N—methyl-2-pyrroyl)-5,6,7,8-tetrahydropyrrolo-[1,2-a]pyridine-8-carboxylate | 108 |
| lactose | 15 |
| cornstarch | 25 |
| magnesium stearate | 2 |

The above ingredients are mixed and introduced into a hard-shell gelatin capsule.

EXAMPLE 98

| Ingredients | Quantity per tablet, mgs. |
|---|---|
| calcium 3-(N—methyl-2-pyrroyl)-5,6,7,8-tetrahydropyrrolo-[1,2-a]pyridine-8-carboxylate | 115 |
| lactose | 93 |
| cornstarch | 40 |
| magnesium stearate | 2 |

The above ingredients are mixed and introduced into a hard-shell gelatin capsule.

EXAMPLE 99

| Ingredients | Quantity per tablet, mgs. |
|---|---|
| isopropylammonium 3-(N—methyl-2-pyrroyl)-5,6,7,8-tetrahydropyrrolo[1,2-a]pyridine-8-carboxylate | 245 |
| cornstarch | 75 |
| lactose | 175 |
| magnesium stearate | 5 |

The above ingredients are mixed intimately and pressed into single scored tablets.

EXAMPLE 100

| Ingredients | Quantity per tablet, mgs. |
|---|---|
| isopropyl 3-(N—methyl-2-pyrroyl)-5,6,7,8-tetrahydropyrrolo-[1,2-a]pyridine-8-carboxylate | 25 |
| lactose | 125 |

The above ingredients are mixed and introduced into a No. 1 hard-shell gelatin capsule.

EXAMPLE 101

| Ingredients | Quantity per tablet, mgs. |
|---|---|
| 3-(N—methyl-2-pyrroyl)-5,6,7,8-tetrahydropyrrolo-[1,2-a]pyridine-8-carboxylic acid | 300 |
| sucrose | 300 |

The above ingredients are thoroughly mixed and processed into single scored tablets, one tablet being administered every three to four hours.

EXAMPLE 102

| Ingredients | Quantity per tablet, mgs. |
| --- | --- |
| isoamyl 3-(N—methyl-2-pyrroyl)-5,6,7,8-tetrahydropyrrolo[1,2-a]pyridine-8-carboxylate | 254 |
| cornstarch | 50 |
| lactose | 190 |
| magnesium stearate | 6 |

The above ingredients are mixed intimately and pressed into single scored tablets.

EXAMPLE 103

| Ingredients | Quantity per tablet, mgs. |
| --- | --- |
| 3-(N—methyl-2-pyrroyl)-5,6,7,8-tetrahydropyrrolo[1,2-a]pyridine-8-carboxylic acid | 100 |
| lactose | 148 |
| dextrose | 2 |

The above ingredients are mixed and introduced into a hard-shell gelatin capsule.
3-(N-methyl-2-pyrroyl)-6,7,8,9-tetrahydro-5H-pyrrolo[1,2-a]azepine-9-carboxylic acid is substituted for the compound of the above composition.

EXAMPLE 104

| Ingredients | Quantity per tablet, mgs. |
| --- | --- |
| methyl 3-(N—methyl-2-pyrroyl)-5,6,7,8-tetrahydropyrrolo[1,2-a]pyridine-8-carboxylate | 158 |
| lactose | 92 |

The above ingredients are mixed and introduced into a hard-shell gelatin capsule.

EXAMPLE 105

| Ingredients | Quantity per tablet, mgs. |
| --- | --- |
| isoamyl 3-(N—methyl-2-pyrroyl)-5,6,7,8-tetrahydropyrrolo[1,2-a]pyridine-8-carboxylate | 127 |
| lactose | 91 |
| cornstarch | 25 |
| magnesium stearate | 2 |
| gelatin | 5 |

The above ingredients are mixed and pressed into single tablets.

EXAMPLE 106

| Ingredients | Quantity per tablet, mgs. |
| --- | --- |
| calcium 3-(N—methyl-2-pyrroyl)-5,6,7,8-tetrahydropyrrolo[1,2-a]pyridine-8-carboxylate | 230 |
| cornstarch (paste) | 40 |
| cornstarch | 50 |
| magnesium stearate | 2 |
| lactose | 178 |

The above ingredients are thoroughly mixed and pressed into single scored tablets.

EXAMPLE 107

| Ingredients | Quantity per tablet, mgs. |
| --- | --- |
| sodium 3-(N—methyl-2-pyrroyl)-5,6,7,8-tetrahydropyrrolo[1,2-a]pyridine-8-carboxylate | 217 |
| cornstarch | 50 |
| magnesium stearate | 2 |
| gelatin | 226 |
| lactose | 5 |

The above ingredients are mixed intimately and pressed into single scored tablets.

EXAMPLE 108

| Ingredients | Quantity per tablet, mgs. |
| --- | --- |
| isopropylammonium 3-(N—methyl-2-pyrroyl)-5,6,7,8-tetrahydropyrrolo[1,2-a]pyridine-8-carboxylate | 122 |
| cornstarch | 30 |
| lactose | 98 |

The above ingredients are mixed and introduced into a hard-shell gelatin capsule.

EXAMPLE 109

| Ingredients | Quantity per tablet, mgs. |
| --- | --- |
| isoamyl 3-(N—methyl)-2-pyrroyl)-5,6,7,8-tetrahydropyrrolo[1,2-a]pyridine-8-carboxylate | 32 |
| lactose | 101 |
| cornstarch | 15 |
| magnesium stearate | 2 |

The above ingredients are mixed and introduced into a hard-shell gelatin capsule.

EXAMPLE 110

An injectable preparation buffered to a pH of 7 is prepared having the following composition:

| Ingredients | Quantity per tablet, mgs. |
| --- | --- |
| 3-(N—methyl-2-pyrroyl)-5,6,7,8-tetrahydropyrrolo[1,2-a]-pyridine-8-carboxylic acid | 0.2 g |
| K$_2$HPO$_4$ buffer (0.4 M solution) | 2 ml. |
| KOH (1N) | q.s. to pH7 |
| water (distilled sterile) | q.s. to 20 ml. |

3-(N-methyl-2-pyrroyl)=6,7,8,9-tetrahydro-5H-pyrrolo[1,2-a]azepine-9-carboxylic acid is substituted for the compound of the above composition.

EXAMPLE 111

A suppository totaling 2.8 grams is prepared having the following composition:

| | |
| --- | --- |
| 3-(N—2-methyl-2-pyrroyl)-5,6,7,8-tetrahydropyrrolo[1,2-a]pyridine-8-carboxylic acid | 25 mg. |
| Witepsol H-15 (triglycerides of saturated vegetable fatty acids; a product of Riches-Nelson, Inc., New York, N.Y.) | balance |

3-(N-methyl-2-pyrroyl)-6,7,8,9-tetrahydro-5H-pyrrolo[1,2-a]azepine-9-carboxylic acid is substituted for the compound of the above composition.

EXAMPLE 112

An oral suspension for pediatric use is prepared having the following composition:

| | |
|---|---|
| 3-(N—methyl-2-pyrroyl)-5,6,7,8-tetrahydropyrrolo[1,2-a]pyridine-8-carboxylic acid | 0.1 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water | q.s. to 100 ml. |

3-(N-methyl-2-pyrroyl)-6,7,8,9-tetrahydro-5H-pyrrolo[1,2-a]azepine-9-carboxylic acid is substituted for the compound of the above composition.

EXAMPLE 113–114

Powdered top dressings for veterinary use are prepared having the following compositions:

| | Ex. 113 | Ex. 114 |
|---|---|---|
| 3-(N—methyl-2-pyrroyl)-5,6,7,8-tetrahydropyrrolo-[1,2-a]-pyridine-8-carboxylic acid | 0.1 g. | 1.2 g. |
| sucrose | 5.7 g. | 3.7 g. |
| polyvinyl pyrrolidone | 0.3 g. | 0.3 g. |

3-(N-methyl-2-pyrroyl)-6,7,8,9-tetrahydro-5H-pyrrolo[1,2-a]azepine-9-carboxylic acid is substituted for the compound of the composition of Example 113.

3-(N-methyl-2-pyrroyl)-6,7,8,9-tetrahydro-5H-pyrrolo[1,2-a]azepine-9-carboxylic acid is substituted for the compound of the composition of Example 114.

The subject matter claimed is:

1. A therapeutic composition having an inhibiting activity on blood platelet aggregation comprising, as active ingredient, an effective amount of a compound selected from the group of those represented by the formula:

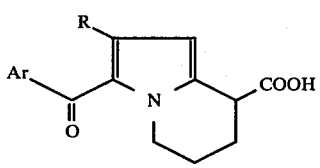

and the pharmaceutically acceptable, non-toxic alkyl esters having from 1 to 12 carbon atoms and salts thereof, wherein
Ar is a radical selected from the group of those having the formula:

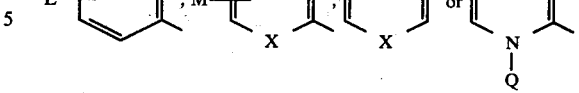

in which
X is selected from the group consisting of sulfur or oxygen,
L is selected from the group consisting of hydrogen, alkyl containing 1 to 4 carbon atoms, alkoxy containing 1 to 4 carbon atoms, Br, Cl, F, $CF_3$, CN, $SR_3$,

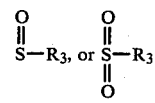

wherein $R_3$ is alkyl containing 1 to 4 carbon atoms
M is selected from the group consisting of hydrogen, methyl, Cl or Br,
Q is selected from the group consisting of hydrogen or alkyl containing 1 to 4 carbon atoms; and
R is selected from the group consisting of hydrogen, alkyl containing from 1 to 4 carbon atoms, Cl or Br, in admixture with a pharmaceutically acceptable excipient.

2. A method of inhibiting blood platelet aggregation in mammals, which method comprises administering to a subject in need of such treatment a therapeutically effective amount of, or a composition containing a therapeutically effective amount of, a compound selected from the group of those represented by the formula

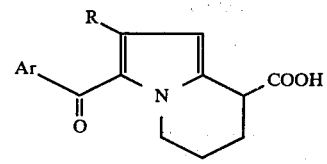

and the pharmaceutically acceptable, non-toxic alkyl esters having from 1 to 12 carbon atoms and salts thereof, wherein
Ar is a radical selected from the group of those having the formula:

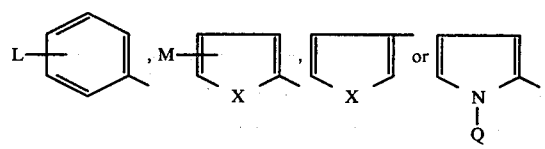

in which
X is selected from the group consisting of sulfur or oxygen,
L is selected from the group consisting of hydrogen, alkyl containing 1 to 4 carbon atoms, alkoxy containing 1 to 4 carbon atoms, Br, Cl, F, $CF_3$, CN, $SR_3$,

EXAMPLE 102

| Ingredients | Quantity per tablet, mgs. |
|---|---|
| isoamyl 3-(N—methyl-2-pyrroyl)-5,6,7,8-tetrahydropyrrolo[1,2-a]pyridine-8-carboxylate | 254 |
| cornstarch | 50 |
| lactose | 190 |
| magnesium stearate | 6 |

The above ingredients are mixed intimately and pressed into single scored tablets.

EXAMPLE 103

| Ingredients | Quantity per tablet, mgs. |
|---|---|
| 3-(N—methyl-2-pyrroyl)-5,6,7,8-tetrahydropyrrolo[1,2-a]pyridine-8-carboxylic acid | 100 |
| lactose | 148 |
| dextrose | 2 |

The above ingredients are mixed and introduced into a hard-shell gelatin capsule.
3-(N-methyl-2-pyrroyl)-6,7,8,9-tetrahydro-5H-pyrrolo[1,2-a]azepine-9-carboxylic acid is substituted for the compound of the above composition.

EXAMPLE 104

| Ingredients | Quantity per tablet, mgs. |
|---|---|
| methyl 3-(N—methyl-2-pyrroyl)-5,6,7,8-tetrahydropyrrolo[1,2-a]pyridine-8-carboxylate | 158 |
| lactose | 92 |

The above ingredients are mixed and introduced into a hard-shell gelatin capsule.

EXAMPLE 105

| Ingredients | Quantity per tablet, mgs. |
|---|---|
| isoamyl 3-(N—methyl-2-pyrroyl)-5,6,7,8-tetrahydropyrrolo[1,2-a]pyridine-8-carboxylate | 127 |
| lactose | 91 |
| cornstarch | 25 |
| magnesium stearate | 2 |
| gelatin | 5 |

The above ingredients are mixed and pressed into single tablets.

EXAMPLE 106

| Ingredients | Quantity per tablet, mgs. |
|---|---|
| calcium 3-(N—methyl-2-pyrroyl)-5,6,7,8-tetrahydropyrrolo[1,2-a]pyridine-8-carboxylate | 230 |
| cornstarch (paste) | 40 |
| cornstarch | 50 |
| magnesium stearate | 2 |
| lactose | 178 |

The above ingredients are thoroughly mixed and pressed into single scored tablets.

EXAMPLE 107

| Ingredients | Quantity per tablet, mgs. |
|---|---|
| sodium 3-(N—methyl-2-pyrroyl)-5,6,7,8-tetrahydropyrrolo[1,2-a]pyridine-8-carboxylate | 217 |
| cornstarch | 50 |
| magnesium stearate | 2 |
| gelatin | 226 |
| lactose | 5 |

The above ingredients are mixed intimately and pressed into single scored tablets.

EXAMPLE 108

| Ingredients | Quantity per tablet, mgs. |
|---|---|
| isopropylammonium 3-(N—methyl-2-pyrroyl)-5,6,7,8-tetrahydropyrrolo[1,2-a]pyridine-8-carboxylate | 122 |
| cornstarch | 30 |
| lactose | 98 |

The above ingredients are mixed and introduced into a hard-shell gelatin capsule.

EXAMPLE 109

| Ingredients | Quantity per tablet, mgs. |
|---|---|
| isoamyl 3-(N—methyl)-2-pyrroyl)-5,6,7,8-tetrahydropyrrolo[1,2-a]pyridine-8-carboxylate | 32 |
| lactose | 101 |
| cornstarch | 15 |
| magnesium stearate | 2 |

The above ingredients are mixed and introduced into a hard-shell gelatin capsule.

EXAMPLE 110

An injectable preparation buffered to a pH of 7 is prepared having the following composition:

| Ingredients | Quantity per tablet, mgs. |
|---|---|
| 3-(N—methyl-2-pyrroyl)-5,6,7,8-tetrahydropyrrolo[1,2-a]pyridine-8-carboxylic acid | 0.2 g |
| K$_2$HPO$_4$ buffer (0.4 M solution) | 2 ml. |
| KOH (1N) | q.s. to pH7 |
| water (distilled sterile) | q.s. to 20 ml. |

3-(N-methyl-2-pyrroyl)=6,7,8,9-tetrahydro-5H-pyrrolo[1,2-a]azepine-9-carboxylic acid is substituted for the compound of the above composition.

EXAMPLE 111

A suppository totaling 2.8 grams is prepared having the following composition:

| | |
|---|---|
| 3-(N—2-methyl-2-pyrroyl)-5,6,7,8-tetrahydropyrrolo[1,2-a]pyridine-8-carboxylic acid | 25 mg. |
| Witepsol H-15 (triglycerides of saturated vegetable fatty acids; a product of Riches-Nelson, Inc., New York, N.Y.) | balance |

3-(N-methyl-2-pyrroyl)-6,7,8,9-tetrahydro-5H-pyrrolo[1,2-a]azepine-9-carboxylic acid is substituted for the compound of the above composition.

EXAMPLE 112

An oral suspension for pediatric use is prepared having the following composition:

| | |
|---|---|
| 3-(N—methyl-2-pyrroyl)-5,6,7,8-tetrahydropyrrolo[1,2-a]pyridine-8-carboxylic acid | 0.1 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water | q.s. to 100 ml. |

3-(N-methyl-2-pyrroyl)-6,7,8,9-tetrahydro-5H-pyrrolo[1,2-a]azepine-9-carboxylic acid is substituted for the compound of the above composition.

EXAMPLE 113-114

Powdered top dressings for veterinary use are prepared having the following compositions:

| | Ex. 113 | Ex. 114 |
|---|---|---|
| 3-(N—methyl-2-pyrroyl)-5,6,7,8-tetrahydropyrrolo-[1,2-a]-pyridine-8-carboxylic acid | 0.1 g. | 1.2 g. |
| sucrose | 5.7 g. | 3.7 g. |
| polyvinyl pyrrolidone | 0.3 g. | 0.3 g. |

3-(N-methyl-2-pyrroyl)-6,7,8,9-tetrahydro-5H-pyrrolo[1,2-a]azepine-9-carboxylic acid is substituted for the compound of the composition of Example 113.

3-(N-methyl-2-pyrroyl)-6,7,8,9-tetrahydro-5H-pyrrolo[1,2-a]azepine-9-carboxylic acid is substituted for the compound of the composition of Example 114.

The subject matter claimed is:

1. A therapeutic composition having an inhibiting activity on blood platelet aggregation comprising, as active ingredient, an effective amount of a compound selected from the group of those represented by the formula:

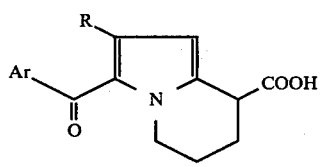

and the pharmaceutically acceptable, non-toxic alkyl esters having from 1 to 12 carbon atoms and salts thereof, wherein Ar is a radical selected from the group of those having the formula:

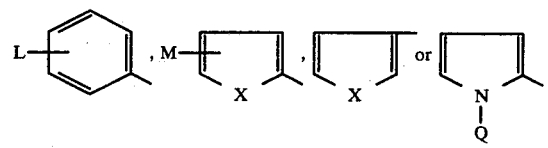

in which

X is selected from the group consisting of sulfur or oxygen,

L is selected from the group consisting of hydrogen, alkyl containing 1 to 4 carbon atoms, alkoxy containing 1 to 4 carbon atoms, Br, Cl, F, $CF_3$, CN, $SR_3$,

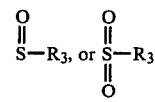

wherein $R_3$ is alkyl containing 1 to 4 carbon atoms

M is selected from the group consisting of hydrogen, methyl, Cl or Br,

Q is selected from the group consisting of hydrogen or alkyl containing 1 to 4 carbon atoms; and R is selected from the group consisting of hydrogen, alkyl containing from 1 to 4 carbon atoms, Cl or Br, in admixture with a pharmaceutically acceptable excipient.

2. A method of inhibiting blood platelet aggregation in mammals, which method comprises administering to a subject in need of such treatment a therapeutically effective amount of, or a composition containing a therapeutically effective amount of, a compound selected from the group of those represented by the formula

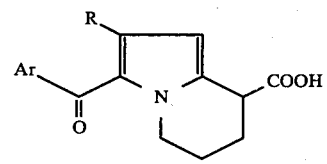

and the pharmaceutically acceptable, non-toxic alkyl esters having from 1 to 12 carbon atoms and salts thereof, wherein Ar is a radical selected from the group of those having the formula:

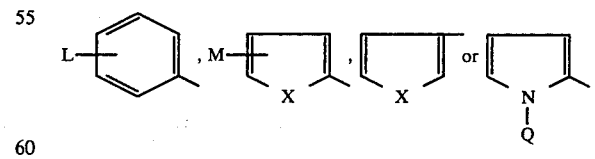

in which

X is selected from the group consisting of sulfur or oxygen,

L is selected from the group consisting of hydrogen, alkyl containing 1 to 4 carbon atoms, alkoxy containing 1 to 4 carbon atoms, Br, Cl, F, $CF_3$, CN, $SR_3$,

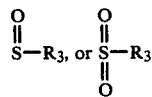

wherein $R_3$ is alkyl containing 1 to 4 carbon atoms

M is selected from the group consisting of hydrogen, methyl, Cl or Br,

Q is selected from the group consisting of hydrogen or alkyl containing 1 to 4 carbon atoms; and R is selected from the group consisting of hydrogen, alkyl containing from 1 to 4 carbon atoms, Cl or Br.

3. The therapeutic composition of claim 1 wherein the active ingredient is a compound, as described therein, in which R and L are each hydrogen, namely 3-benzoyl-5,6,7,8-tetrahydro-pyrrolo[1,2-a]pyridine-8-carboxylic acid, or a pharmaceutically acceptable, non-toxic alkyl ester having from 1 to 12 carbon atoms or salt thereof.

4. The method of claim 2 wherein the compound is 3-benzoyl-5,6,7,8-tetrahydro-pyrrolo[1,2-a]pyridine-8 carboxylic acid, or a pharmaceutically acceptable, non-toxic alkyl ester having from 1 to 12 carbon atoms or salt thereof.

* * * * *